US012667436B2

(12) United States Patent
Wu et al.

(10) Patent No.: US 12,667,436 B2
(45) Date of Patent: Jun. 30, 2026

(54) SURGICAL PATHWAY PROCESSING SYSTEM, METHOD, DEVICE, AND STORAGE MEDIUM

(71) Applicant: WUHAN UNITED IMAGING SURGICAL CO., LTD., Wuhan (CN)

(72) Inventors: Dong Wu, Wuhan (CN); Shaowen He, Wuhan (CN); Yunhong Yang, Wuhan (CN); Guoqiang Wang, Wuhan (CN)

(73) Assignee: WUHAN UNITED IMAGING SURGICAL CO., LTD., Wuhan (CN)

( * ) Notice: Subject to any disclaimer, the term of this patent is extended or adjusted under 35 U.S.C. 154(b) by 296 days.

(21) Appl. No.: 18/492,743

(22) Filed: Oct. 23, 2023

(65) Prior Publication Data

US 2024/0050172 A1 Feb. 15, 2024

Related U.S. Application Data

(63) Continuation of application No. PCT/CN2022/088607, filed on Apr. 22, 2022.

(30) Foreign Application Priority Data

| | | |
|---|---|---|
| Apr. 23, 2021 | (CN) ......................... | 202110440930.9 |
| Apr. 28, 2021 | (CN) ......................... | 202110465791.5 |

(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/10* (2016.02); *A61B 34/25* (2016.02); *B25J 9/1664* (2013.01);
(Continued)

(58) Field of Classification Search
CPC ......... A61B 34/30; A61B 34/10; A61B 34/25; A61B 2034/101; A61B 2034/105;
(Continued)

(56) References Cited

U.S. PATENT DOCUMENTS

| | | | | |
|---|---|---|---|---|
| 6,173,433 | B1* | 1/2001 | Katoh | ................ G02B 6/12004 716/139 |
| 12,213,743 | B2* | 2/2025 | Mahfouz | ............. A61F 2/30942 |

(Continued)

FOREIGN PATENT DOCUMENTS

| | | |
|---|---|---|
| CN | 102961187 A | 3/2013 |
| CN | 103700086 A | 4/2014 |

(Continued)

OTHER PUBLICATIONS

Partial Supplementary European Search Report in European Application No. 22791147.6 mailed on Sep. 19, 2024, 9 pages.

(Continued)

*Primary Examiner* — Sohana Tanju Khayer
(74) *Attorney, Agent, or Firm* — Poseidon Advanced IP LLC

(57) ABSTRACT

Embodiments of the present disclosure provide a surgical pathway processing system, method, device, and storage medium. The system comprises an image segmentation module configured to obtain a first segmented image by performing image segmentation on a first medical image; an avoidance region determination module configured to determine a region to be avoided based on the first segmented image; and a pathway planning module configured to determine a surgical pathway based on the region to be avoided.

20 Claims, 28 Drawing Sheets

(a)

(b)

(c)

(30) Foreign Application Priority Data

| | | |
|---|---|---|
| Jun. 25, 2021 | (CN) | 202110714580.0 |
| Jun. 29, 2021 | (CN) | 202110728649.5 |

(51) Int. Cl.

| | |
|---|---|
| A61B 34/10 | (2016.01) |
| B25J 9/16 | (2006.01) |
| G05B 19/4155 | (2006.01) |
| G06T 7/11 | (2017.01) |
| G06T 7/174 | (2017.01) |
| G06T 7/33 | (2017.01) |
| G06N 20/00 | (2019.01) |

(52) U.S. Cl.

CPC ............ G05B 19/4155 (2013.01); G06T 7/11 (2017.01); G06T 7/174 (2017.01); G06T 7/337 (2017.01); *A61B 2034/101* (2016.02); *A61B 2034/105* (2016.02); *A61B 2034/107* (2016.02); *G05B 2219/50391* (2013.01); *G06N 20/00* (2019.01); *G06T 2207/20021* (2013.01); *G06T 2207/20092* (2013.01); *G06T 2207/30004* (2013.01)

(58) Field of Classification Search

CPC ............. A61B 2034/107; B25J 9/1664; G05B 19/4155; G05B 2219/50391; G06T 7/11; G06T 7/174; G06T 7/337; G06T 2207/20021; G06T 2207/20092; G06T 2207/30004; G06T 2207/10081; G06T 2207/20101; G06T 7/33; G06N 20/00

See application file for complete search history.

(56) References Cited

U.S. PATENT DOCUMENTS

| | | | | |
|---|---|---|---|---|
| 12,322,111 | B2* | 6/2025 | Lin | G06N 3/084 |
| 2004/0109603 | A1* | 6/2004 | Bitter | G06T 15/10 |
| | | | | 382/154 |
| 2007/0208234 | A1 | 9/2007 | Bhandarkar et al. | |
| 2009/0118609 | A1* | 5/2009 | Rahn | A61B 6/12 |
| | | | | 606/34 |
| 2009/0252394 | A1* | 10/2009 | Liang | G06T 7/0012 |
| | | | | 382/131 |
| 2011/0007071 | A1 | 1/2011 | Pfister | |
| 2012/0070052 | A1* | 3/2012 | Maroy | G06T 7/149 |
| | | | | 382/131 |
| 2012/0155734 | A1* | 6/2012 | Barratt | G06T 7/344 |
| | | | | 382/128 |
| 2013/0188846 | A1* | 7/2013 | Kriston | G06T 7/11 |
| | | | | 382/130 |
| 2014/0270446 | A1* | 9/2014 | Vija | G06T 7/337 |
| | | | | 382/131 |
| 2014/0371911 | A1 | 12/2014 | Mian et al. | |
| 2015/0080930 | A1 | 3/2015 | Kawaura et al. | |
| 2016/0070436 | A1* | 3/2016 | Thomas | G06T 7/0012 |
| | | | | 715/771 |
| 2017/0000567 | A1* | 1/2017 | Kim | A61B 10/0233 |
| 2017/0042495 | A1* | 2/2017 | Matsuzaki | A61B 5/055 |
| 2017/0046833 | A1 | 2/2017 | Lurie et al. | |
| 2017/0243349 | A1* | 8/2017 | Hou | G06V 10/40 |
| 2018/0336676 | A1* | 11/2018 | Dutta | G06T 7/187 |
| 2019/0015160 | A1 | 1/2019 | Maeda | |
| 2019/0060004 | A1 | 2/2019 | Witcomb et al. | |
| 2019/0087960 | A1* | 3/2019 | Jang | G06T 7/11 |
| 2019/0126008 | A1 | 5/2019 | Breininger et al. | |
| 2019/0172205 | A1* | 6/2019 | Mao | G06T 7/187 |
| 2020/0237198 | A1* | 7/2020 | Liu | A61B 1/015 |
| 2020/0297268 | A1 | 9/2020 | Hickey | |
| 2020/0357502 | A1* | 11/2020 | Lee | G16H 20/40 |
| 2020/0394833 | A1 | 12/2020 | Higueras Esteban et al. | |
| 2021/0097702 | A1 | 4/2021 | Brokman et al. | |
| 2021/0209764 | A1* | 7/2021 | Goris | G06T 7/136 |

| | | | | |
|---|---|---|---|---|
| 2021/0287487 | A1* | 9/2021 | Hilbert | G07F 17/3241 |
| 2022/0036561 | A1* | 2/2022 | Liu | G06N 3/0464 |
| 2022/0058821 | A1* | 2/2022 | Fu | G06V 10/75 |
| 2022/0144257 | A1* | 5/2022 | Maeda | B60W 30/095 |
| 2022/0192684 | A1* | 6/2022 | Jacobsen | A61B 34/20 |
| 2022/0202491 | A1* | 6/2022 | Pathak | G06N 3/096 |
| 2022/0237799 | A1* | 7/2022 | Price | G06T 7/174 |
| 2022/0265352 | A1* | 8/2022 | Zucker | G06T 7/12 |
| 2022/0290243 | A1* | 9/2022 | Mitrofanova | G16B 25/10 |
| 2022/0309633 | A1* | 9/2022 | Davies | G06V 10/82 |
| 2022/0313340 | A1* | 10/2022 | Jacobsen | A61B 18/04 |
| 2022/0383508 | A1* | 12/2022 | Liu | G06V 10/82 |
| 2023/0085725 | A1* | 3/2023 | Lonjaret | A61B 90/57 |
| | | | | 700/245 |
| 2023/0162332 | A1* | 5/2023 | Yang | G06T 17/00 |
| | | | | 348/241 |
| 2023/0169668 | A1* | 6/2023 | Yang | G06T 7/11 |
| | | | | 382/128 |
| 2023/0390021 | A1* | 12/2023 | Polchin | A61B 34/30 |
| 2024/0009851 | A1* | 1/2024 | Mousavian | B25J 9/1697 |
| 2025/0152185 | A1* | 5/2025 | Jacobsen | A61B 17/1671 |
| 2025/0160851 | A1* | 5/2025 | Jacobsen | A61B 17/1671 |

FOREIGN PATENT DOCUMENTS

| | | | | |
|---|---|---|---|---|
| CN | 105550993 | A | 5/2016 | |
| CN | 105640583 | A | 6/2016 | |
| CN | 107296645 | A | 10/2017 | |
| CN | 108066011 | A | 5/2018 | |
| CN | 108335304 | A | 7/2018 | |
| CN | 108784831 | A | 11/2018 | |
| CN | 109493943 | A | 3/2019 | |
| CN | 109859833 | A | 6/2019 | |
| CN | 109934235 | A | 6/2019 | |
| CN | 110013306 | A | 7/2019 | |
| CN | 110175958 | A | 8/2019 | |
| CN | 110223303 | A | 9/2019 | |
| CN | 110464459 | A | 11/2019 | |
| CN | 110473196 | A | 11/2019 | |
| CN | 110517300 | A | 11/2019 | |
| CN | 110537960 | A | 12/2019 | |
| CN | 110610497 | A | 12/2019 | |
| CN | 110706236 | A * | 1/2020 | G06T 7/11 |
| CN | 110838104 | A | 2/2020 | |
| CN | 110838140 | A | 2/2020 | |
| CN | 110974366 | A | 4/2020 | |
| CN | 110993065 | A | 4/2020 | |
| CN | 111062997 | A | 4/2020 | |
| CN | 111145160 | A | 5/2020 | |
| CN | 111161241 | A | 5/2020 | |
| CN | 111210431 | A | 5/2020 | |
| CN | 111583188 | A | 8/2020 | |
| CN | 112089482 | A | 12/2020 | |
| CN | 112155729 | A | 1/2021 | |
| CN | 112163987 | A | 1/2021 | |
| CN | 112220557 | A | 1/2021 | |
| CN | 112242193 | A | 1/2021 | |
| CN | 112419377 | A | 2/2021 | |
| CN | 112419378 | A | 2/2021 | |
| CN | 112634285 | A | 4/2021 | |
| CN | 112656510 | A | 4/2021 | |
| CN | 112927274 | A | 6/2021 | |
| CN | 113506331 | A | 10/2021 | |
| CN | 113516623 | A | 10/2021 | |
| CN | 113516624 | A | 10/2021 | |
| JP | 2005038412 | A | 2/2005 | |
| WO | 2016126934 | A1 | 8/2016 | |

OTHER PUBLICATIONS

International Search Report in PCT/CN2022/088607 mailed on Jul. 6, 2022, 7 pages.

Written Opinion in PCT/CN2022/088607 mailed on Jul. 6, 2022, 10 pages.

Zhuang, Jinfeng, Research on Extraction of Thoracic Anatomy and Path Planning Based on Lung Puncture Surgical Navigation, Full-text Database of China's Outstanding Doctoral and Master's Degree

(56) References Cited

OTHER PUBLICATIONS

Theses (Master's) Medical and Health Sciences Seires, 2016, 77 pages.

Fang, Luping et al., Design of Puncture Surgical Navigation System Based on Gyroscope, Journal of Zhejiang University of Technology, 44(2): 129-133, 2016.

Huo, Benyan et al., Puncture Path Planning for Bevel-tip Flexible Needle Based on Multi-objective Particle Swarm Optimization Algorithm, Robot, 37(4): 385-394, 2015.

Ding, Xiangqian, Clinical Research of Spontaneous Intracerebral Hemorrhage by Hematoma Puncture with Three Dimensional Printing Individualized Guide Board, Full-text Database of China's Outstanding Doctoral and Master's Degree Theses (Master's) Medical and Health Sciences Seires, 2018, 50 pages.

Yang, Jie et al., Medical Image Analysis and Three-Dimensional Reconstruction and their Applications, Shanghai Jiaotong University Press, 2015, 12 pages.

Cui, Qiaoyu, Registration and Fusion of Medical Images Based on Multimodality Imaging, Full-text Database of China's Outstanding Doctoral and Master's Degree Theses (Master's) Information Technology Series, 2014, 57 pages.

Liu, Xingang et al., A New Hybridized Rigid-Elastic Multiresolution Algorithm for Medical Image Registration, 2005 IEEE Engineering in Medicine and Biology 27th Annual Conference, 2005, 4 pages.

* cited by examiner

100

<u>300</u>

Obtaining an overall mask, a predetermined object mask, and a to-be-intervened object mask by segmenting the first medical image          310

Determining a region to be avoided based on the overall mask, the predetermined object mask, and the to-be-intervened object mask          320

400

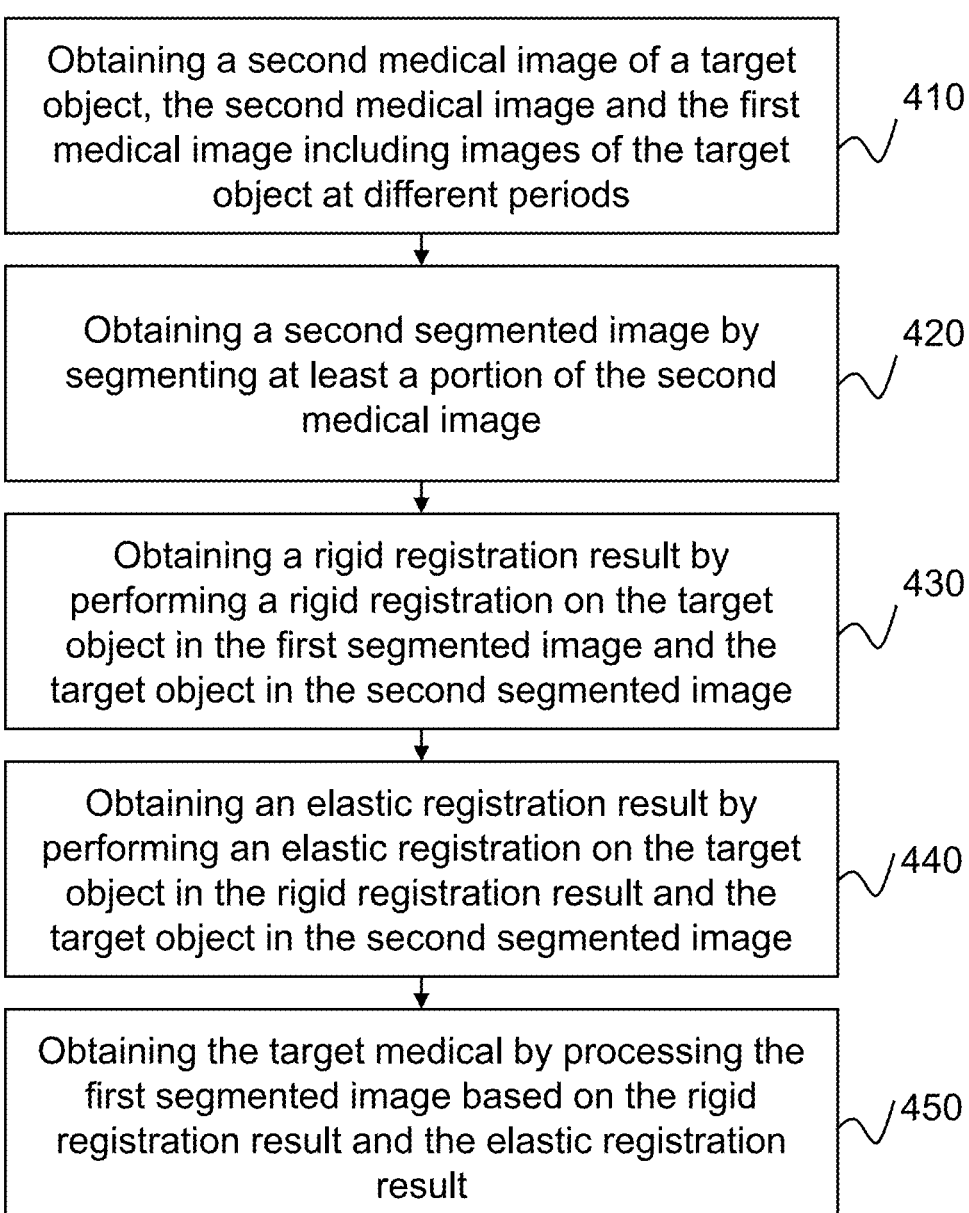

Obtaining a second medical image of a target object, the second medical image and the first medical image including images of the target object at different periods     410

Obtaining a second segmented image by segmenting at least a portion of the second medical image     420

Obtaining a rigid registration result by performing a rigid registration on the target object in the first segmented image and the target object in the second segmented image     430

Obtaining an elastic registration result by performing an elastic registration on the target object in the rigid registration result and the target object in the second segmented image     440

Obtaining the target medical by processing the first segmented image based on the rigid registration result and the elastic registration result     450

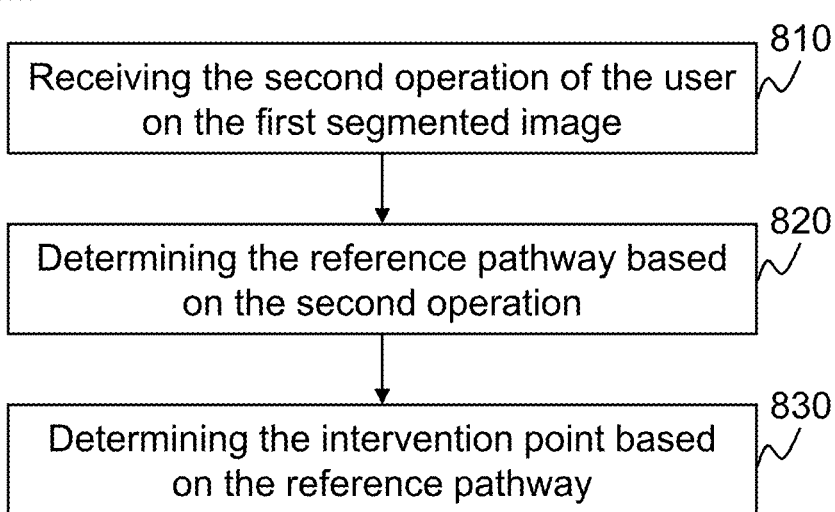

800

```
                                                              810
┌──────────────────────────────────────────┐  ⤳
│   Receiving the second operation of the user  │
│        on the first segmented image           │
└──────────────────────────────────────────┘
                    │
                    ▼                          820
┌──────────────────────────────────────────┐  ⤳
│   Determining the reference pathway based     │
│          on the second operation              │
└──────────────────────────────────────────┘
                    │
                    ▼                          830
┌──────────────────────────────────────────┐  ⤳
│   Determining the intervention point based    │
│           on the reference pathway            │
└──────────────────────────────────────────┘
```

Determining a predetermined normal line    1210

Determining an intervention angle based on the predetermined normal line and the candidate pathway    1220

Determining whether the intervention angle is less than or equal to the predetermined angle threshold    1230

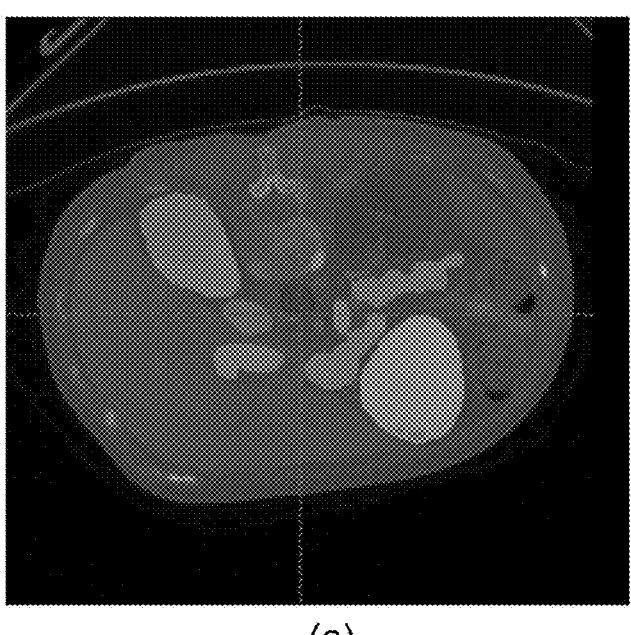
(a)
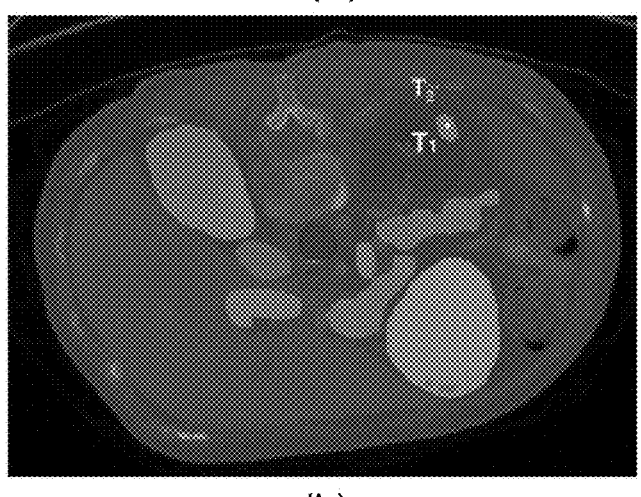
(b)
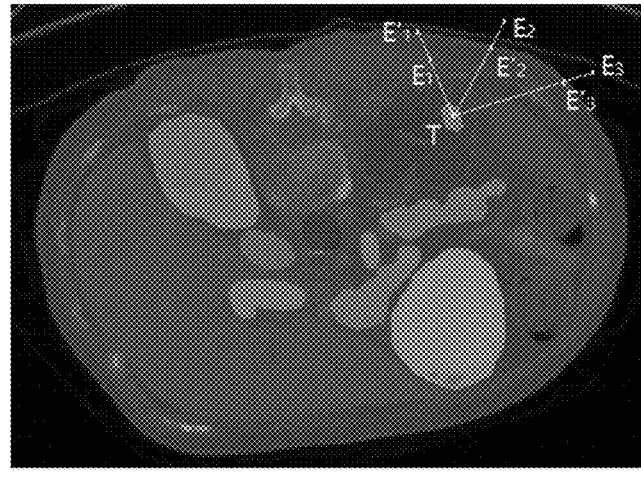
(c)
FIG. 22

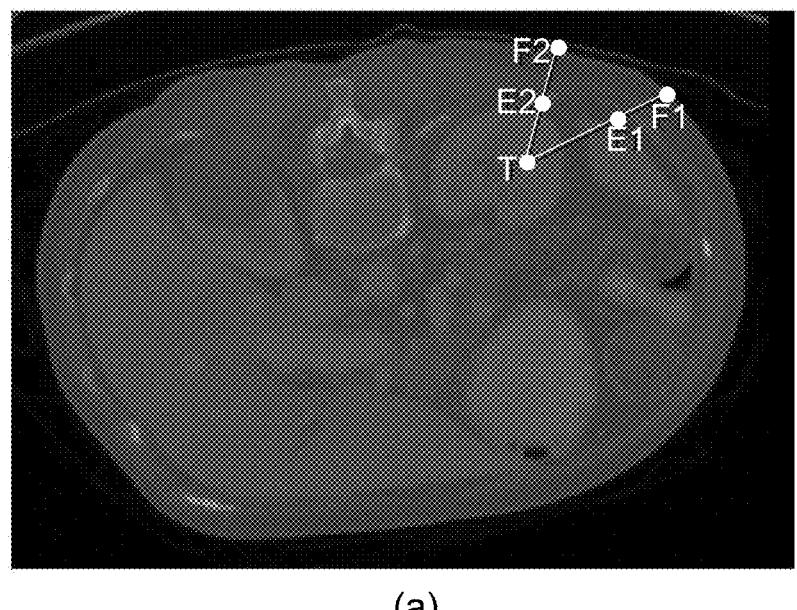
(a)
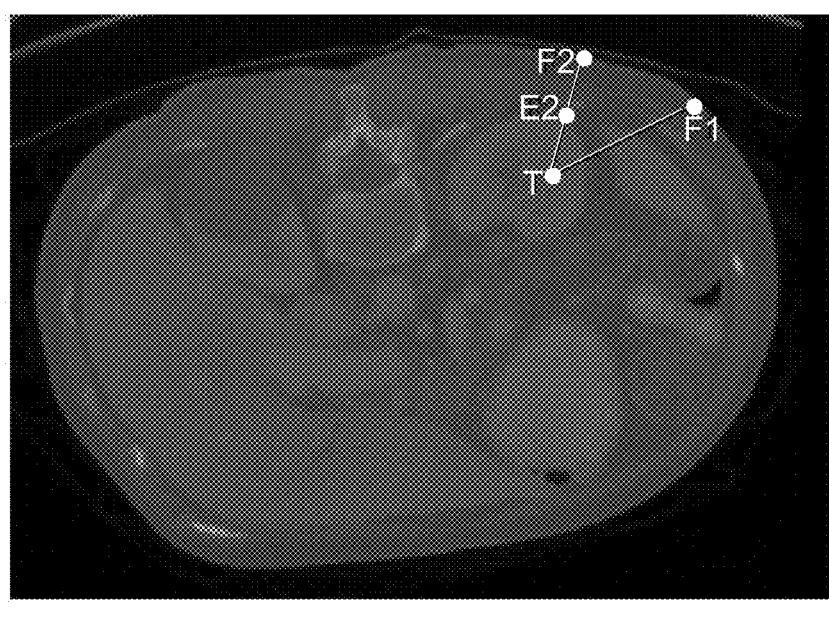
(b)
FIG. 23

<u>1300</u>

<u>1400</u>

1410

Obtaining a first segmented image by performing image segmentation on a first medical image

1420

Determining a region to be avoided based on the first segmented image

1430

Determining a surgical pathway based on the region to be avoided

SURGICAL PATHWAY PROCESSING SYSTEM, METHOD, DEVICE, AND STORAGE MEDIUM

CROSS-REFERENCE TO RELATED APPLICATIONS

This application is a Continuation of International Application No. PCT/CN2022/088607 filed on Apr. 22, 2022, which claims priority of the Chinese Application No. 202110440930.9, filed on Apr. 23, 2021, the Chinese Application No. 202110465791.5, filed on Apr. 28, 2021, the Chinese application No. 202110714580.0, filed on Jun. 25, 2021, and the Chinese Application No. 202110728649.5, filed on Jun. 29, 2021, the entire contents of each of which are incorporated herein by reference.

TECHNICAL FIELD

The present disclosure relates to the field of medical information processing technology, and in particular, to a surgical pathway processing system, method, device, equipment, and storage medium.

BACKGROUND

Surgical pathway planning for interventional procedures is a surgical plan made with the assistance of appropriate medical scanning equipment, acquisition of medical images, and the combination of pathological and anatomical knowledge to introduce customized and precise instruments into the lesion by rationally avoiding intervening risk regions, typically, for example, preoperative planning for interventional procedures. It can be seen that the effect of surgical pathway planning plays a key role in whether interventional procedures can be performed smoothly and whether good surgical results can be obtained.

SUMMARY

One of the embodiments of the present disclosure provides a surgical pathway processing system. The surgical pathway processing system comprises an image segmentation module configured to obtain a first segmented image by performing image segmentation on a first medical image; an avoidance region determination module configured to determine a region to be avoided based on the first segmented image; and a pathway planning module configured to determine a surgical pathway based on the region to be avoided.

One of the embodiments of the present disclosure provides a surgical pathway processing method implemented by the surgical pathway processing system. The surgical pathway processing method comprises obtaining the first segmented image by performing the image segmentation on the first medical image; determining the region to be avoided based on the first segmented image; and determining the surgical pathway based on the region to be avoided.

One of the embodiments of the present disclosure provides a surgical pathway processing device. The surgical pathway processing device comprises an image segmentation unit configured to obtain a first segmented image by performing image segmentation on a first medical image; an avoidance region determination unit configured to determine a region to be avoided based on the first segmented image; and a pathway planning unit configured to determine a surgical pathway based on the region to be avoided.

One of the embodiments of the present disclosure provides a surgical pathway processing device comprising a processor configured to perform the surgical pathway processing method as described in any one of the embodiments.

One of the embodiments of the present disclosure provides a computer-readable storage medium, comprising computer instructions that, when read by a computer, directs the computer to implement the surgical pathway processing method as described in any one of the embodiments.

One of the embodiments of the present disclosure provides a surgical pathway processing device. The surgical pathway processing device comprises a display device; a surgical robot; and a control device. The control device includes one or more processors and a storage. The storage includes operation instructions configured to direct the one or more processors to perform operations. The operations include obtaining a first segmented image by performing image segmentation on a first medical image displayed by the display device; determining a region to be avoided based on the first segmented image; determining a surgical pathway based on the region to be avoided; and driving the surgical robot to move based on the surgical pathway.

BRIEF DESCRIPTION OF THE DRAWINGS

The present disclosure will be further illustrated by way of exemplary embodiments, which will be described in detail with the accompanying drawings. These embodiments are non-limiting. In these embodiments, the same numbering denotes the same structure, wherein:

FIG. 13 is a flowchart illustrating an exemplary registration using finite elements according to some embodiments of the present disclosure;

FIG. 17 is a flowchart illustrating an exemplary process for determining an intervention point according to some embodiments of the present disclosure;

FIG. 22 is a schematic diagram illustrating an exemplary process for determining a surgical pathway according to some embodiments of the present disclosure;

FIG. 23 is a schematic diagram illustrating an exemplary process for determining a surgical pathway according to some other embodiments of the present disclosure;

DETAILED DESCRIPTION

Figure 1:
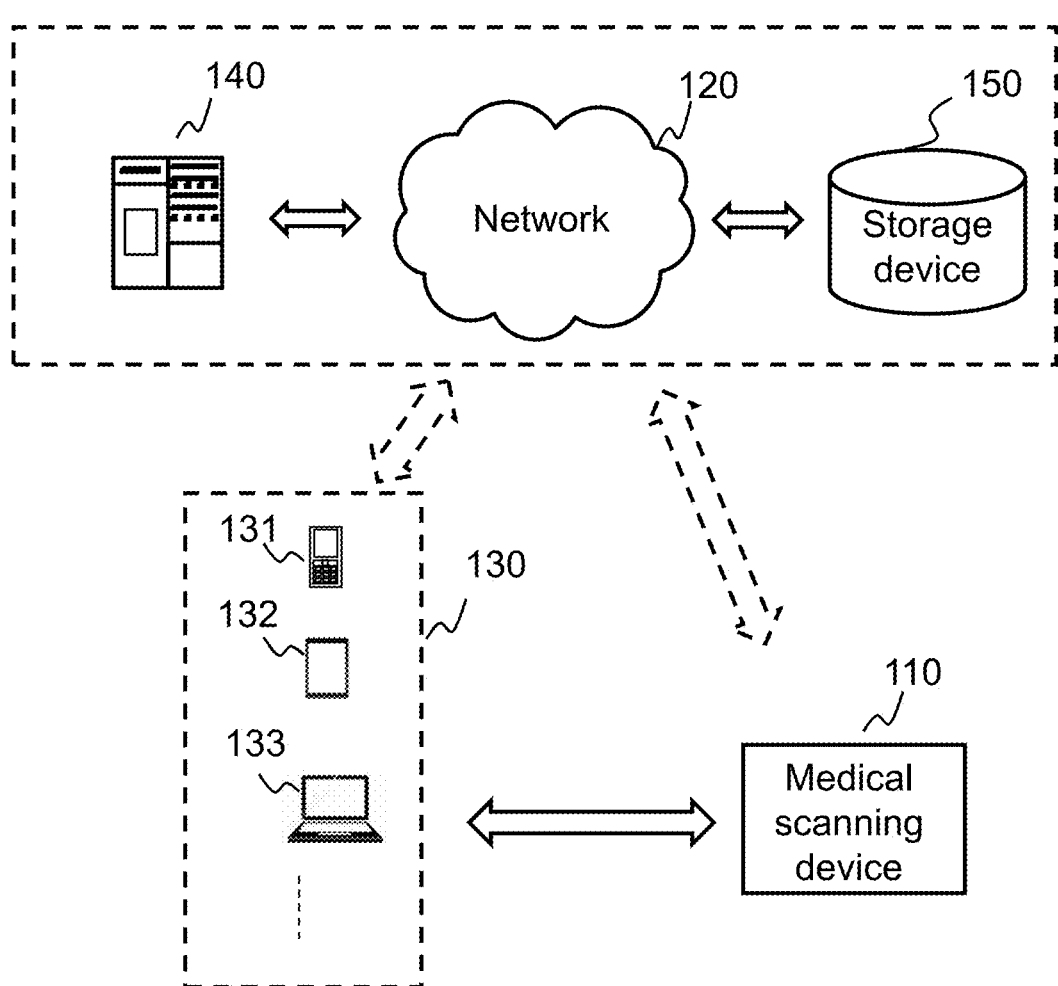
FIG. 1 is a schematic diagram illustrating an application scenario of a surgical pathway processing system according to some embodiments of the present disclosure.

In order to more clearly illustrate the technical solutions of the embodiments of the present disclosure, the following briefly introduces the drawings that need to be used in the description of the embodiments. Apparently, the accompanying drawings in the following description are only some examples or embodiments of the present disclosure, and those skilled in the art can also apply the present disclosure to other similar scenarios according to the drawings without creative efforts. Unless obviously obtained from the context or the context illustrates otherwise, the same numeral in the drawings refers to the same structure or operation.

It should be understood that "system", "device", "unit" and/or "module" as used herein is a method for distinguishing different components, elements, parts, portions, or assemblies of different levels. However, the words may be replaced by other expressions if other words can achieve the same purpose.

As shown in this disclosure and the claims, unless the context clearly indicates otherwise, the words "a", "an", "one", and/or "the" does not refer specifically to the singular form, but may also include the plural form. Generally, the terms "comprising" and "including" only suggest the inclusion of clearly identified steps and elements, and these steps and elements do not constitute an exclusive list, and the method or device may also contain other steps or elements.

Flowcharts are used in the present disclosure to illustrate operations performed by the system according to the embodiments of the present disclosure. It should be understood that the preceding or following operations are not necessarily performed in a specific sequence. Instead, steps may be processed in reverse order or simultaneously. Furthermore, other operations may be added to these processes, or a step or steps can be removed from these processes.

FIG. 1 is a schematic diagram illustrating an application scenario of a surgical pathway processing system 100 according to some embodiments of the present disclosure.

In some embodiments, the surgical pathway processing system 100 may be applied to various interventional procedures/interventional treatments. In some embodiments, the interventional procedures/interventional treatments may include cardiovascular interventional procedures, oncology interventional procedures, obstetrics and gynecology interventional procedures, neuromuscular interventional procedures, or any other feasible interventional procedures such as neurological interventional procedures, etc. In some embodiments, the interventional procedures/interventional treatments may include percutaneous needle biopsy, coronary angiography, thrombolytic therapy, stenting, or any other feasible interventional procedures, such as ablation procedures, etc.

The surgical pathway processing system 100 may include a medical scanning device 110, a network 120, one or more terminals 130, a processing device 140, and a storage device 150. Connections between components of the surgical pathway processing system 100 may be variable. As shown in FIG. 1, the medical scanning device 110 may be connected to the processing device 140 via the network 120. As another example, the medical scanning device 110 may be directly connected to the processing device 140, as shown by dotted bi-directional arrows connecting the medical scanning device 110 and the processing device 140. As yet another example, the storage device 150 may be directly connected to the processing device 140 or connected to the processing device 140 via the network 120. Merely by way of example, the terminal 130 may be directly connected to the processing device 140 (as shown by the dotted arrows connecting the terminal 130 and the processing device 140) or connected to the processing device 140 via the network 120.

The medical scanning device 110 may be configured to scan a target object using high-energy rays (e.g., X-rays, gamma rays, etc.) to collect scanning data related to the target object. The scanning data may be used to generate one or more images of the target object. In some embodiments, the medical scanning device 110 may include an ultrasound imaging (US) device, a computed tomography (CT) scanner, a digital radiography (DR) scanner (e.g., mobile digital radiography), a digital subtraction angiography (DSA) scanner, a dynamic spatial reconstruction (DSR) scanner, an X-ray microscopy scanner, a multimodal scanner, or the like, or any combination thereof. In some embodiments, the multimodal scanner may include a computed tomography-positron emission tomography (CT-PET) scanner, and a computed tomography-magnetic resonance imaging (CT-MRI) scanner. The target object may be biological or nonbiological. Merely by way of example, the target object may include a patient, an artificial object (e.g., an artificial phantom), etc. As another example, the target object may include a specific part, organ, and/or tissue of the patient.

The network 120 may include any suitable network that facilitates information and/or data exchange of the surgical pathway processing system 100. In some embodiments, one or more components of the surgical pathway processing system 100 (e.g., the medical scanning device 110, the terminal 130, the processing device 140, and the storage device 150) may perform information and/or data exchange with each other via the network 120. For example, the processing device 140 may obtain image data, such as a first medical image, a second medical image, etc., from the medical scanning device 110 via the network 120. As another example, the processing device 140 may obtain user instructions from the terminal 130 via the network 120.

The network 120 may include a public network (e.g., the Internet), a private network (e.g., a local area network (LAN), a wide area network (WAN), etc.), a wired network (e.g., the Ethernet, a wireless network (e.g., an 802.11 network, a Wi-Fi network, etc.), a cellular network (e.g., a long term evolution (LTE) network), a frame relay network, a virtual private network ("VPN"), a satellite network, a telephony network, a router, a hub, a switch, a server computer, and/or any combination thereof. Merely by way of example, the network 120 may include a cable network, a wired network, a fiber optic network, a telecommunication network, an intranet, a wireless local area network (WLAN), a metropolitan area network (MAN), a public switched telephone network (PSTN), a Bluetooth™ network, a Zig-Bee™ network, a near field communication (NFC) network, or the like, or any combination thereof. In some embodiments, the network 120 may include one or more network access points. For example, the network 120 may include wired and/or wireless network access points such as a base station and/or an Internet exchange point. One or more components of the surgical pathway processing system 100 may be connected to the network 120 to perform data and/or information exchange through these network access points.

The terminal 130 may include a mobile device 131, a tablet computer 132, a laptop computer 133, or the like, or any combination thereof. In some embodiments, the mobile device 131 may include a smart home device, a wearable device, a mobile device, a virtual reality (VR) device, an augmented reality (AR) device, or the like, or any combination thereof. In some embodiments, the smart home device may include a smart lighting device, a control device for a smart electrical device, a smart surveillance device, a smart TV, a smart camera, an intercom, or the like, or any combination thereof. In some embodiments, the mobile device may include a mobile phone, a personal digital assistant (PDA), a gaming device, a navigation device, a point-of-sale (POS) device, a laptop computer, a tablet computer, a desktop computer, or the like, or any combination thereof. In some embodiments, the VR device and/or the AR device may include a VR headset, VR glasses, a VR eye mask, an AR headset, AR glasses, an AR eye mask, or the like, or any combination thereof. For example, the VR device and/or the AR device may include Google Glass™, Oculus Rift™, Hololens™, Gear VR™, etc. In some embodiments, the terminal 130 may be a part of the processing device 140.

The processing device 140 may process data and/or information obtained by the medical scanning device 110, the terminal 130, and/or the storage device 150. For example, the processing device 140 may obtain the data obtained by the medical scanning device 110 and generate a medical image (e.g., a first medical image, a second medical image, etc.) by imaging using the data, and generate segmentation result data (e.g., a first segmented image, a second segmentation image, etc.) by segmenting the medical image. As another example, the processing device 140 may obtain medical image data (e.g., first medical image data, second medical image data, etc.) and/or a scanning protocol from the terminal 130.

In some embodiments, the processing device 140 may be a single server or a server group. The server group may be centralized or distributed. In some embodiments, the processing device 140 may be local or remote. For example, the processing device 140 may access information and/or data stored in the medical scanning device 110, the terminal 130, and/or the storage device 150 via the network 120. As another example, the processing device 140 may be directly connected with the medical scanning device 110, the terminal 130, and/or the storage device 150 to access the stored information and/or data. In some embodiments, the processing device 140 may be implemented on a cloud platform.

The storage device 150 may store data, instructions, and/or any other information. In some embodiments, the storage device 150 may store data obtained from the medical scanning device 110, the terminal 130, and/or the processing device 140. For example, the storage device 150 may store medical image data (e.g., a first segmented image, a second segmented image, etc.), and/or image registration and verification information data obtained from the medical scanning device 110. As another example, the storage device 150 may store a medical image and/or a scanning protocol input from the terminal 130. As yet another example, the storage device 150 may store data (e.g., medical image data, organ mask data, image registration and verification data, etc.) generated by the processing device 140.

In some embodiments, the storage device 150 may store data and/or instructions that the processing device 140 may execute or use to execute the exemplary methods described in the present disclosure. In some embodiments, the storage device 150 may include a mass storage device, a removable storage device, a volatile read/write memory, a read-only memory (ROM), or the like, or any combination thereof. Exemplary mass storage device may include a disk, an optical disk, a solid-state drive, or the like. Exemplary removable storage device may include a flash drive, a floppy disk, an optical disk, a memory card, a compact disk, a tape, or the like. Exemplary volatile read/write memory may include a random access memory (RAM). Exemplary RAM may include a dynamic random access memory (DRAM), a double data rate synchronous dynamic access memory (DDR SDRAM), a static random access memory (SRAM), a thyristor random access memory (T-RAM), a zero capacitance random access memory (Z-RAM), etc. Exemplary ROM may include a mask read-only memory (MROM), a programmable read-only memory (PROM), an erasable programmable read-only memory (EPROM), an electrically erasable programmable read-only memory (EEPROM), a compact disc read-only memory (CD-ROM), and a digital multifunctional disk redistribution memory (DRM), etc. In some embodiments, the storage device 150 may be implemented on the cloud platform.

In some embodiments, the storage device 150 may be connected to the network 120 to communicate with one or more other components (e.g., the processing device 140, and the terminal 130) of the surgical pathway processing system 100. One or more components of the surgical pathway processing system 100 may access the data or the instructions stored in the storage device 150 via the network 120. In some embodiments, the storage device 150 may be directly connected to or communicate with one or more other components (e.g., the processing device 140, the terminal 130) of the surgical pathway processing system 100. In some embodiments, the storage device 150 may be a part of the processing device 140.

The descriptions regarding the surgical pathway processing system 100 are illustrative and are not intended to limit the scope of the present disclosure. A plurality of substitutions, modifications, and variations would be apparent to those of ordinary skill in the art. It may be understood that for those skilled in the art, after understanding the principle of the system, it may be possible to make arbitrary combinations of modules or form subsystems to connect to other modules without deviating from this principle. In some embodiments, the processing device 140 may include an image segmentation module 210, an avoidance region determination module 220, and a pathway planning module 230 of FIG. 2. The image segmentation module 210 may be a different module of a system, or a single module that implements the functions of two or more of the modules. For example, each module may share a common storage module, and each module may have its own storage module. The features, structures, methods, and other features of the exemplary embodiments described in the present disclosure may be combined in various ways to obtain additional and/or alternative exemplary embodiments. For example, the processing device 140 and the medical scanning device 110 may be integrated into a single device. Such variations are within the scope of protection of the present disclosure.

Figure 2:
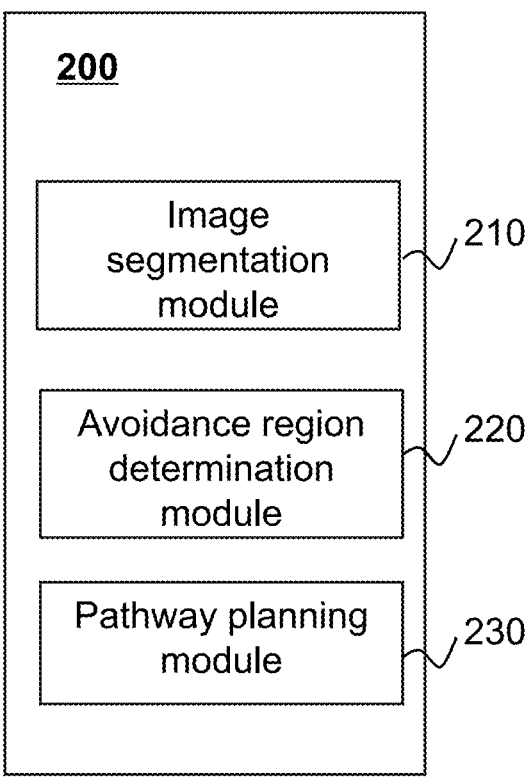
FIG. 2 is a block diagram illustrating an exemplary surgical pathway processing system 200 according to some embodiments of the present disclosure.

FIG. 2 is a block diagram illustrating an exemplary surgical pathway processing system 200 according to some embodiments of the present disclosure. In some embodiments, the surgical pathway processing system 200 may be implemented in the application scenario of the surgical pathway processing system 100 using the processing device 140, the medical scanning device 110, and/or the terminal 130.

The surgical pathway processing system 200 may include an image segmentation module 210, an avoidance region determination module 220, and a pathway planning module 230. The image segmentation module 210 may obtain a first segmented image by performing image segmentation on a first medical image. The avoidance region determination module 220 may determine a region to be avoided based on the first segmented image. The pathway planning module 230 may determine a surgical pathway based on the region to be avoided. The region to be avoided may be determined by analyzing the first segmented image obtained through image segmentation, and then the surgical pathway may be determined based on the region to be avoided, so that the determined surgical pathway is enabled to automatically avoid important tissues, which greatly reduces the dependence on the doctor's experience and improves the efficiency of surgical pathway planning, and accordingly, the user does not need to spend too much time on adjustment, thereby reducing the workload and time of the adjustment operation for the user.

Figure 3:
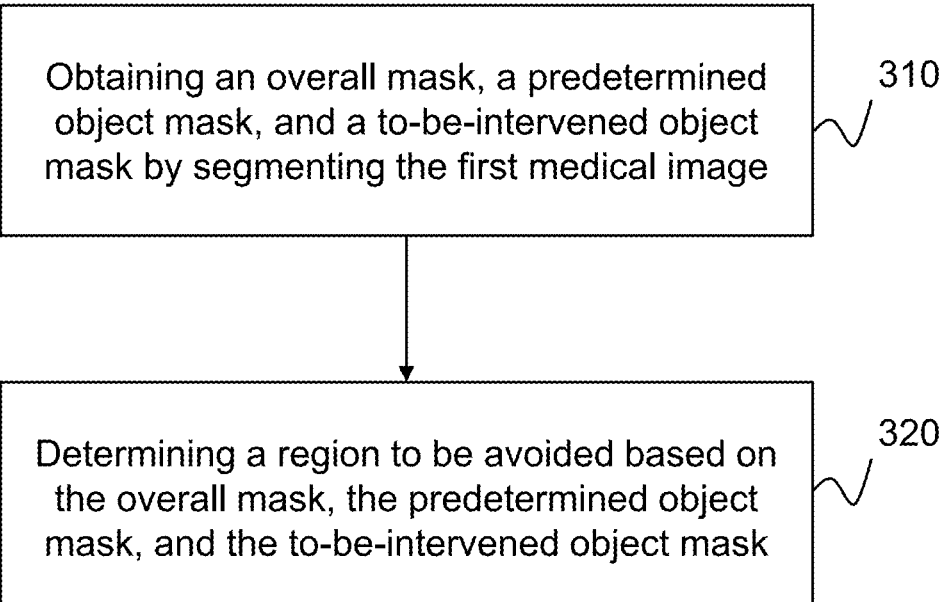
FIG. 3 is a flowchart illustrating exemplary image segmentation of a medical image according to some embodiments of the present disclosure.

FIG. 3 is a flowchart illustrating exemplary image segmentation of a medical image according to some embodiments of the present disclosure.

A first medical image refers to a medical image generated based on various imaging mechanisms. In some embodiments, the first medical image may include a CT image, a PET-CT image, a US image, or an MR image. In some embodiments, the first medical image may include a preoperative enhanced image and an intraoperative scanned image.

In some embodiments, there may be various methods of obtaining the first medical image of a target object. In some embodiments, the first medical image of the target object, such as the CT image, may be obtained from the medical scanning device 110. In some embodiments, the first medical image of the target object, such as the MR image, may be obtained from the terminal 130, the processing device 140, and the storage device 150. In some embodiments, the target object may include a biometric scan object or a non-biometric scan object. In some embodiments, the biometric scan object may include a patient, a specific part, an organ, and/or a tissue of the patient, e.g., an abdomen, a heart, or a tumor tissue, etc. In some embodiments, the non-biometric scan object may include an artificial object, e.g., an artificial phantom, etc. It should be noted that, in other embodiments, the first medical image may be obtained by any other feasible means. For example, the first medical image may be obtained from a cloud server and/or a healthcare system (e.g., a medical system center of a hospital, etc.) via the network 120, which is not limited in the embodiments of the present disclosure.

In some embodiments, the image segmentation module 210 may be configured to implement a segmentation operation on the first medical image, e.g., the CT image, the PET-CT image, or the like. In some embodiments, the image segmentation module 210 may implement segmentation on the first medical image using various manners, e.g., a threshold segmentation manner, a manner based on a deep learning convolutional network, or the like. In some embodiments, the image segmentation module 210 may implement the segmentation on the first medical image using any other feasible manners, which are not limited to the embodiments of the present disclosure.

In some embodiments, the image segmentation module 210 may achieve the segmentation operation of the first medical image through a following process 300. In some embodiments, the process 300 may be implemented by the surgical pathway processing system 100 (e.g., the processing device 140 of the surgical pathway processing system 100) or the surgical pathway processing system 200. For example, the process 300 may be stored in a storage device (e.g., the storage device 150, a storage unit of the system) as a program or an instruction, and the process 300 may be implemented when a processor (e.g., the processing device 140) or modules of FIG. 2 execute(s) the program or the instruction.

In 310, an overall mask, a predetermined object mask, and a to-be-intervened object mask may be obtained by segmenting the first medical image.

In 320, a region to be avoided may be determined based on the overall mask, the predetermined object mask, and the to-be-intervened object mask.

A mask, such as an organ mask, is a pixel-level categorization label. Taking an example of an abdominal medical image for illustration, the mask indicates categorization of pixels in the medical image. For example, the abdominal medical image may be categorized into background, liver, spleen, kidney, etc., with a summarized region of a particular category being represented by a label value. For example, all pixels categorized as the liver may be summarized, and the summarized region may be represented by a label value corresponding to the liver. The label value may be set based on a specific segmentation task.

Figure 6:
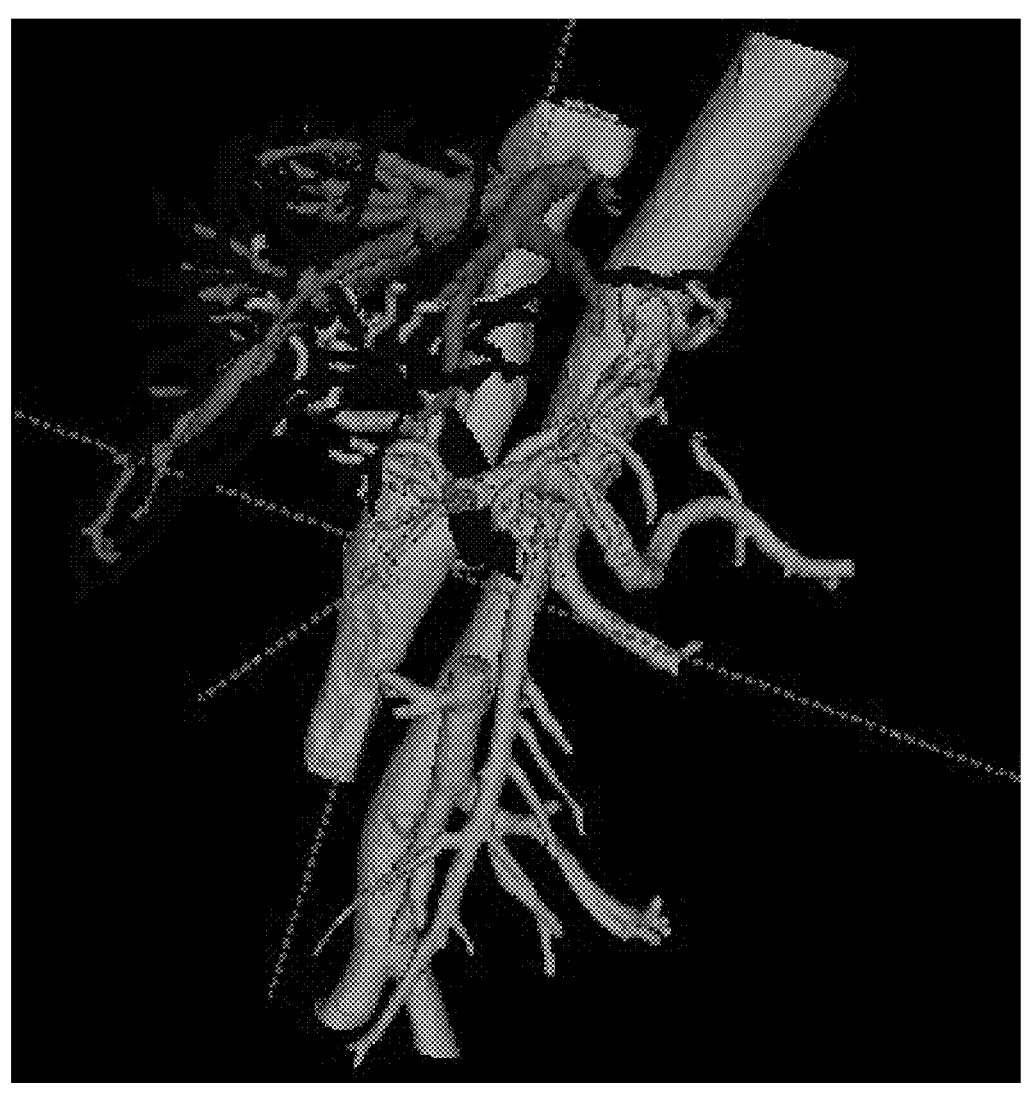
FIG. 6 is a schematic diagram illustrating an abdominal vascular mask according to some embodiments of the present disclosure.
Figure 10:
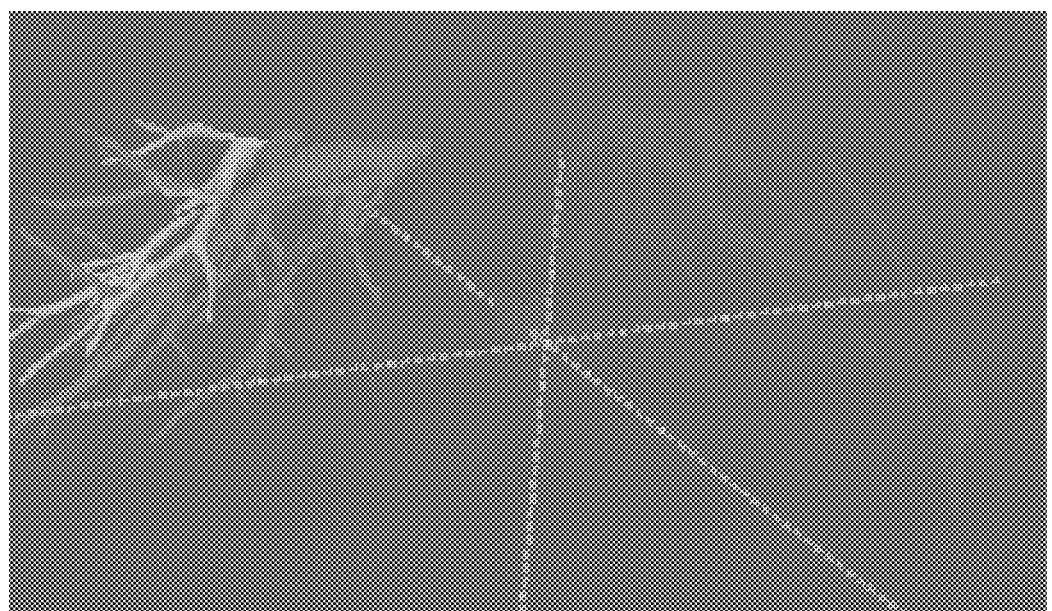
FIG. 10 is a schematic diagram illustrating a septal-apical lung vascular mask according to some embodiments of the present disclosure.

A segmented mask is a mask obtained after the segmentation operation. In some embodiments, the segmented mask may include an organ mask (e.g., an organ mask of a target organ) and a vascular mask, e.g., an exemplary abdominal vascular mask of FIG. 6 and an exemplary septal-apical lung vascular mask of FIG. 10.

Figure 4:
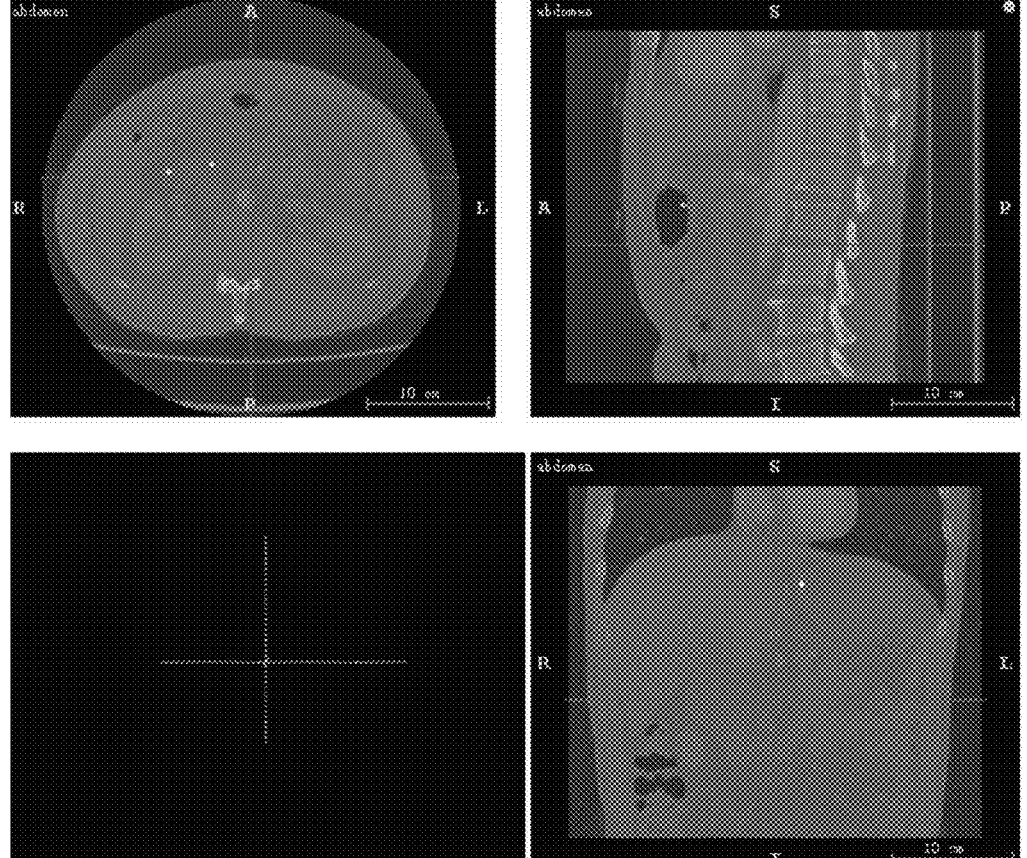
FIG. 4 is a schematic diagram illustrating an abdominal scanning image according to some embodiments of the present disclosure.
Figure 5:
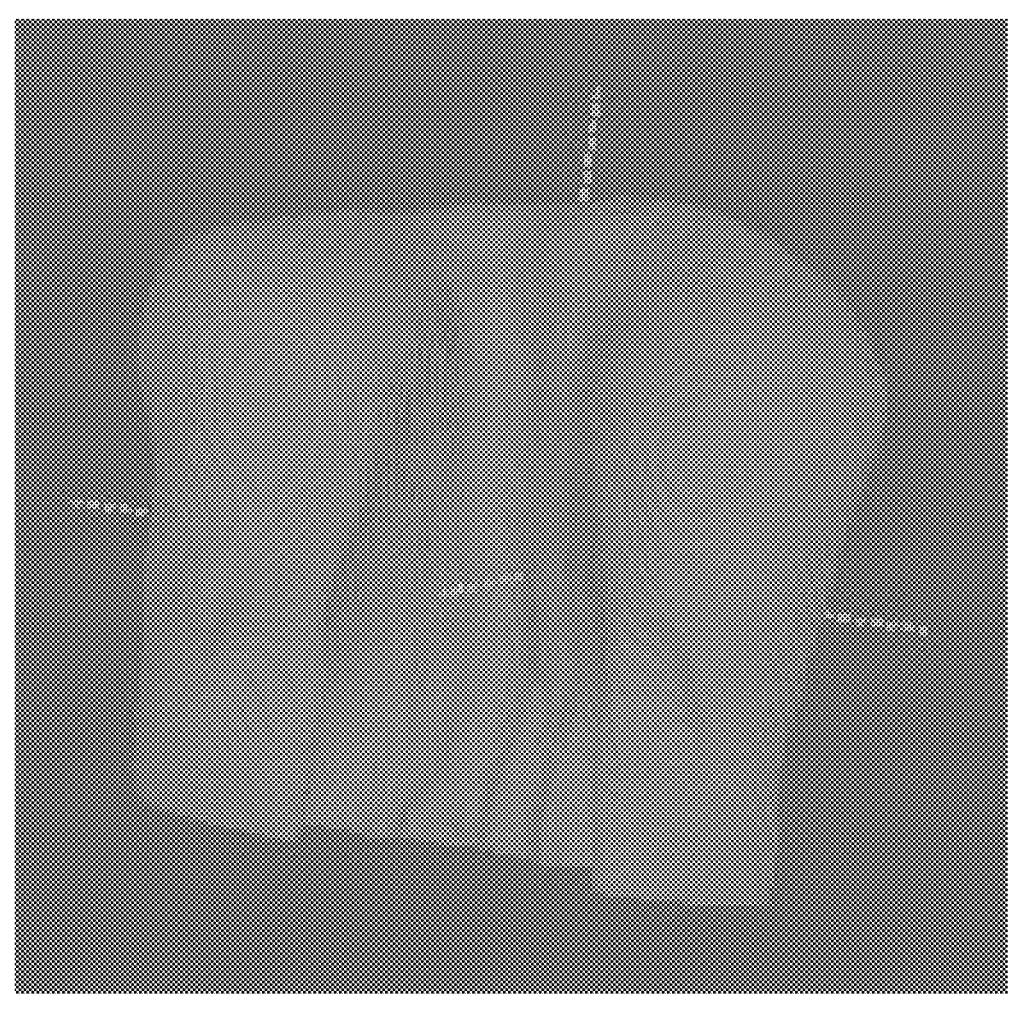
FIG. 5 is a schematic diagram illustrating an abdominal mask according to some embodiments of the present disclosure.
Figure 8:
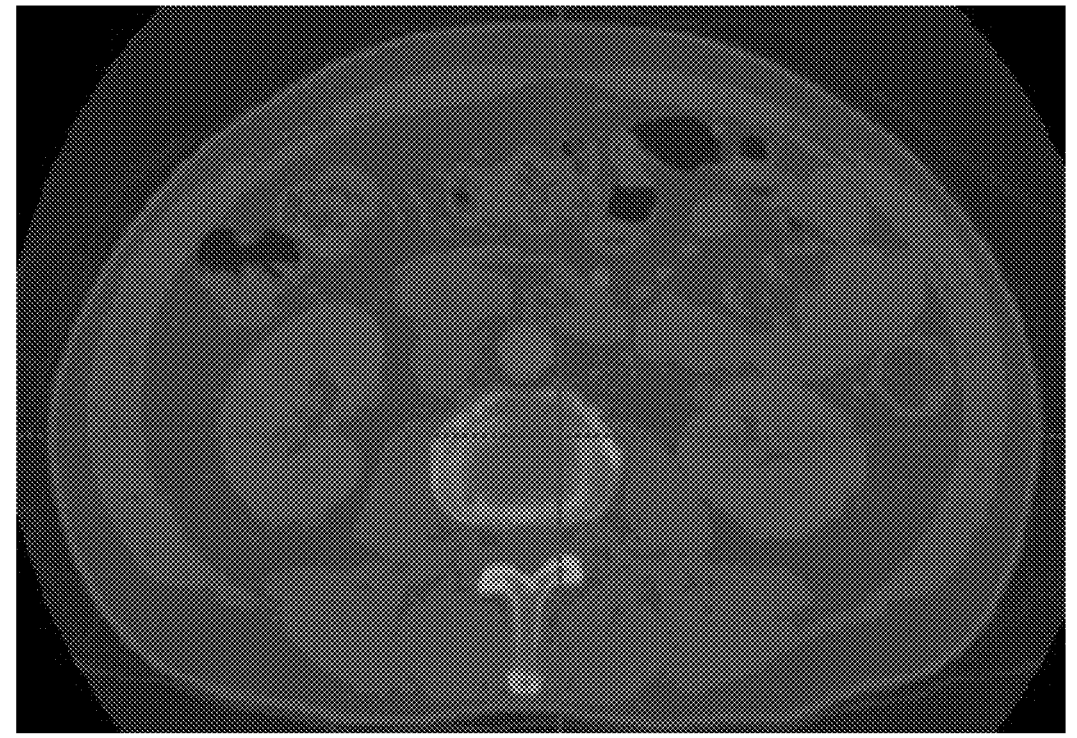
FIG. 8 is a schematic diagram illustrating a fat mask according to some embodiments of the present disclosure.

Still taking the abdominal medical image as an example, as shown in FIG. 4, the overall mask refers to an abdominal mask within an abdominal region. As shown in an exemplary abdominal mask of FIG. 5, the predetermined object mask refers to a specific region mask within the overall mask. In some embodiments, a predetermined object may be fat. In some embodiments, the predetermined object mask may be a fat mask, e.g., an exemplary fat mask shown in FIG. 8.

An interventional procedure (also referred to as interventional treatment) is a minimally invasive therapeutic procedure using modern high-tech means. In some embodiments, the interventional procedure refers to a medical procedure that can be performed under the guidance of a medical scanning device or a medical imaging device, wherein a pathology inside the body is diagnosed and locally treated by introducing a specially designed catheter, guidewire, or other precision instruments into a human body. In some embodiments, a specific type of interventional procedure may include a deep brain stimulation (DBS) procedure, a stereotactic electroencephalography (SEEG) procedure, a puncture-type procedure, or the like. In some embodiments, the interventional procedure may be performed during an actual diagnosis and treatment phase (for the patient) or during an animal testing or simulation phase, which is not specifically limited to the embodiments of the present disclosure.

Figure 7:
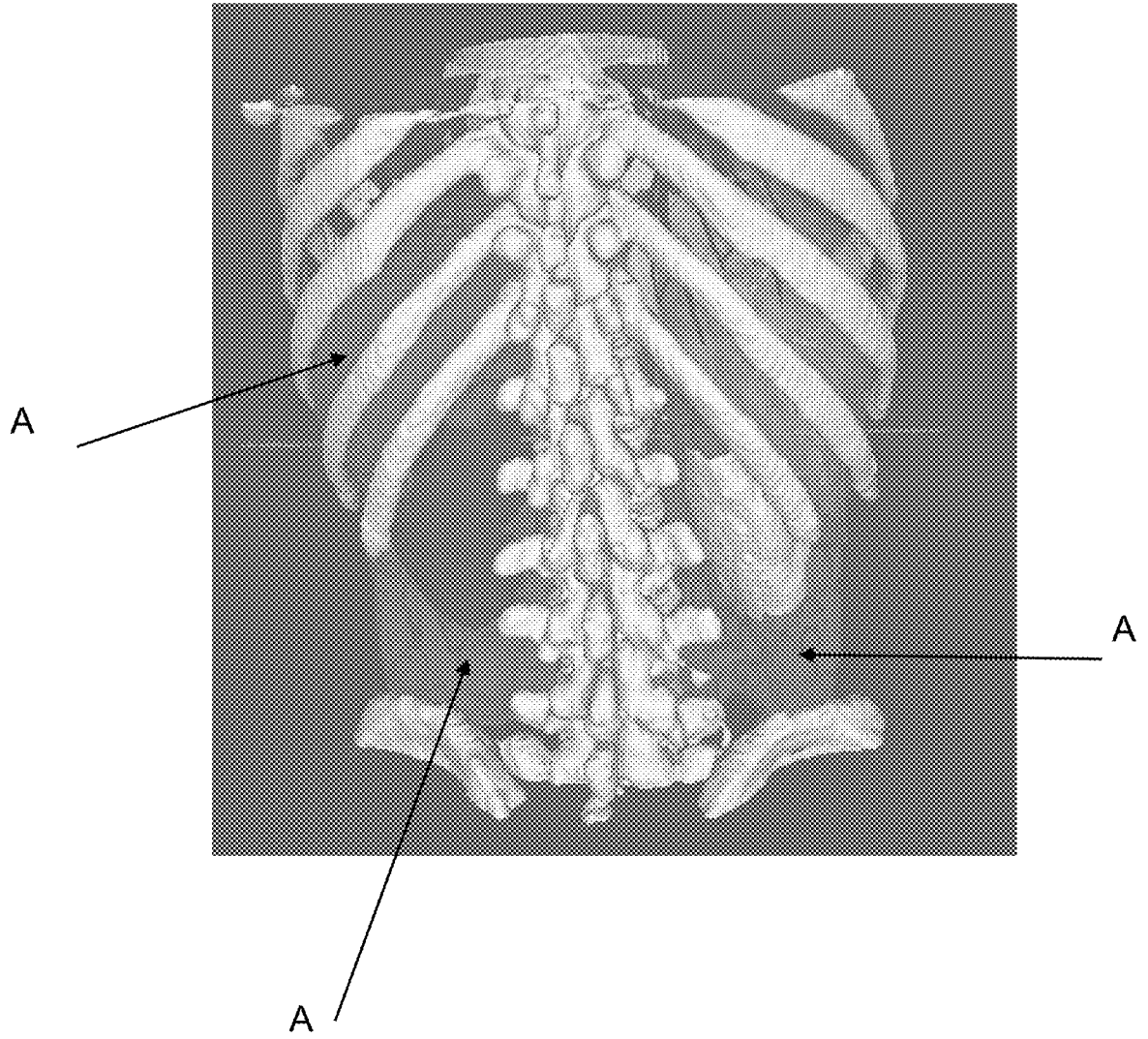
FIG. 7 is a schematic diagram illustrating a region to be avoided in the abdomen according to some embodiments of the present disclosure.
Figure 9:
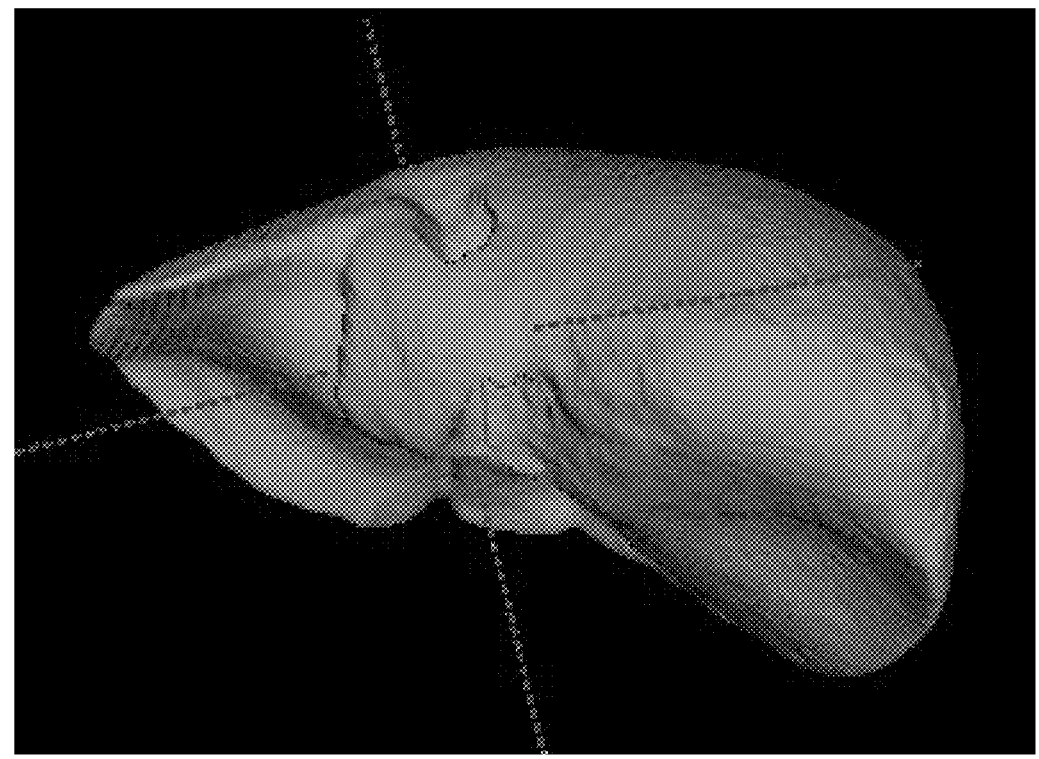
FIG. 9 is a schematic diagram illustrating a liver mask according to some embodiments of the present disclosure.
Figure 11:
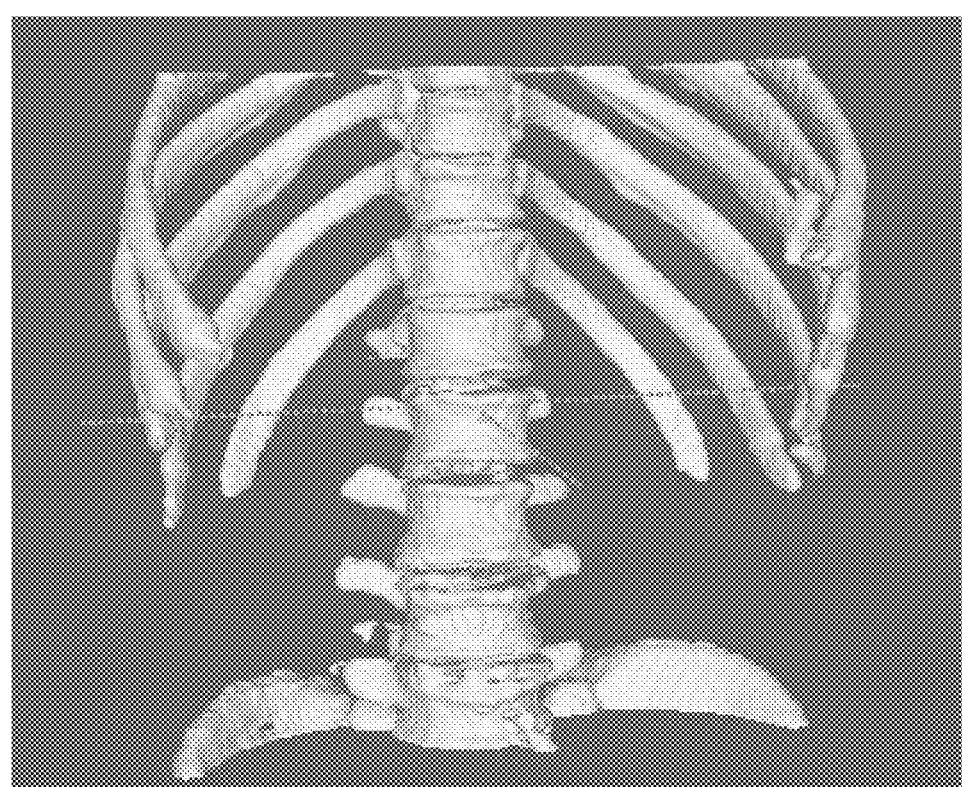
FIG. 11 is a schematic diagram illustrating a skeletal mask according to some embodiments of the present disclosure.

The to-be-intervened object mask refers to a mask of a region to be intervened during the interventional procedure. In some embodiments, a to-be-intervened object may be a target organ. In some embodiments, the to-be-intervened object may include the brain, the liver, the spleen, the kidneys, or any other feasible organs or tissues, e.g., the thyroid, etc. In some embodiments, the to-be-intervened object mask may include a brain mask, a liver mask (e.g., an exemplary liver mask shown in FIG. 9), a spleen mask, a kidney mask, and a thyroid mask. The region to be avoided refers to a region that is not intervenable during the interventional procedure, e.g., an abdominal region to be avoided shown in FIG. 7. In some embodiments, the region to be avoided may be an unpuncturable region. In some embodiments, the region to be avoided may include a vascular region, a heart region, a tracheal region, a lung region, a muscle region, or any other feasible organ or tissue regions, e.g., a skeletal region (e.g., an exemplary skeletal mask in FIG. 11), etc.

In some embodiments, obtaining the overall mask, the predetermined object mask, and the to-be-intervened object mask by segmenting the first medical image in 310 may be implemented as a following process.

The process may include obtaining the overall mask by segmenting the first medical image; obtaining the predetermined object mask by segmenting the predetermined object in the first medical image; and obtaining the to-be-intervened object mask by segmenting the to-be-intervened object in the first medical image.

In some embodiments, the first medical image may include a plain scanned type and/or enhanced type medical scanning image. In some embodiments, the medical scanning image of the target object may be obtained before the medical scanning image is segmented. In some embodiments, image preprocessing may be performed on the obtained medical scanning image. In some embodiments, the image preprocessing may be performed as follows.

The image preprocessing may include obtaining a sampled image by sampling the medical scanning image based on a predetermined sampling interval; obtaining a foreground region of the sampled image by performing a background region removal processing on the sampled image based on a predetermined pixel threshold; and obtaining a processed medical image by performing a pixel value normalization processing on the foreground region of the sampled image.

For example, the predetermined sampling interval may be set to be 2 mm, and the predetermined pixel threshold to be −900. The sampled image may be obtained by sampling the medical scanning image based on the predetermined sampling interval of 2 mm, and then the foreground region of the sampled image may be obtained by removing pixel points in the sampled image with pixel values less than −900 as a background region. Then the processed medical image may be obtained by normalizing each pixel value in the foreground region of the sampled image to a range of [−5.9, 1.3]. A pixel value of the sampled image may be an HU value. The HU value represents a corresponding value of each tissue in the CT image that is equivalent to an X-ray attenuation coefficient. The normalization processing may be performed by a standard deviation normalization method, which is not specifically limited to the embodiments of the present disclosure.

In some embodiments, the overall mask may be obtained by segmenting the first medical image; a fat mask may be obtained by performing fat segmentation on the first medical image; and the to-be-intervened object mask may be obtained by performing organ segmentation on the first medical image. In some embodiments, performing the fat segmentation on the first medical image may include determining pixels in the medical scanning image whose pixel values are within a predetermined pixel value range as target pixels; and then obtaining the fat mask by performing a connection processing on the plurality of target pixels. In some embodiments, performing the organ segmentation on the first medical image may include obtaining the to-be-intervened object mask by segmenting the medical scanning image using a pre-established interventional organ segmentation model.

In some embodiments, when an abdominal scanning image is used as the first medical image, performing the organ segmentation on the abdominal scanning image may include obtaining a to-be-punctured organ mask by segmenting the abdominal scanning image using a pre-established puncture organ segmentation model. A to-be-punctured organ may include at least one of the liver or the kidneys. The puncture organ segmentation model may include at least one of a liver segmentation model or a kidney segmentation model.

In some embodiments, determining the region to be avoided based on the overall mask, the predetermined object mask, and the to-be-intervened object mask in 320 may include determining a target mask based on the overall mask and the predetermined object mask; and obtaining the region to be avoided based on the target mask and the to-be-intervened object mask.

The target mask refers to a predetermined target segmentation result of a non-intervening object mask obtained based on the overall mask and the predetermined object mask. The non-intervening object mask refers to a non-intervening region mask or a predetermined puncture exclusion region mask, e.g., an unpuncturable region mask in the abdominal mask, or the like. In some embodiments, the non-intervening object mask may include an unpuncturable organ mask. In some embodiments, the unpuncturable organ mask may include one or more of a vascular mask, a cardiac mask, a skeletal mask, a lung mask, and a tracheal mask.

In some embodiments, a segmentation method for obtaining the target mask may be determined based on features of a processed image (e.g., size, etc.) selected in the medical scanning image. In some embodiments, taking an abdominal scanning image as an example, if a length of the processed image along a z-axis is less than or equal to a predetermined length limit, a target mask corresponding to the processed image may be obtained by inputting the processed image into an abdominal segmentation model (an example shown in FIG. 12) to perform abdominal segmentation. In some embodiments, if the length of the processed image along the z-axis is greater than the predetermined length limit, the processed image may be segmented into a plurality of sub-processing images along the z-axis direction according to a predetermined step size; intermediate segmentation results corresponding to the plurality of sub-processing images output by the abdominal segmentation model may be obtained by inputting the plurality of sub-processing images into the abdominal segmentation model; and the target mask corresponding to the processed image may be obtained by splicing the intermediate segmentation results of the plurality of sub-processing images.

For example, if the predetermined length limit is set to 80 mm, and the length of the processed image along the z-axis is less than or equal to 80 mm, a target segmentation result corresponding to the processed image may be obtained by inputting the processed image into the abdominal segmentation model. If the length of the processed image along the z-axis is greater than 80 mm, the processed image may be segmented into a plurality of sub-processing images using a predetermined step size of 40 mm. The intermediate segmentation results corresponding to the plurality of sub-processing images outputted by the abdominal segmentation model may be obtained by inputting the plurality of sub-processing images into the abdominal segmentation model; and then the target segmentation result corresponding to the processed image may be obtained by splicing the intermediate segmentation results of the plurality of sub-processing images. The predetermined length limit and the predetermined step size are not specifically limited in the embodiments of the present disclosure.

Figure 12:
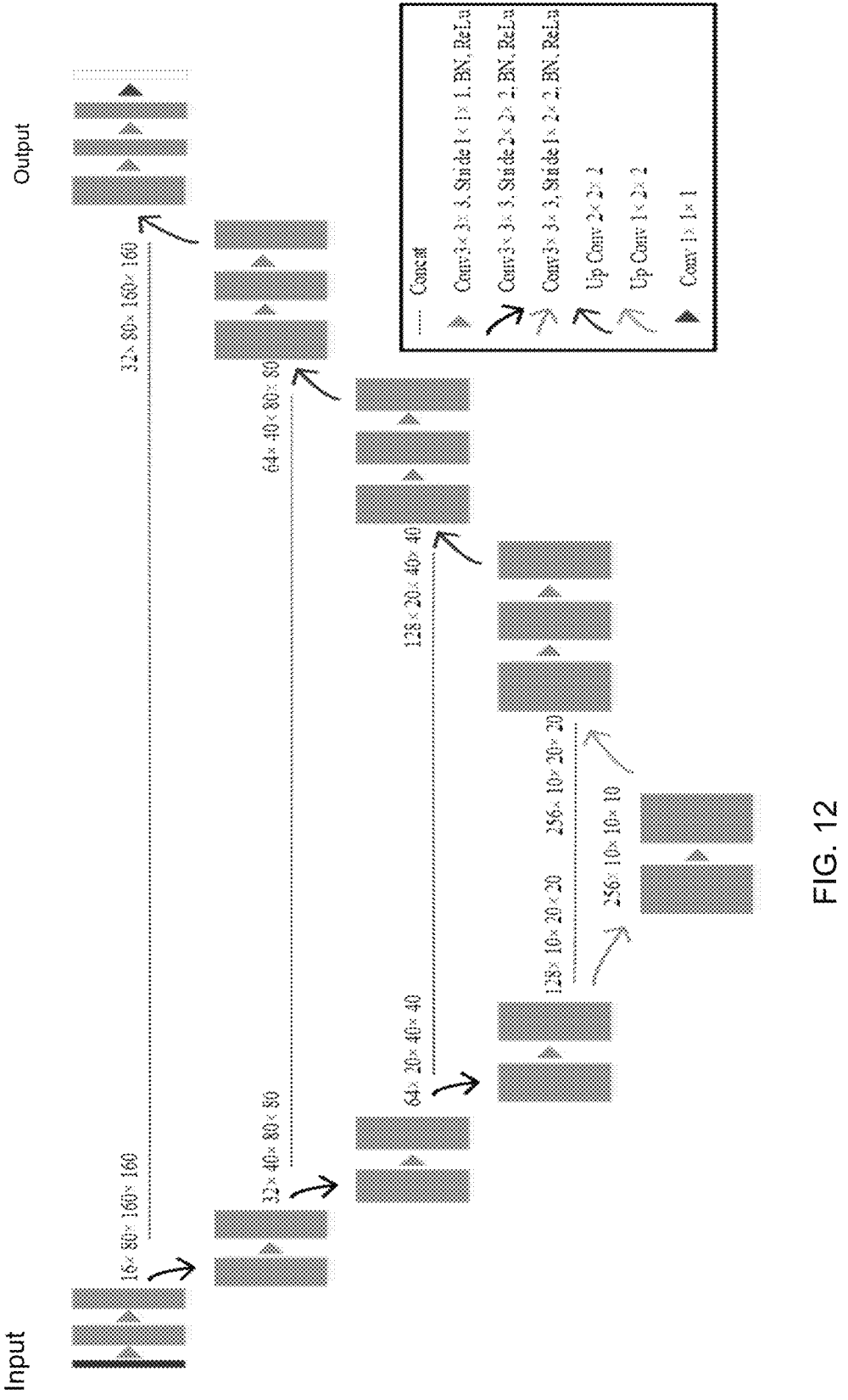
FIG. 12 is a schematic diagram illustrating an abdominal segmentation model according to some embodiments of the present disclosure.

In some embodiments, the abdominal segmentation model shown in FIG. 12, may include a deep convolutional neural network model. During the segmentation process, the abdominal segmentation model may downsample an x-axis, a y-axis, and the z-axis of each sub-processed image. The x-axis and the y-axis may be downsampled a same count of times, while the z-axis may be downsampled fewer times than the x-axis. A specific model structure of the above abdominal segmentation model may be realized in any other feasible structural manners in the prior art, which is not specifically limited to the embodiments of the present disclosure.

In some embodiments, image post-processing may be performed on the processed image based on the target mask. The image post-processing may include obtaining a binarized image by binarizing the processed image based on a predetermined probability threshold and the target mask; and performing a connected component analysis on the binarized image, and determining a largest connected component as the abdominal mask.

In some embodiments, the processed image may be obtained by performing an image preprocessing on the abdominal scanning image; the target mask corresponding to the processed image may be obtained by performing abdominal segmentation on the processed image using the pre-established abdominal segmentation model; and the abdominal mask may be obtained by performing the image post-processing on the processed image based on the target mask.

In some embodiments, determining the target mask based on the overall mask and the predetermined object mask may include obtaining the target mask by subtracting the predetermined object mask from the overall mask; and obtaining the non-intervening object mask by subtracting the to-be-intervened object mask from the target mask.

In some embodiments, in order to improve image pixel consistency (e.g., an image edge region, etc.) during segmentation and obtain a more accurate target mask result, the overall mask and/or the predetermined object mask may be processed before subtracting the predetermined object mask from the overall mask. In some embodiments, processing the overall mask and/or the predetermined object mask may include expanding (i.e., enlarging) the overall mask and/or the predetermined object mask, and/or eroding (i.e., reducing) the overall mask and/or the predetermined object mask.

In some embodiments, taking the abdominal scanning image as an example, after the abdominal mask, the fat mask, and the to-be-punctured organ mask are obtained, the fat mask and the to-be-punctured organ mask may be subtracted from the abdominal mask, thereby obtaining puncture exclusion region (as a region A shown in FIG. 7) inside an abdominal cavity.

In some embodiments, taking the to-be-intervened object mask as a liver mask or a kidney mask as an example, the abdominal scanning image may also include unpuncturable organs such as blood vessels, a portion of the heart, ribs, vertebrae, lungs, trachea, diaphragm, or the like. Therefore, it is necessary to obtain unpuncturable organ masks of these unpuncturable organs.

In some embodiments, the vascular mask may be obtained by inputting the abdominal scanning image into a pre-established vascular segmentation model. In some embodiments, a cardiac mask may be obtained by inputting the abdominal scanning image into a pre-established heart segmentation model. The skeletal mask may be obtained by inputting the abdominal scanning image into a pre-established skeletal segmentation model. It should be noted that the unpuncturable organ masks may also be obtained in any other feasible manner, which is not specifically limited in the embodiments of the present disclosure.

In some embodiments, the connected component analysis may be performed on the obtained non-intervening object mask, and a connected component satisfying a first predetermined condition may be determined as the region to be avoided.

The first predetermined condition refers to a condition that is satisfied when the region to be avoided is determined through the connected component analysis. In some embodiments, the first predetermined condition may include that an area of the connected component is within a predetermined area threshold. For example, the first predetermined condition may be that the area of the connected component is greater than the predetermined area threshold. In some embodiments, the first predetermined condition may include that the area of the connected component ranks at a top position in the ranking of areas of all connected components. For example, if the areas of all connected components are ranked in descending order, the area of the connected component may rank top three.

For example, taking the abdominal scanning image as an example, after the connected component analysis is performed on the unpuncturable organ mask inside the abdominal cavity, six connected components may be obtained. If areas of a connected component 2 and a connected component 5 are larger than the predetermined area threshold, the connected component 2 and the connected component 5 may be determined as puncture exclusion regions inside the abdominal cavity. Alternatively, if the areas of the six connected components are ranked in descending order, and a connected component 1, a connected component 3, and a connected component 6 rank top three, the connected component 1, the connected component 3, and the connected component 6 may be determined as the puncture exclusion regions inside the abdominal cavity.

In some embodiments, the to-be-avoided object mask may be obtained by segmenting the medical image. The connected component analysis may be performed on the to-be-avoided object mask, and the connected component satisfying the first predetermined condition may be determined as the region to be avoided.

The to-be-avoided object mask refers to a mask of the region to be avoided. In some embodiments, a to-be-avoided object mask may include a vascular mask, a cardiac mask, a tracheal mask, a lung mask, a muscle mask, or any other feasible organ or tissue mask, such as a skeletal mask (e.g., an exemplary skeletal mask shown in FIG. 11), etc.

In some embodiments, after the non-intervening object mask and the connected component satisfying the first predetermined condition are obtained, a union set of the non-intervening object mask and the connected component may be calculated, and the calculated union set may be determined as the region to be avoided. In some embodiments, after the unpuncturable organ mask and the puncture exclusion region inside the abdominal cavity are obtained, a union set of the unpuncturable organ mask and the puncture exclusion region inside the abdominal cavity may be calculated, and the calculated union set may be the puncture exclusion region in the abdominal scanning image.

In summary, the region to be avoided in the first medical image can be obtained relatively easily through the above analysis and determination method of the region to be avoided, thereby reducing the planning difficulty of pathway planning and improving the efficiency of pathway planning.

It should be noted that the descriptions of process 300 are intended to be exemplary and illustrative only, and do not limit the scope of application of the present disclosure. For those skilled in the art, various corrections and changes may be made to process 300 under the guidance of the present disclosure. However, these corrections and changes remain within the scope of the present disclosure. For example, the selection of the to-be-intervened object of the to-be-intervened object mask may vary according to a specific lesion condition.

In some embodiments, obtaining, by the image segmentation module 210, the first segmented image by performing image segmentation on the first medical image may be implemented in the following operations including determining the target medical image by performing a registration using finite elements based on the first segmented image. In some embodiments, the target medical image may be obtained by performing the registration using a mechanical model constructed based on the finite elements.

The finite elements refer to various solution methods using finite element theory. In some embodiments, the finite elements may be a finite element method (FEM). In some embodiments, the finite element method may be implemented using calculation manners such as object discretization, selection of displacement modes, analysis of mechanical properties, equivalent node forces, and finite integration methods. In some embodiments, the finite element method may also be implemented using any other feasible calculation manners, e.g., boundary element analysis, etc. The target medical image refers to a target image that is expected to be obtained after the registration is performed on the first segmented image.

In some embodiments, as shown in FIG. 13, a process 400 may be implemented by the surgical pathway processing system 100 (e.g., the processing device 140 of the surgical pathway processing system 100) or the surgical pathway processing system 200. For example, the process 400 may be stored in a storage device (e.g., the storage device 150 or a storage unit of the system) in the form of a program or an instruction, and the process 400 may be implemented when a processor (e.g., the processing device 140) or modules of FIG. 2 execute(s) the program or the instruction.

In some embodiments, the process 400 of performing the registration using the finite elements may include the following operations.

In 410, a second medical image of a target object may be obtained, the second medical image and the first medical image including images of the target object at different periods.

In 420, a second segmented image may be obtained by segmenting at least a portion of the second medical image.

In 430, a rigid registration result may be obtained by performing a rigid registration on the target object in the first segmented image and the target object in the second segmented image.

In 440, an elastic registration result may be obtained by performing an elastic registration on the target object in the rigid registration result and the target object in the second segmented image.

In 450, the target medical image may be obtained by processing the first segmented image based on the rigid registration result and the elastic registration result. The second medical image refers to a reference image that is referenced when registering the first medical image. In some embodiments, the second medical image and the first medical image may include the images of the target object at different periods, e.g., images obtained from a same patient during different scans. In some embodiments, the first medical image and the second medical image may include a target organ or tissue of a same object at different time periods, e.g., the first medical image and the second medical image may be different types of image data of a certain organ of the same patient collected at different periods. In some embodiments, the first medical image may be enhanced type image data, and the second medical image may be plain scanned type image data.

In some embodiments, the target object may be the target organ or tissue. In some embodiments, the first medical image and the second medical image may be regional images or slice images corresponding to the target organ/tissue at different periods, and images of arbitrary modality (e.g., CT, MR, ultrasound, etc.) scanned at different periods.

In some embodiments, in 410, the enhanced image data and the plain scanned image data (i.e., the first medical image and the second medical image) corresponding to the same target object may be obtained by performing enhanced scanning and plain scanning in advance on the same target object.

In some embodiments, in 410, a local mesh refinement processing may also be performed. In some embodiments, the local mesh refinement processing may be performed in the following manner: the local mesh refinement processing may be performed on a finite element body mesh.

The second segmented image refers to a segmented image obtained by segmenting the second medical image. In some embodiments, in 420, the second segmented image may be obtained by performing segmentation on at least a portion of the second medical image. In some embodiments, the at least a portion of the second medical image may include a region of interest of the second medical image. In some embodiments, the second segmented image may be obtained by segmenting an entire portion of the second medical image. In some embodiments, a specific segmentation method for obtaining the second segmented image may be found in the specific description regarding the segmentation method of the first medical image in the present disclosure, as described in FIGS. 3-12, which is not repeated here.

In some embodiments, the rigid registration result may include a rigid transformation matrix and an image after the rigid registration. The rigid transformation matrix represents a distance that each point on the target organ moves when a location of the target organ in the first segmented image is moved to a location of the target organ in the second segmented image during the rigid registration process.

In some embodiments, in 430, obtaining the rigid registration result by performing the rigid registration on the target object in the first segmented image and the target object in the second segmented image may be implemented as follows.

The target organ in the first segmented image may be horizontally moved, vertically moved, or deflected. The target organ in the second segmented image may be horizontally moved, vertically moved, or deflected based on the location of the moved or deflected target organ in the first segmented image. In some embodiments, when the first segmented image and the second segmented image are obtained, the rigid registration on the target organ in the first segmented image and the target organ in the second segmented image may be performed to obtain the rigid transformation matrix and the image after the rigid registration. In some embodiments, during the rigid registration process, the target organ in the first segmented image may be translated, deflected, or subjected to other operations in different directions with the location of the target organ in the second segmented image as a reference, so that the location of the target organ in the first segmented image may be aligned with the location of the target organ in the second segmented image. In some embodiments, the target organ in the second segmented image may also be translated, deflected, or subjected to other operations in different directions with the location of the target organ in the first segmented image as a reference, so that the location of the target organ in the second segmented image may be aligned with the location of the target organ in the first segmented image.

In some embodiments, in 440, obtaining the elastic registration result by performing the elastic registration on the target object in the rigid registration result and the target object in the second segmented image may be implemented as follows.

When the rigid registration result is obtained, the image after the rigid registration may be obtained. Further, the elastic registration may be performed on the target organ in the image after the rigid registration and the target organ in the second segmented image to obtain the elastic registration result including the image after the elastic registration. In some embodiments, during the elastic registration process, the elastic registration result of the image after the elastic registration may include registration results of surface feature points on the target organ in the image after the rigid registration and registration results of internal points obtained by finite element modeling solution.

In some embodiments, in 450, obtaining the target medical image by processing the first segmented image based on the rigid registration result and the elastic registration result may be implemented as follows.

After the rigid registration result and the elastic registration result are obtained, the rigid registration result includes a transformation relationship of the location of the target organ in a transformation process of the target organ from the target organ in the first segmented image to the target organ in the second segmented image, and the elastic registration result includes a transformation relationship of the surface feature points of the target organ from the target organ in the first segmented image to the target organ in the second segmented image. Therefore, a transformation relationship of the feature points inside the target organ from the target organ in the first segmented image to the target organ in the second segmented image may be obtained by analyzing the transformation relationship of the target organ in the rigid registration result and the elastic registration result. The feature points on the target organ in the first segmented image may be transformed based on the transformation relationship, and a transformed image may be determined as a registered image, thereby achieving registration of rich information in the first segmented image to the second segmented image.

It should be noted that the descriptions of the process 400 are intended for purposes of illustration and explanation only, and do not limit the scope of the present disclosure. For those skilled in the art, various modifications and changes may be made to the process 400 under the guidance of the present disclosure. However, such modifications and changes remain within the scope of the present disclosure.

Figure 14:
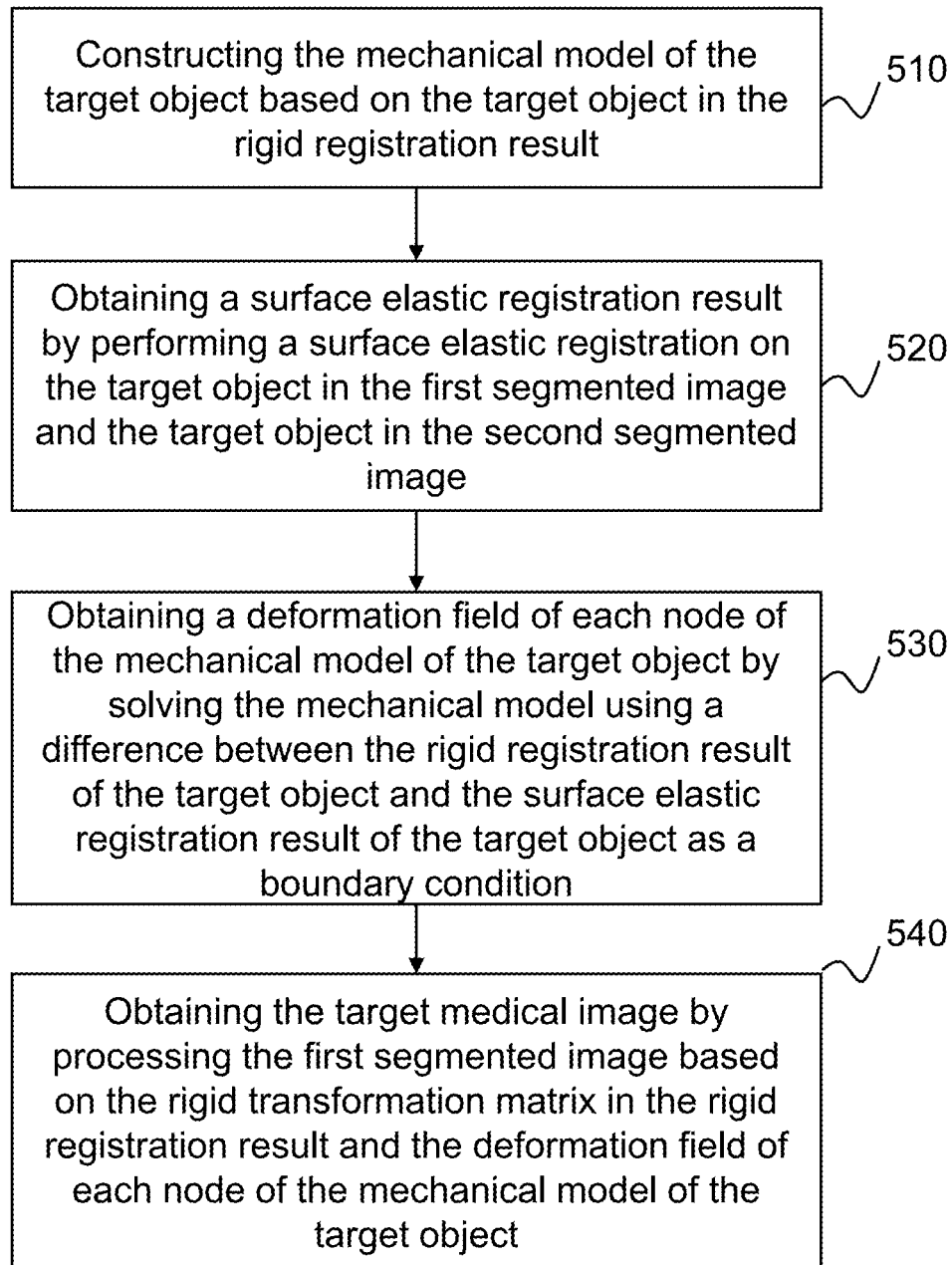
FIG. 14 is a flowchart illustrating an exemplary process for obtaining a target medical image based on a mechanical model according to some embodiments of the present disclosure.

In some embodiments, as shown in FIG. 14, a process 500 may be implemented by the surgical pathway processing system 100 (e.g., the processing device 140 of the surgical pathway processing system 100) or the surgical pathway processing system 200. For example, the process 500 may be stored in a storage device (e.g., the storage device 150, a storage unit of the system) as a program or an instruction, and the process 500 may be implemented when a processor (e.g., the processing device 140) or modules of FIG. 2 executes/execute the program or the instruction.

In some embodiments, the process 500 of obtaining a target medical image based on a mechanical model may be implemented as follows.

In 510, the mechanical model of the target object may be constructed based on the target object in the rigid registration result.

In some embodiments, the mechanical model may be a mechanical model constructed based on the finite element method. In some embodiments, the mechanical model of the target organ may be constructed in simulation software using a corresponding mechanical model construction algorithm. In some embodiments, after the rigid registration result is obtained, the mechanical model of the target organ may be constructed in the simulation software based on an approximate contour, volume data, etc., of the target organ in the obtained first segmented image. In some embodiments, the simulation software may adopt biomechanical simulation software FeBio. In some embodiments, a finite element body mesh structure of the mechanical model may be constructed by performing the local mesh refinement processing on a key region of interest, thereby creating a more accurate mechanical model. For example, when a registration accuracy criterion of intra-hepatic vessels is of primary concern, the local mesh refinement processing may be performed on the key region of interest of a distribution of blood vessels in the liver, thereby increasing the accuracy of solving the mechanical model.

In 520, a surface elastic registration result may be obtained by performing a surface elastic registration on the target object in the first segmented image and the target object in the second segmented image.

In some embodiments, operation 520 may be implemented as follows.

After an approximate registration location of a target organ to be registered is obtained through the rigid registration, a registration location of the surface feature points of the target organ to be registered may be obtained through the surface elastic registration. Then the transformation relationship between the feature points inside the target organ to be registered in the first segmented image and the second segmented image may be calculated by a finite element solution based on the approximate registration location of the target organ and the registration location of the surface feature points. Then the registration may be performed on a first medical image to be registered based on the transformation relationship, so that the rich information of the target organ included in the first segmented image may be registered to the second segmented image, and the registration may be performed based on the transformation relationship of the feature points inside the target organ.

In 530, a deformation field of each node of the mechanical model of the target object may be obtained by solving the mechanical model using a difference between the rigid registration result of the target object and the surface elastic registration result of the target object as a boundary condition.

The boundary condition refers to a solution condition for obtaining the mechanical model based on the rigid registration result and the surface elastic registration result. In some embodiments, when the rigid registration result and the elastic registration result are obtained, the rigid registration result may be that approximate locations of points on the target organ are matched, and the elastic registration result may be that approximate locations of points on a surface of the target organ are matched. The difference between the elastic registration result and the rigid registration result may reflect a location change relationship of the points on the surface of the target organ. Therefore, the difference between the rigid registration result of the target object and the surface elastic registration result of the target object may be selected as the boundary condition. In some embodiments, the difference between the rigid registration result of the target organ and the surface elastic registration result of the target organ may be selected as the boundary condition. In some embodiments, the boundary condition may be set using any other feasible ways, which are not specifically limited in the embodiments of the present disclosure.

In some embodiments, the difference between the elastic registration result and the rigid registration result is used as the boundary condition, and then the deformation field of each point on the target organ may be obtained by solving the mechanical model of the target organ in combination with material parameters. In some embodiments, different materials may be selected based on different mechanical models.

In 540, the target medical image may be obtained by processing the first segmented image based on the rigid transformation matrix in the rigid registration result and the deformation field of each node of the mechanical model of the target object.

In some embodiments, when the rigid transformation matrix in the rigid registration result and the deformation field of each point on the target organ are obtained, a preliminary registered image may be obtained by performing a coarse registration on each point on the target organ in the first segmented image based on the rigid transformation matrix, then a detailed registration may be performed on the internal points of the target organ in the preliminary registered image based on the deformation field of each point in the target organ, and finally a registered target medical image may be obtained.

In some embodiments, a transformed first segmented image may be obtained by performing a translation and/or rotation on the first segmented image based on the rigid transformation matrix; and the target medical image may be obtained by performing a translation and/or rotation on each node of the mechanical model of the target object in the transformed first segmented image based on the deformation field of each node of the mechanical model of the target object.

In some embodiments, a deformation field of each pixel point in the target object may be obtained by performing an interpolation processing based on the deformation field of each node of the mechanical model of the target object; and the target medical image may be obtained by performing translation on each pixel point in the target object in the transformed first medical image based on the deformation field of each pixel point in the target object.

A third medical image refers to an input image for obtaining the second medical image through network transformation. In some embodiments, the third medical image may be enhanced type image data (e.g., an enhanced image), and the second medical image may be plain scanned type image data (e.g., a plain scanned image). In some embodiments, the second medical image may also be other types of image data, and the third medical image may also be other types of image data, as long as the second medical image and the third medical image include a same scanning object.

In some embodiments, the enhanced image data and the plain scanned image data (i.e., the third medical image and the second medical image) corresponding to the same object may be obtained by performing enhanced scanning and plain scanning in advance on the same target object. For example, the third medical image may be obtained by obtaining enhanced image data of thoracic and abdominal regions of a patient before the surgery, and the second medical image may be obtained by obtaining plain scanned image data of the thoracic and abdominal regions of the patient during the surgery. In some embodiments, image data of a target organ of a same patient at different periods may also be obtained by other means.

In some embodiments, the second medical image may be obtained by performing a removing highlighted information processing on the third medical image; and/or the second medical image may be obtained by inputting the third medical image into a predetermined image transformation network.

In some embodiments, highlighted locations of internal details of the target organ of a segmented mask image in an original enhanced image may be determined by segmenting the internal details (e.g., blood vessels, tumors) of the target organ through the enhanced image (the third medical image). Further, pixel values of non-contrast highlighted regions within a certain range around the highlighted locations may be uniformly assigned to the highlighted locations to remove highlighted information in the enhanced image, thereby generating the plain scanned image (i.e., the second medical image) based on the enhanced image.

In some embodiments, the plain scanned image may be generated through simulation by removing angiographic highlighted information in the third medical image using a predetermined algorithm. The predetermined algorithm may be that a model may be trained by learning a large number of plain scanned images through a generative adversarial network. When the third medical image is inputted, the adversarial network may output a plain scanned image (i.e., the second medical image) corresponding to the third medical image.

In some embodiments, images of different phases may be obtained in advance, and then a fused image, i.e., the second medical image, may be obtained by fusing the images of different phases.

In some embodiments, a third mask image corresponding to the third medical image may be obtained by extracting the target object and an internal detail mask from the third medical image; and the target medical image may be verified based on the third mask image. In some embodiments, the internal detail mask may be a key anatomical structure or tissue of a key region of interest in the target object. For example, when the target object is a liver, in a certain specific scenario, key internal structures such as arteriovenous vessels and tumors in the liver may be determined as the internal detail mask.

In some embodiments, the third medical image may be an enhanced type image. In some embodiments, the internal details of the third medical image may be some detailed tissues in an object to be detected (e.g., a target organ, etc.). For example, if the object to be detected is a lung tissue or organ, the internal details may include pulmonary artery blood vessels, lesion sites, etc. In some embodiments, the third medical image may be obtained, and the third mask image corresponding to the third medical image may be obtained by extracting the target organ and the internal detail mask from the third medical image using the mask processing algorithm, thereby performing subsequent verification and registration using the third mask image.

In some embodiments, the registered target medical image may be verified using the third mask image. In some embodiments, after the registered target medical image is obtained, the registered image may be further verified using the third mask image corresponding to the third medical image. Since the registered image is an image obtained through the registration of the first medical image and the second medical image, and the second medical image is an image obtained by performing image transformation on the third medical image, the third mask image corresponding to the third medical image may be obtained by performing a masking processing on the third medical image, and then the registered image may be verified using the third mask image, thereby effectively and accurately verifying the feasibility and accuracy of the previous registration process.

It should be noted that the foregoing descriptions of the process 500 are intended to be exemplary and illustrative only and do not limit the scope of application of the present disclosure. For those skilled in the art, various corrections and changes may be made to the process 500 under the guidance of the present disclosure. However, these corrections and changes remain within the scope of the present disclosure.

Figure 15:
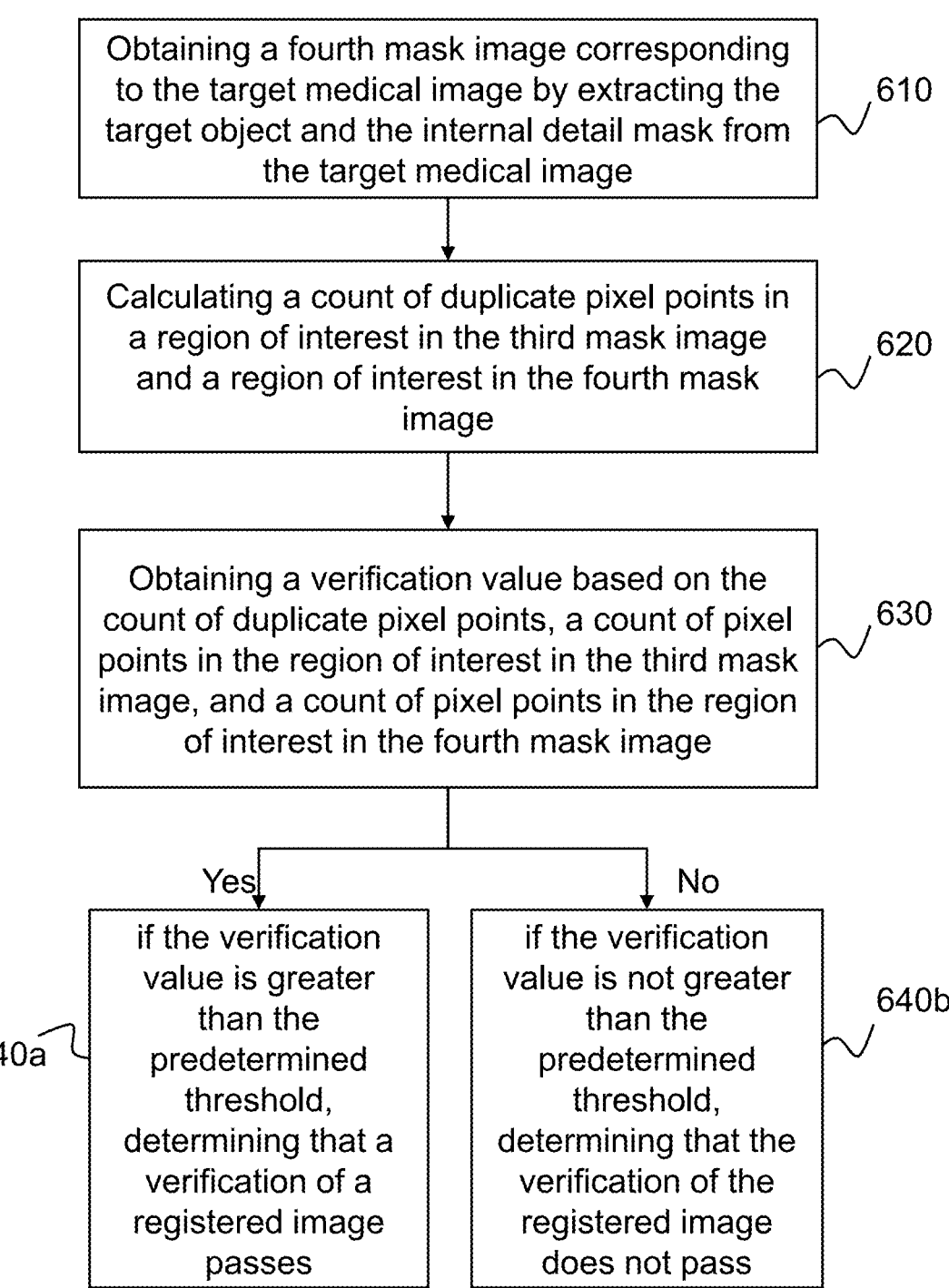
FIG. 15 is a flowchart illustrating an exemplary process for verifying a registered target medical image according to some embodiments of the present disclosure.

In some embodiments, as shown in FIG. 15, a process 600 may be implemented by the surgical pathway processing system 100 (e.g., the processing device 140 of the surgical pathway processing system 100) or by the surgical pathway processing system 200. For example, the process 600 may be stored in a storage device (e.g., the storage device 150, and a storage unit of the system) in the form of a program or an instruction, and the process 600 may be implemented when a processor (e.g., the processing device 140) or modules of FIG. 2 executes/execute the program or the instruction.

In some embodiments, the process 600 of verifying a registered target medical image may be implemented as follows.

In 610, a fourth mask image corresponding to the target medical image may be obtained by extracting the target object and the internal detail mask from the target medical image.

In some embodiments, the fourth mask image corresponding to the target medical image may be obtained by extracting the target object and the internal detail mask from the target medical image in a similar manner as that of extracting the target object and the internal detail mask from the third medical image. In some embodiments, the extraction process may be implemented in any other feasible ways, which are not specifically limited in the embodiments of the present disclosure.

In 620, a count of duplicate pixel points in a region of interest in the third mask image and a region of interest in the fourth mask image may be calculated.

The region of interest refers to a region where the target object is located. In some embodiments, the region of interest may be a region where the target organ is located. In some embodiments, after the third mask image and the fourth mask image are obtained, the fourth mask image may be verified. In some embodiments, a location of each pixel point in the region where the target organ is located in the third mask image may be compared with a location of each pixel point in the region where the target organ is located in the fourth mask image, and pixel points with consistent locations may be determined as duplicate pixel points, thereby determining the count of duplicate pixel points in the region of interest in the third mask image and the region of interest in the fourth mask image.

In 630, a verification value may be obtained based on the count of duplicate pixel points, a count of pixel points in the region of interest in the third mask image, and a count of pixel points in the region of interest in the fourth mask image. In some embodiments, after the verification value is obtained, whether the verification value is greater than a predetermined threshold may be determined. If the verification value is greater than the predetermined threshold, operation 640a may be implemented; and if the verification value is not greater than the predetermined threshold, operation 640b may be implemented.

In 640a, if the verification value is greater than the predetermined threshold, it may be determined that a verification of a registered image passes.

In 640b, if the verification value is not greater than the predetermined threshold, it may be determined that the verification of the registered image does not pass.

In some embodiments, a count of duplicate pixel points in a region where the target organ is located in the third mask image and a region where the target organ is located in the fourth mask image, a count of pixel points in the region where the target organ is located in the third mask image, and a count of pixel points in the region where the target organ is located in the fourth mask image be calculated. In some embodiments, the verification value may be obtained using the following formula (1).

$$Y=2\times N_c/N_a+N_b \qquad (1),$$

where $N_c$ denotes the count of duplicate pixel points in the region where the target organ is located in the third mask image and the region where the target organ is located in the fourth mask image; $N_a$ denotes the count of pixel points in the region where the target organ is located in the third mask image; $N_b$ denotes the count of pixel points in the region where the target organ is located in the fourth mask image; and Y denotes the verification value.

In some embodiments, the predetermined threshold may be configured to measure a matching degree between the third mask image and the fourth mask image, which may be determined based on actual matching requirements. In some embodiments, the verification value may be compared with the predetermined threshold. If the verification value is greater than the predetermined threshold, it means that the count of duplicate pixel points in the region where the target organ is located in the third mask image and the region where the target organ is located in the fourth mask image is high. In other words, the matching degree between the third mask image and the registered image is high, indicating that the registration method is feasible or the registration result is accurate. Therefore, the verification of the registered image may be determined to pass in this case. If the verification value is not greater than the predetermined threshold, it means that the count of duplicate pixel points in the region where the target organ is located in the third mask image and the region where the target organ is located in the fourth mask image is low. In other words, the matching degree between the third mask image and the registered image is low, indicating that the registration method is not feasible, or an error in a certain part of the registration process results in an inaccurate registered image. In this case, it may be determined that the verification of the registered image does not pass. In some embodiments, if the verification does not pass, it is possible to go back to the steps in the previous registration method, check the possible errors in the steps, and make adjustments or corrections. Then, the first medical image and the second medical image may be registered again based on the adjusted or corrected steps until the verification passes. In some embodiments, finite element registration parameters of the mechanical model may be optimized based on a feedback result of the verification (pass or not pass). For example, when the feedback result is passed, the registration data may be stored for subsequent construction or optimization of the mechanical model, and when the feedback result is not passed, the parameters of the mechanical model may be adjusted.

In summary, the registration result may be verified on the basis of the registration being completed to verify the feasibility of the registration method or the accuracy of the registration result, thereby providing a reliable and accurate registration method for practical application of the registration method to specific clinical medicine, such as the registration process of preoperative enhanced images and intraoperative plain scanned images, to improve the efficiency and success rate of surgery.

It should be noted that the descriptions of the process 600 above are for illustration and explanation purposes only, and do not limit the scope of application of the present disclosure. For those skilled in the art, various modifications and changes may be made to the process 600 under the guidance of the present disclosure. However, such modifications and changes are still within the scope of the present disclosure.

Figure 16:
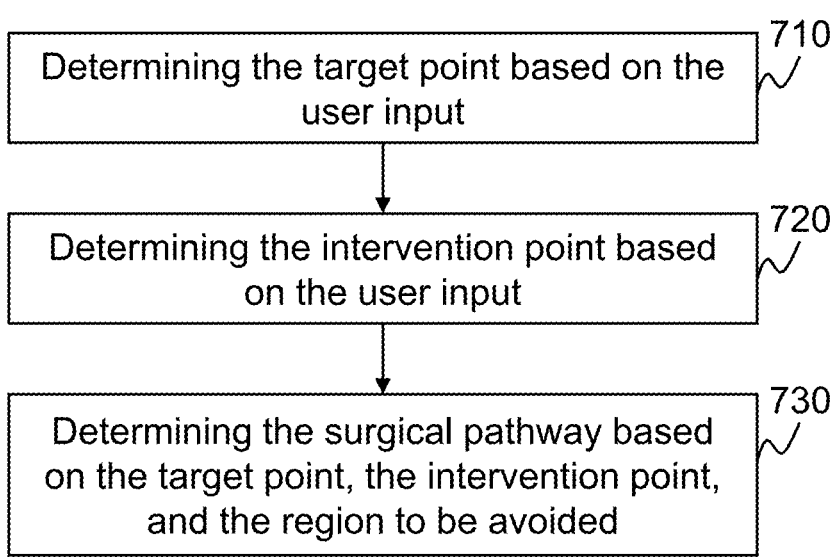
FIG. 16 is a flowchart illustrating an exemplary process for determining a surgical pathway according to some embodiments of the present disclosure.

In some embodiments, as shown in FIG. 16, the pathway planning module 230 may be configured to automatically determine a target point and an intervention point based on a user input, and determine a surgical pathway based on the target point, the intervention point, and a region to be avoided.

In some embodiments, the pathway planning module 230 may further include a target point determination unit, an intervention point determination unit, a pathway determination unit, and a pathway verification unit (not shown in the figure).

The target point determination unit may be configured to determine the target point. For example, the target point determination unit may receive a first operation of a user on a first segmented image, and determine the target point in response to the first operation.

The intervention point determination unit may be configured to determine the intervention point. For example, the intervention point determination unit may receive a second operation of the user on the first segmented image, determine a reference pathway in response to the second operation, and determine the intervention point based on the reference pathway.

The pathway determination unit may be configured to determine a candidate pathway and the surgical pathway. For example, the pathway determination unit may determine the candidate pathway based on the reference pathway. As another example, the pathway determination unit may determine the candidate pathway based on the target point and the intervention point. As yet another example, the pathway determination unit may determine the surgical pathway based on a verification result of the candidate pathway. As yet another example, the pathway determination unit may determine the surgical pathway based on the target point, the intervention point, the region to be avoided, and a distance threshold.

The pathway verification unit may be configured to verify the candidate pathway or the surgical pathway. For example, the pathway verification unit may determine whether the candidate pathway or the surgical pathway includes an interference feature, and/or whether intervention parameters of the pathway satisfy a second predetermined condition.

In some embodiments, as shown in FIG. 16, a process 700 may be implemented by the surgical pathway processing system 100 (e.g., the processing device 140 of the surgical pathway processing system 100) or the surgical pathway processing system 200 (e.g., the pathway planning module 230). For example, the process 700 may be stored in a storage device (e.g., storage device 150, and a storage unit of the system) in the form of a program or an instruction, and the process 700 may be implemented when the processor (e.g., the processing device 140) or modules of FIG. 2 executes/execute the program or the instruction.

In 710, the target point may be determined based on the user input.

In some embodiments, the user may include staff who are required to verify the surgical pathway, e.g., medical personnel. In some embodiments, the user may include other personnel associated with the surgical pathway, e.g., a puncture object, or a device operator, etc., which is not limited in the present disclosure.

The target point refers to a puncture endpoint of the surgical pathway. In some embodiments, the target point may reflect a location of a target organ (e.g., the object to be intervened) on a target image (e.g., the first medical image, the second medical image, the first segmented image, the second segmented image, the target medical image, etc.).

In some embodiments, the target point may be determined based on the target image.

In some embodiments, the target image may include a tissue segmented image (e.g., the first segmented image, the second segmented image, the target medical image, etc.) which is obtained through tissue segmentation and is capable of distinguishing a location of a lesion (or the location of the target organ) from human tissues and organs (e.g., blood vessels, nerves, bones, etc.), and a skin contour.

Skin acts as a barrier between a human body and an external environment. There is a significant grayscale difference between subcutaneous tissues of the human body and the external air, and there are also differences between human tissues and devices. Merely by way of example, noise may be filtered by performing a Gaussian filtering processing on an obtained scanning image (e.g., a magnetic resonance image, a CT image, etc.) to enhance the accuracy of subsequent processing. Then an initial medical image may be obtained by removing a background in the noise-filtered image by selecting an appropriate threshold based on grayscale features of the human tissues. Further, a maximum connected component analysis may be performed on the initial medical image, only a region where a maximum connected component is located is retained, and a hole filling is performed on the region where the maximum connected component is located to obtain subcutaneous tissues of the human body. Subsequently, the skin contour (e.g., an overall mask) may be obtained by performing boundary extraction on the subcutaneous tissues. Further, lesions (e.g., the pre-determined object mask), human tissues, and organs in the image may be segmented using methods such as deep learning. Finally, the human tissues, the organs, and the lesions in the image may be marked using different marker values, thereby facilitating distinction of the human tissues, the organs, and the lesions in the target image. For example, as shown in FIG. 22, regions of different shapes may correspond to different tissues or organs.

In some embodiments, the target image may include a tissue segmented image (e.g., the target medical image) after registration. More details regarding the registration may be found elsewhere in the present disclosure (e.g., FIG. 3 and related descriptions thereof).

In some embodiments, the target image may also include a raw image that is not subjected to tissue segmentation, such as a scanned image (e.g., the first medical image, and the second medical image) obtained by a medical device, or a scanned image processed by image enhancement, noise reduction, which are not limited in the embodiments of the present disclosure.

In some embodiments, the target image may include a 2D image, a 3D image, or a 4D image.

In some embodiments, the first operation of the user on the target image (e.g., the first segmented image, the second segmented image, the target medical image, etc.) may be received, and the target point may be determined in response to the first operation.

In some embodiments, the first operation may include a click operation. For example, when a display of a terminal device/computer device is a touch display type, the first operation refers to a click operation of the user on the first segmented image on the touch display using a finger/touch tool, etc. As another example, when the display of the terminal device/computer device is not the touch display type, the first operation refers to a click operation of the user on the first segmented image on the display using a mouse.

In some embodiments, the first operation may be a gesture operation, an expression operation, a voice operation, etc., which are not limited to the present disclosure.

In some embodiments, a location corresponding to the first operation on the target image may be determined as the target point based on the first operation of the user on the target image. For example, a button T representing the target point may be provided on a display interface. The user may move the T point to a specific slice of the CT image in the display interface and then click on the image. The processing device may determine a current location of the T point as the location (e.g., $T_1$ or $T_2$ in FIG. 22(b)) of the target point based on the click operation of the user.

In some embodiments, an action point of the first operation on the target image may be determined, and the target point may be determined based on the action point. For example, when the first operation of the user on the first segmented image on the touch display is received, a location on the first segmented image that the user clicks may be determined as the action point, and the action point may be determined as the target point. As another example, when the first operation of the user on the target medical image on a non-touch display using the mouse is received, a location of a cursor on the target medical image may be determined as the action point, and the action point may be determined as the target point.

In some embodiments, the target point may be verified after the target point is determined. In some embodiments, the target point may be verified by determining whether the target point is within a lesion region and/or a subcutaneous tissue (e.g., the overall mask) of the human body. For example, as shown in FIG. 22(b), if the user drags the T point to a location of $T_2$, the system may verify the $T_2$ point, and determine whether the $T_2$ point is within a lesion mask (e.g., the to-be-intervened object mask) on the first segmented image. If there is no lesion mask, the system may determine whether the $T_2$ point is within a human body mask (e.g., the overall mask) on the first segmented image. If the $T_2$ point is within the lesion mask or the human body mask, the $T_2$ point may be determined as the target point. If the $T_2$ point is not within the lesion mask or the human body mask, the system may prompt the user or automatically change the location of the target point (e.g., determine the location of the $T_1$ point as the target point). By verifying the target point, the correctness and feasibility of the target point determined by the user may be guaranteed, thus ensuring the correctness and rationality of the determined surgical pathway.

In some embodiments, the target point may be determined in other ways. For example, a center of volume/a center of gravity of the target organ may be determined as the target point based on the target image, which is not limited to the present disclosure.

In 720, the intervention point may be determined based on the user input.

The intervention point refers to a puncture starting point of the surgical pathway, also known as a needle entry point. In some embodiments, the intervention point may reflect a location of a needle tip of a puncture device (e.g., an ablation needle, and a puncture needle) on the target image (e.g., the first segmented image, the second segmented image, and target medical image, etc.). In some embodiments, the intervention point may include a point located on a human skin interface.

In some embodiments, the intervention point may be determined based on the target point and the target image. In some embodiments, the intervention point may be determined based on the target point and the region to be avoided.

In some embodiments, an intervention point may be determined based on the target point and the second operation of the user. In some embodiments, a reference pathway may be determined in response to the second operation of the user, and the intervention point may be determined based on the reference pathway. More details regarding the determination of the intervention point may be found in FIG. 17 and its related descriptions, which are not repeated here.

In 730, the surgical pathway may be determined based on the target point, the intervention point, and the region to be avoided.

In some embodiments, a tissue segmented image (e.g., the first segmented image) may be obtained by segmenting a medical image (e.g., the first medical image). The region to be avoided may be determined based on the tissue segmented image.

In some embodiments, a plurality of segmented tissues may be fused and displayed in the tissue segmented image. In some embodiments, different tissues in the image may be labeled with different colors and fluorescence to distinguish the tissues.

In some embodiments, scanned image data (e.g., the first medical image) of a patient may be obtained. A plurality of different tissue data may be obtained by performing tissue segmentation based on features of the scanned image data. The tissue segmented image (e.g., the first segmented image) may be obtained by fusing the plurality of different tissue data. The features of various tissues may be different in different scanned images. The plurality of different tissue data may be obtained by performing the tissue segmentation using the features of the scanned image data, and then the tissue segmented image may be obtained by fusing the plurality of different tissue data, thereby improving the accuracy of the tissue data in the tissue segmented image.

In some embodiments, the scanned image data may include a single sequence image or multiple sequence images. In some embodiments, the sequence image refers to a digital imaging and communications in medicine (DICOM) image. A single sequence means one series. One series may include a plurality of images. The plurality of images may be subjected to 3D reconstruction to form 3D voxel data. Multiple sequences mean a plurality of series.

In some embodiments, if the scanned image data includes the multiple sequence images, registration may be performed on the multiple sequence images, and the tissue segmented image (e.g., the first segmented image) may be obtained by performing the tissue segmentation on registered multiple sequence images. In some embodiments, if the scanned image data includes the single sequence image, the registration may not be required.

More details regarding the first segmented image and the determination of the region to be avoided may be found elsewhere in the present disclosure (e.g., FIG. 3 and related descriptions thereof), which are not repeated here. In some embodiments, the region to be avoided may be determined in any reasonable and feasible manner, which is not limited here.

The surgical pathway refers to a puncture pathway from the needle entry point (the intervention point) on the human skin and the target point when surgical operations such as puncture and ablation are performed.

In some embodiments, a connecting line between the target point and the intervention point may be determined as the surgical pathway. In some embodiments, an initial pathway may be determined based on the target point and the intervention point, and the surgical pathway may be determined by adjusting initial pathway based on the region to be avoided. For example, the initial pathway may be adjusted to avoid the region to be avoided, and/or to a distance between the initial pathway and the region to be avoided may be adjusted to be greater than a distance threshold, etc.

Figure 19:
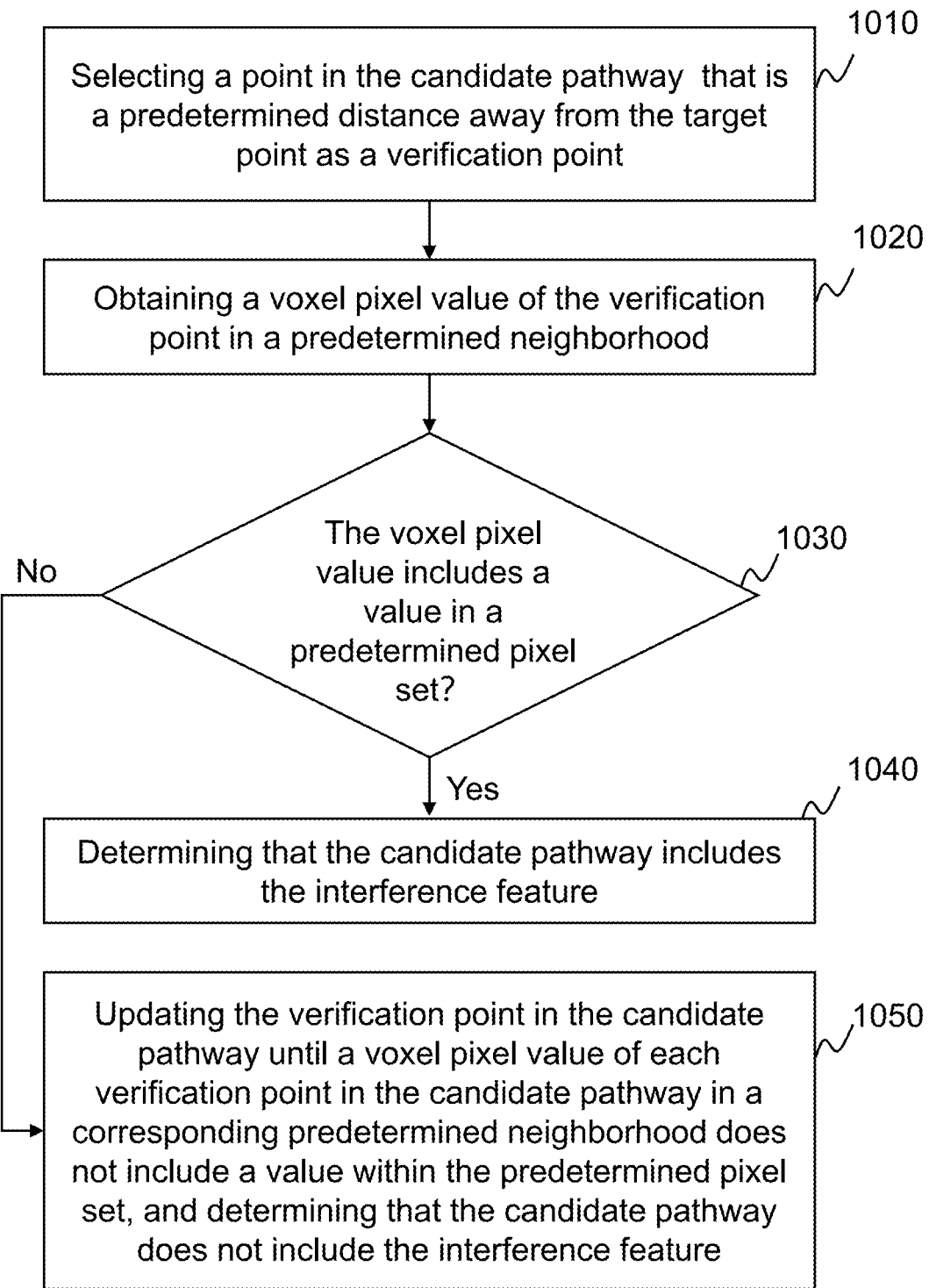
FIG. 19 is a schematic diagram illustrating an exemplary interference feature verification according to some embodiments of the present disclosure.
Figure 20:
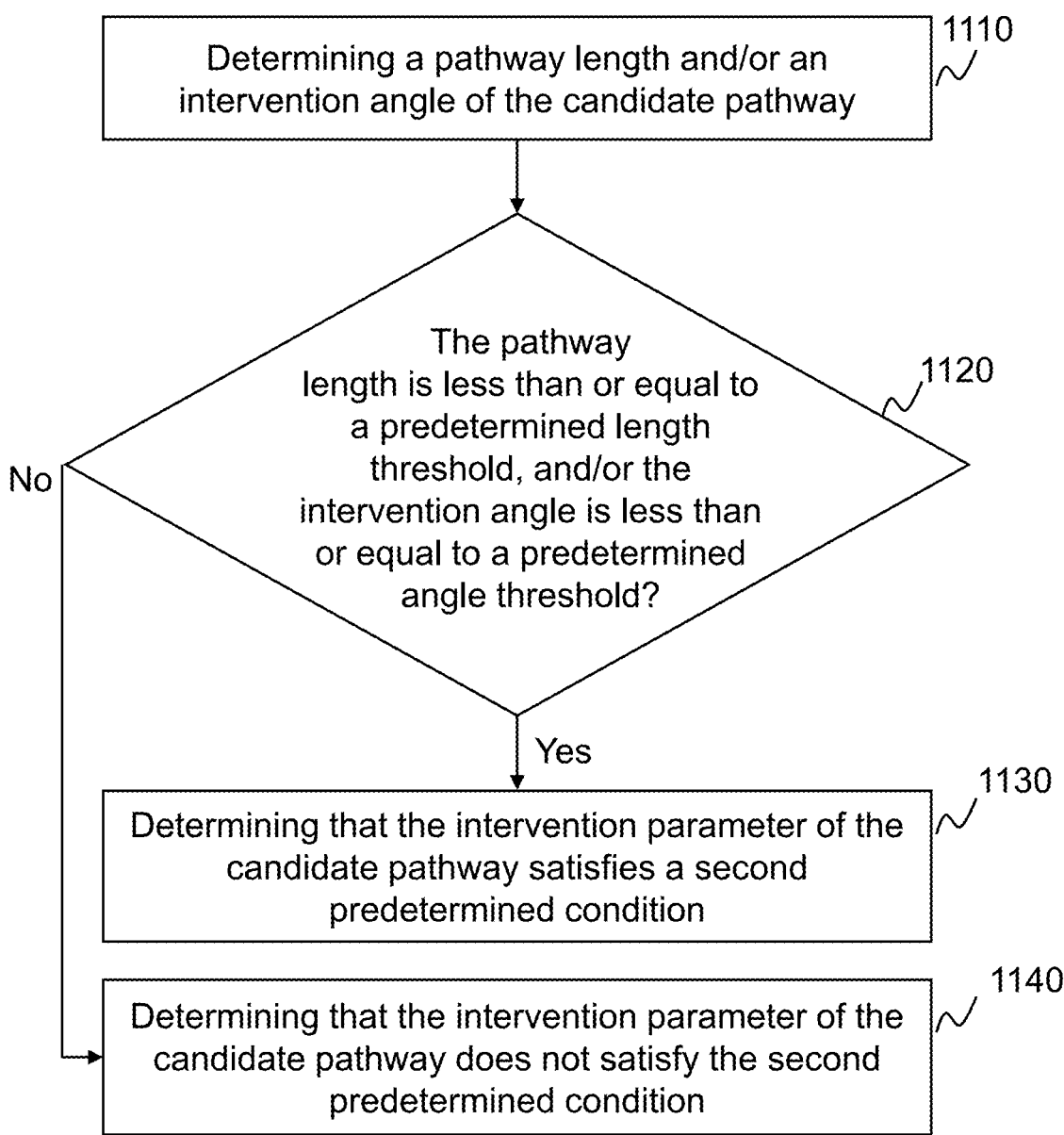
FIG. 20 is a schematic diagram illustrating an exemplary intervention parameter verification according to some embodiments of the present disclosure.

In some embodiments, the surgical pathway may be determined based on the target point and the second operation of the user on the target image (e.g., the first segmented image). In some embodiments, the reference pathway may be determined based on the target point and the second operation of the user on the first segmented image. The candidate pathway may be determined based on the reference pathway, and the surgical pathway may be determined by verifying the candidate pathway. More details regarding determining the candidate pathway and the verification thereof may be found in FIGS. 18-20 and related descriptions thereof, which are not repeated here.

In this embodiment, the target point and the intervention point may be determined by movement of the user on the target image of the display of the device, and then the surgical pathway may be determined, the process is fast and easy to operate, which improves the efficiency and accuracy of determining the surgical pathway.

In some embodiments, a minimum distance between the surgical pathway and the region to be avoided may be obtained. If the minimum distance is less than a corresponding distance threshold, a prompt operation may be performed through an alarm message. In some embodiments, after the prompting operation is performed through the alarm message, the region to be avoided, the distance threshold, the intervention point, and/or the target point may be adjusted based on an adjustment instruction (e.g., a first adjustment instruction, and a second adjustment instruction), thereby redetermining the surgical pathway based on an adjusted region to be avoided, an adjusted target point, an adjusted intervention point, and an adjusted distance threshold. In some embodiments, the surgical pathway may be implemented by the user or a surgical robot. More details may be found in FIG. 17 and its related descriptions, which are not repeated here.

It should be noted that the descriptions of the process 700 are intended to be exemplary and illustrative only, and do not limit the scope of application of the present disclosure. For those skilled in the art, various corrections and changes may be made to the process 700 under the guidance of the present disclosure. However, these corrections and changes remain within the scope of the present disclosure. For example, in operation 730, the surgical pathway may be adjusted based on real-time monitoring of the puncture procedure on the target object.

In some embodiments, as shown in FIG. 17, the pathway planning module 230 may be configured to determine a reference pathway in response to a second operation of a user on a first segmented image, and further determine an intervention point based on the reference pathway.

In some embodiments, a process 800 may be implemented by the surgical pathway processing system 100 (e.g., the processing device 140 of the surgical pathway processing system 100) or the surgical pathway processing system 200 (e.g., the pathway planning module 230). For example, the process 800 may be stored in a storage device (e.g., the storage device 150, and a storage unit of the system) in the form of a program or an instruction, and the process 800 may be implemented when the processor (e.g., the processing device 140) or modules of FIG. 2 executes/execute the program or the instruction.

In 810, the second operation of the user on the first segmented image may be received.

In some embodiments, the second operation may include a click operation or a slide operation. For example, the second operation may be a click or slide operation, etc., performed by the user using a finger or touch tool (e.g., a stylus, a touch glove, etc.) on the first segmented image on a touch display. As another example, the second operation may be a click operation of the user on the first segmented image on a non-touch display using a mouse, or a move operation on the first segmented image on the display using the mouse, etc. In some embodiments, the second operation may include a gesture operation, a voice operation, an expression operation, or the like, or any combination thereof, which are not limited to the present disclosure. In some embodiments, the second operation and the first operation may be the same or different operation types.

In 820, the reference pathway may be determined based on the second operation.

In some embodiments, a reference point may be determined in response to the second operation, and the reference pathway may be determined based on the target point and the reference point.

A location of the reference point may be different from a location of the target point. In some embodiments, the reference point may include any point in a direction of the target point and a direction of surgical intervention (a needle entry direction). For example, as shown in FIG. 22(*c*), T denotes the target point, E denotes the reference point, and E' denotes the intervention point. The reference point may be a point $E_1$ located between the target point and the intervention point, or a point $E_2$ or $E_3$ located above the intervention point. In some embodiments, the reference point may be an initial intervention point determined by the user.

In some embodiments, an action point of the second operation on the first segmented image may be determined, and the reference point may be determined based on the action point. For example, a button E representing the reference point may be provided in a display interface. The user may determine a location of point E by selecting the location of point E across the slices on the first segmented image by scrolling the mouse or touching the display screen, such as by clicking on the image in a current CT image slice. After the system receives the second operation of the user, the location of point E may be determined as the action point, and the action point may be determined as the reference point.

In some embodiments, an action pathway of the second operation on the first segmented image may be determined, and the reference point may be determined based on the action pathway. For example, the user may drag the point E on the first segmented image by moving or scrolling the mouse. Upon receiving the second operation of the user on the first segmented image, the system may determine the action pathway of the second operation on the first segmented image, and determines an end point (i.e., a target location point) of the action pathway as the reference point. The action pathway may be a pathway that the user moves a cursor to a target location using the mouse (e.g., a non-touch display) or via a finger/stylus (e.g., a touch display) with the target point as a starting point.

In some embodiments, the reference point may be determined in other ways, which is not limited to the present disclosure. For example, when the second operation is a coordinate point input by the user, the coordinate point may be determined as the reference point. As another example, when the second operation is a distance from the target point input by the user, the reference point may be determined based on the distance.

In some embodiments, the reference point may be updated in response to a third operation of the user on the first segmented image. More descriptions regarding the update of the reference point may be found in FIG. 18 and related descriptions thereof, which are not repeated here.

In some embodiments, a straight line connecting the target point and the reference point may be determined as the reference pathway.

In some embodiments, the action pathway of the second operation on the first segmented image may be determined, and the reference pathway may be determined based on the action pathway. In some embodiments, the action pathway of the second operation may be determined as the reference path.

For ease of understanding, in some embodiments, a method of determining the surgical pathway (e.g., the reference path, etc.) based on an action pathway may be referred to as a point-line interaction method, and a method of determining the surgical pathway through the action point may be referred to as a point-point interaction method.

In some embodiments, the determined target point, the reference point, the action pathway, and/or the reference pathway may be displayed on the target image (e.g., the first segmented image, the second segmented image, and the target medical image). For example, as shown in FIG. 23(*a*), after the user performs the first operation on the first segmented image, a target point T determined based on the first operation may be displayed on the first segmented image. After the user performs the second operation on the first segmented image, a reference point $E_1$ determined based on the second operation may be displayed on the first segmented image, and a reference pathway $TE_1$ formed based on the target point T and the reference point $E_1$ may be displayed on the first segmented image. As shown in FIG. 23(*b*), after the user performs the second operation on the first segmented image, the action pathway (e.g., a white line segment in the figure) (i.e., a line segment formed by the cursor with the target point as the starting point and the target location of the movement of the cursor as the end point) corresponding to the second operation may be displayed on the first segmented image.

In some embodiments, a new reference pathway may be determined through the third operation. More descriptions regarding the update of the reference pathway may be found in FIG. 18 and related descriptions thereof, which are not repeated here.

In 830, the intervention point may be determined based on the reference pathway.

In some embodiments, the intervention point may be the reference point. For example, when the reference point is an initial intervention point determined by the user and is located on a human skin interface, the reference point may be designated as the intervention point. In some embodiments, the intervention point may include a location point between the reference point and the target point. In some embodiments, the intervention point may include a point that extends to the skin interface along the reference pathway.

In some embodiments, the intervention point may be determined by a needle entry point automated localization algorithm based on the reference pathway. For example, the needle entry point automated localization algorithm may include, but is not limited to, stepping search in voxel coordinates, skin grid reconstruction, binary tree search based on three-dimensional space, or the like, or any combination thereof.

Merely by way of example, the system may perform the following operations: (1) coordinates of skin points within a mask may be extracted based on the target image (here referred to as an image after image segmentation, e.g., the first segmented image), and a skin point cloud P in an actual three-dimensional space may be obtained based on spacing values in an X-direction, a Y-direction, and a Z-direction; (2) the point cloud P may be stored in the form of a KD-tree, and a bounding box Box of point cloud P may be calculated; (3) a query point may be set as V, and a step size L may be moved along a direction of a reference pathway TE determined based on the target point T and the reference point E, and a count of queries may be calculated based on the target point T and the direction of the reference pathway TE (e.g., $TE_1$, $TE_2$, and $TE_3$ in FIG. 22(*c*); (4) a query radius R of a point V may be set, a point within a neighborhood of the query radius R may be retrieved in the point cloud P, if the point exists, the point may be the intervention point, a distance D from the point to a straight line TE may be calculated, the query point V may be updated, and operation (4) may be repeated; if the point does not exist, the query point V may be updated, and operation (4) may be repeated; (5) until an end of a loop (e.g., the query along the direction of the reference pathway to the outer skin tissue), a point corresponding to a smallest distance D may be taken as the intervention point E' (e.g., points $E_1'$, $E_2'$, and $E_3'$ in FIG. 22(*c*)).

In the embodiments of the present disclosure, the intervention point may be determined through the needle entry point automated localization algorithm, so that a situation that determining an erroneous surgical pathway if the determined reference point is not the needle entry point on the skin or the reference point is unreasonable may be avoided, thereby improving the accuracy and rationality of the determined surgical pathway.

It should be noted that the descriptions of the process 800 are intended to be exemplary and illustrative only and do not limit the scope of application of the present disclosure. For those skilled in the art, various corrections and changes may be made to the process 800 under the guidance of the present disclosure. For example, the first segmented image in 810 may be replaced with the second segmented image, the target medical image, or the like. However, these corrections and changes are still within the scope of the present disclosure.

Figure 18:
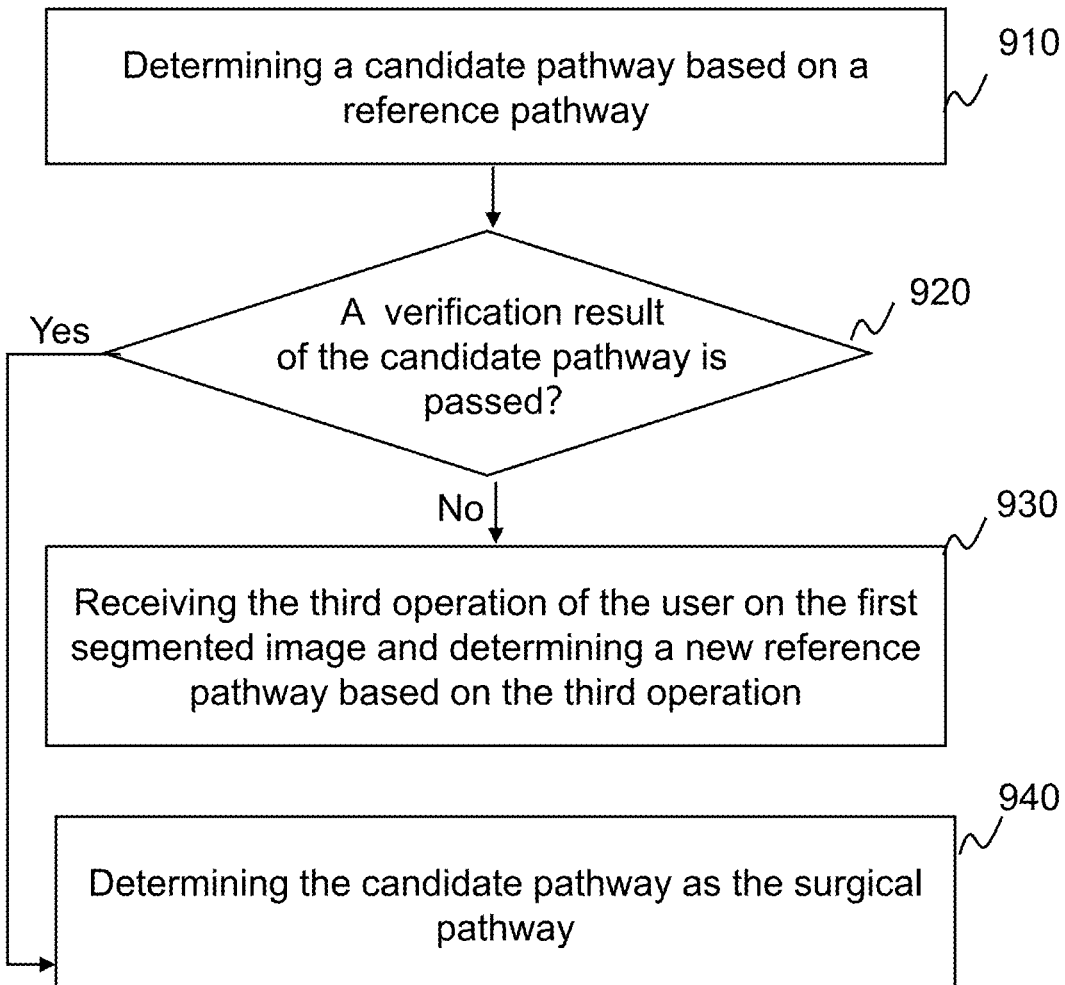
FIG. 18 is a flowchart illustrating an exemplary process for determining a surgical pathway according to some other embodiments of the present disclosure.

In some embodiments, as shown in FIG. 18, the pathway planning module 230 may be configured to determine a candidate pathway based on a reference path, and determine a surgical pathway by verifying the candidate pathway.

In some embodiments, a process 900 may be implemented by the surgical pathway processing system 100 (e.g., the processing device 140 of the surgical pathway processing system 100) or the surgical pathway processing system 200 (e.g., the pathway planning module 230). For example, the process 900 may be stored in a storage device (e.g., storage device 150, and a storage unit of the system) in the form of a program or an instruction, and a process 900 may be implemented when a processor (e.g., the processing device 140) or modules of FIG. 2 executes/execute the program or the instruction.

In 910, a candidate pathway may be determined based on a reference pathway.

In some embodiments, the candidate pathway may be the reference pathway. For example, when a reference point is an intervention point, the reference pathway formed by a connecting line between the reference point and a target point may be determined as the candidate pathway. In some embodiments, the candidate pathway may include all or a portion of the reference pathway.

In some embodiments, when the reference point or the reference pathway is located within a human skin interface, the candidate pathway may be determined based on an extension pathway of the reference path. For example, as shown in FIG. 23(*a*), if a reference point $E_1$ is within the human skin interface (e.g., the overall mask), a reference pathway $TE_1$ may be extended to the human skin interface to form a candidate pathway $TF_1$. In some embodiments, when the reference point is outside of the human skin interface, or when the reference pathway extends beyond the human skin interface, the candidate pathway (e.g., a pathway $TF_1$ in FIG. 23(*b*)) may be determined based on an intersection point of the reference pathway and the human skin interface.

In some embodiments, the candidate pathway may be determined based on the target point and the intervention point. For example, a connecting line of the target point and the intervention point may be determined as the candidate pathway.

In some embodiments, the determined candidate pathway may be displayed on the target image. As shown in FIG. 23(*b*), if the reference pathway (e.g., the pathway $TE_2$) does not extend beyond the human skin interface, the candidate pathway (e.g., the pathway $TF_2$) formed by an extension of the reference pathway to the human skin interface and an intersection point $F_2$ of the candidate pathway with the human skin interface may be displayed on the target image. If the reference pathway extends beyond the human skin interface, an intersection point $F_1$ of the reference pathway with the human skin interface may be displayed on the target image. A line segment formed by the intersection point with the target point may be the candidate pathway (e.g., the pathway $TF_1$).

In 920, whether a verification result of the candidate pathway is passed may be determined.

In some embodiments, the verification of the candidate pathway be realized by determining whether the candidate pathway includes an interference feature and/or whether an intervention parameter satisfies a second predetermined condition. The specific method of determining whether the candidate pathway includes the interference feature and/or determining whether the intervention parameter of the candidate pathway satisfies the second predetermined condition may not be limited in the embodiments, as long as the functions may be realized.

Whether the candidate pathway includes the interference feature means whether there is an interference between the candidate pathway and an organ, i.e., whether the candidate pathway includes various tissues and organs of the human body that are not allowed to pass through. For example, if the candidate pathway includes a dangerous organ such as the liver, or the candidate pathway is close to the dangerous organ, etc., the candidate pathway may include the interference feature. In some embodiments, the interference verification of the candidate pathway may be achieved by intersecting the mask of candidate pathway expansion as a puncture needle pathway with a mask of each organ, or by discretizing a puncture pathway step query, etc., which are not limited in the present disclosure. More descriptions regarding the verification of the interference feature of the candidate pathway may be found in FIG. 19 and related descriptions thereof, which are not repeated here.

The intervention parameter (also referred to as a puncture parameter) refers to a parameter such as a puncture depth, a puncture angle (an intervention angle), or other parameters.

In some embodiments, the puncture parameter may include a pathway parameter and/or a puncture instrument parameter. For example, the pathway parameter may include a pathway length, a pathway intervention angle, etc. The puncture instrument (e.g., an ablation needle, and a puncture needle) parameter may include, a puncture instrument length, a diameter (e.g., a length, and a diameter of the puncture needle), etc.

In some embodiments, the second predetermined condition may include a predetermined length threshold and/or a predetermined angle threshold.

In some embodiments, if the pathway length of the candidate pathway is less than or equal to the predetermined length threshold, and/or the pathway intervention angle is less than or equal to the predetermined angle threshold, it may be determined that the intervention parameter of the candidate pathway satisfies the second predetermined condition; and if the pathway length of the candidate pathway is greater than the predetermined length threshold, and/or the pathway intervention angle is greater than the predetermined angle threshold, it may be determined that the intervention parameter of the candidate pathway does not satisfy the second predetermined condition. More details may be found in FIG. 20 and related descriptions thereof, which are not repeated here.

In some embodiments, whether the candidate pathway includes the interference feature may be determined first, and then whether the candidate pathway satisfies the second predetermined condition may be determined. In some embodiments, whether the candidate pathway satisfies the second predetermined condition may be determined first, and then whether the candidate pathway includes the interference feature may be determined. In some embodiments, whether the candidate pathway includes the interference feature and whether the candidate pathway satisfies the second predetermined condition may be determined simultaneously. In some embodiments, it may be only determined that whether the candidate pathway includes the interference feature or whether the candidate pathway satisfies the second predetermined condition.

In some embodiments, whether the pathway length of the candidate pathway is less than or equal to the predetermined length threshold may be determined first, then whether the pathway includes the interference feature may be determined, and whether the pathway intervention angle is less than or equal to the predetermined angle threshold may be determined finally.

In some embodiments, pathway planning conditions may be determined based on specific clinical needs for surgical pathway planning. For example, whether the target point and the intervention point of the candidate pathway are in a same slice may be determined, etc., which is not limited in the embodiments.

In some embodiments, if the candidate pathway does not include the interference feature and/or the intervention parameter of the candidate pathway satisfies the second predetermined condition, the verification of the candidate pathway may be passed; or if the candidate pathway includes the interference feature and/or the intervention parameter of the candidate pathway does not satisfy the second predetermined condition, the verification of the candidate pathway may not be passed. For example, if the system verifies the candidate pathway by determining whether the candidate pathway includes the interference feature, and if the candidate pathway does not include the interference feature, i.e., the candidate pathway does not pass various tissues and organs of the human body that are not allowed to pass, the verification of the candidate pathway may be passed; or if the candidate pathway includes the interference feature, the candidate pathway may pass various tissues and organs of the human body that are not allowed to pass, and the verification of the candidate pathway may not be passed. As another example, if the system verifies the candidate pathway by determining whether the intervention parameter of the candidate pathway satisfies the second predetermined condition, and if the intervention parameter of the candidate pathway satisfies the second predetermined condition, the verification of the candidate pathway may be passed; or if the intervention parameter of the candidate pathway does not satisfy the second predetermined condition, the verification of the candidate pathway may not be passed. As yet another example, if the system verifies the candidate pathway by simultaneously determining whether the candidate pathway includes the interference feature and whether the intervention parameter satisfies the second predetermined condition, and if the candidate pathway does not include the interference feature and the intervention parameter satisfies the second predetermined condition, the verification of the candidate pathway may be passed; or if the candidate pathway includes the interference feature and the intervention parameter does not satisfy the second predetermined condition, the verification of the candidate pathway may not be passed.

In some embodiments, if the candidate pathway simultaneously satisfies that the candidate pathway does not include the interference feature, the pathway length is less than or equal to the predetermined length threshold, and the pathway intervention angle is less than or equal to the predetermined angle threshold, the verification of the candidate pathway may be passed. In some embodiments, if the candidate pathway does not satisfy that the candidate pathway does not include the interference feature, or the pathway length is less than or equal to the predetermined length threshold, or the pathway intervention angle is less than or equal to the predetermined angle threshold, the verification of the candidate pathway may not be passed.

The candidate pathway may be verified based on specific clinical needs for puncture pathway planning in the embodiments, thereby improving the correctness and feasibility of the resulting surgical pathway.

In some embodiments, when the verification of the candidate pathway is passed, the candidate pathway may be determined as the surgical pathway by performing 940; and when the verification of the candidate pathway is not passed, the third operation of the user on the first segmented image may be received and a new reference pathway may be determined based on the third operation by performing 930.

In some embodiments, when the verification result of the candidate pathway is passed, the surgical pathway may be displayed in a first color (e.g., yellow). In some embodiments, when the verification result of the candidate pathway is not passed, the candidate pathway may be displayed in a second color (e.g., red). In some embodiments, the first color and the second color may be any two different colors, e.g., the first color may be green, the second color may be grey, etc., which are not limited in the present disclosure.

In some embodiments, the candidate pathway of which the verification result is passed or the candidate pathway of which the verification result is not passed may be displayed in other ways, which are not limited to the present disclosure. For example, when the verification result of the candidate pathway is passed, the candidate pathway may be displayed, and when the verification result of the candidate pathway is not passed, the candidate pathway may not be displayed. As another example, when the verification result of the candidate pathway is not passed, an alarm may be issued with an error box. As another example, the verification result of the candidate pathway may be represented by thick and thin lines and dotted and solid lines, etc.

By displaying the verification result of the candidate pathway on the target image in different ways, it is easier for the user to more clearly know the verification result of the candidate pathway and the determined surgical pathway.

In 930, the third operation of the user on the first segmented image may be received, and the new reference pathway may be determined based on the third operation.

In some embodiments, the third operation may be a same type of operation as the second operation. Descriptions regarding the third operation may refer to the specific descriptions regarding the second operation in the above embodiments, which are not repeated here.

When the verification result of the candidate pathway is not passed, it may represent that the candidate pathway does not satisfy the clinical needs for puncture pathway planning.

In some embodiments, when the verification result of the candidate pathway is not passed, the third operation of the user on the first segmented image may be received, the reference point may be updated based on the third operation, and the new reference pathway may be determined based on the updated reference point.

In some embodiments, an action point of the third operation may be determined, and the new reference pathway may be determined based on the action point (i.e., the new reference pathway may be determined by a point-point interaction method). For example, in response to the third operation of the user on the first segmented image, the action point of the third operation may be determined as the new reference point, and the new reference pathway may be determined based on the target point and the new reference point.

Merely by way of example, as shown in FIG. 23(a), the system may verify the candidate pathway $TF_1$. After determining that the verification of the candidate pathway is not passed, the user may perform the third operation on the first segmented image, and a new reference point $E_2$ may be displayed on the first segmented image based on the third operation of the user. A new reference pathway $TE_2$ (i.e., a line segment formed by the target point T and the new reference point $E_2$) may be determined based on the target point T and the new reference point $E_2$, and the new reference pathway $TE_2$ may be displayed on the first segmented image.

In some embodiments, an action pathway of the third operation may be determined, and a new reference pathway may be determined based on the action pathway (i.e., a new reference pathway may be determined by the point-line interaction method). For example, in response to the third operation of the user on the first segmented image, the action pathway of the third operation may be determined as the new reference pathway, or a new reference point may be determined based on the action pathway, and the new reference pathway may be determined based on the new reference point.

Merely by way of example, as shown in FIG. 23(b), after the system verifies the candidate pathway, if it is determined that the verification of the candidate pathway $TF_1$ is not passed, the user may perform the third operation on the first segmented image. That is, the mouse may be moved so that the cursor may be moved again on the first segmented image to form a new action pathway $TE_2$, and the new action pathway $TE_2$ may be determined as the new reference pathway.

In some embodiments, when the user performs the third operation, the candidate pathway (e.g., the candidate pathway $TF_1$ in FIG. 23(b)) of which the verification is not passed may no longer be displayed. In some embodiments, when the user performs the third operation, the candidate pathway of which the verification is not passed may be displayed.

In some embodiments, a new candidate pathway may be determined based on the new reference pathway. For example, as shown in FIG. 23(b), when a new reference point $E_2$ is within the human skin interface, a new reference pathway $TE_2$ may be extended to the human skin interface to form a new candidate pathway $TF_2$. As another example, when the new reference point or reference pathway is outside the human skin interface, the new candidate pathway may be determined based on an intersection point of the new reference pathway with the human skin interface. The determination of the new candidate pathway may be similar to the determination of the candidate pathway in operation 910. More details may be found in the descriptions of operation 910, which are not repeated here.

In some embodiments, the new reference pathway and/or the candidate pathway may be displayed on the target image.

In embodiments of the present specification, when the verification result of the candidate pathway is not passed, the candidate pathway may be updated by receiving the third operation from the user, thereby updating the candidate path, and making the process of determining the surgical pathway simple and fast.

In 940, the candidate pathway may be determined as the surgical pathway.

When the verification result of the candidate pathway is passed, it means that the candidate pathway satisfies the clinical needs for puncture pathway planning, and thus the candidate pathway may be determined as the surgical pathway.

In some embodiments, when the verification result of the candidate pathway is passed, an operation of the user for confirming the surgical pathway on the target image may be received. For example, when it is determined that the verification result of the candidate pathway is passed, it may indicate that the determined candidate pathway is an accurate surgical pathway, and then the operation of the user for confirming the surgical pathway on the target image or a terminal device may be received. For example, the confirmation operation may include a click operation, a gesture operation, or the like. The surgical pathway may be confirmed through the confirmation operation, so that the determined surgical pathway may not change when the user moves the cursor again.

In some embodiments, the verification result of the candidate pathway may be output. For example, the verification result may include that the candidate pathway satisfies the clinical needs for puncture pathway planning or that the candidate pathway does not satisfy the clinical needs for puncture pathway planning. In some embodiments, an output method of the verification result may include, but is not limited to, a pop-up prompt, a text message prompt, a voice prompt, or any other method capable of realizing the function thereof, which is not limited in the present disclosure.

The method for determining the surgical pathway provided in the embodiments of the present specification realizes interaction with the user by receiving the first operation and the second operation of the user, and the process of interaction is more convenient. In addition, the method can verify the determined candidate pathway in real time and/or output the verification result, so that the user can determine whether the surgical pathway is accurate and feasible in real time, thereby making the determined surgical pathway highly practical and convenient.

In some embodiments, the pathway length and the intervention angle of the determined surgical pathway may be displayed near the candidate pathway on the target image (e.g., the first segmented image, the second segmented image, or the target medical image), thereby facilitating the medical staff to more intuitively obtain parameter information of the candidate pathway.

In some embodiments, a puncture guidance set may be determined based on the surgical pathway. Before the surgery is performed, a medical image (e.g., the first segmented image or the first medical image) obtained prior to the surgery may be registered to a medical image (e.g., the second segmented image or the second medical image) obtained during the surgery, and the puncture guidance set of the medical image prior to the surgery may be transformed to the medical image during the surgery, thereby assisting the medical staff in completing the surgery based on the puncture guidance set. In some embodiments, the puncture guidance set may be determined based on a slice in which the target point and the needle entry point of the surgical pathway are located. In some embodiments, if the target point and the needle entry point of the surgical pathway are in a same slice of a non-human tissue or organ, guide points may be selected at equal distances from the surgical pathway, and a set of the selected multiple guide points may be used as the puncture guidance set. If the target point and the needle entry point of the surgical pathway are not in the same slice, an intersection point of the surgical pathway with a plane in which each slice is located is determined, and a set of determined multiple intersection points may be used as the puncture guidance set.

It should be noted that the foregoing descriptions of the process 900 are intended to be exemplary and illustrative only and do not limit the scope of application of the present disclosure. For those skilled in the art, various corrections and changes may be made to the process 900 under the guidance of the present disclosure. For example, in operation 930, the first segmented image may be replaced with the target medical image. However, these corrections and changes are still within the scope of the present disclosure.

In some embodiments, the pathway planning module 230 may calculate spatial coordinates of various tissues and organs of the human body that are not allowed to pass, and calculate spatial coordinates of the candidate pathway, and determine whether the candidate pathway includes the interference feature by determining whether the spatial coordinates of the candidate pathway are in the spatial coordinates of the various tissues and organs of the human body that are not allowed to pass. If the spatial coordinates of the candidate pathway are in the spatial coordinates of the various tissues and organs of the human body that are not allowed to pass, it may be determined that the candidate pathway includes the interference feature; and if the spatial coordinates of the candidate pathway are not in the spatial coordinates of the various tissues and organs of the human body that are not allowed to pass, it may be determined that the candidate pathway does not include the interference feature.

In 1010, a point in the candidate pathway that is a predetermined distance away from the target point may be selected as a verification point.

In some embodiments, the predetermined distance may include a pixel distance between two points. For example, the predetermined distance may be a pixel distance. In some embodiments, on a tissue segmented image (e.g., the first segmentation image, the second segmentation image, or the target medical image), a point in the candidate pathway that is the predetermined distance away from the target point may be selected as the verification point. For example, on the first segmented image, a pixel point in a pixel region corresponding to the candidate pathway that is the predetermined distance away from the target point may be selected as the verification point.

In 1020, a voxel pixel value of the verification point in a predetermined neighborhood may be obtained.

The predetermined neighborhood refers to a spherical three-dimensional stereoscopic region formed with the verification point as a center and a predetermined length as a radius. Correspondingly, the voxel pixel value may be a pixel value of each point within the three-dimensional stereoscopic region.

In the embodiments of the present disclosure, a specific structure, or a size of the region of the predetermined neighborhood may not be limited, and the user may set accordingly based on an actual situation.

In 1030, whether the voxel pixel value includes a value in a predetermined pixel set.

In some embodiments, the predetermined pixel set may include one or more predetermined pixel thresholds. The plurality of predetermined pixel thresholds may reflect pixel values corresponding to the various tissues and/or organs of the human body that are not allowed to pass. In some embodiments, the predetermined pixel thresholds may include pixel values corresponding to the various tissues and organs of the human body on the first segmented image. For example, the predetermined pixel thresholds may be marker values of masks corresponding to vascular tissues on the first segmented image. In some embodiments, when a plurality unpuncturable organs and tissues are determined, each organ and tissue may correspond to a pixel value for labeling and distinction, and the predetermined pixel set may include the plurality of predetermined pixel thresholds. In some embodiments, when a single unpuncturable organ or tissue is determined, the predetermined pixel set may include a predetermined pixel threshold corresponding to the organ and tissue.

In some embodiments, if a voxel pixel value of a current verification point of the candidate pathway includes a value in the predetermined pixel set, it may be determined that the candidate pathway includes the interference feature by performing operation 1040; and if the voxel pixel value of the current verification point of the candidate pathway does not include a value in the predetermined pixel set, a next verification point in the candidate pathway may be determined by performing operation 1050.

In 1040, it may be determined that the candidate pathway includes the interference feature.

In some embodiments, if the voxel pixel value of the verification point includes a value in the predetermined pixel set (e.g., the voxel pixel value of the verification point is equal to one of the predetermined pixel thresholds within the predetermined pixel set), it is indicated that a predetermined neighborhood of the verification point includes an unpunctured tissue or organ of the human body, which means that the candidate pathway includes the interference feature.

In 1050, the verification point in the candidate pathway may be updated until a voxel pixel value of each verification point in the candidate pathway in a corresponding predetermined neighborhood does not include a value within the predetermined pixel set, and it may be determined that the candidate pathway does not include the interference feature.

In some embodiments, if the voxel pixel value of the current verification point does not include a value in the predetermined pixel set (e.g., the voxel pixel value of the current verification point is not equal to any of the predetermined pixel thresholds within the predetermined pixel set), it is indicated that the predetermined neighborhood of the verification point does not include the unpuncturable tissue or organ of the human body, the verification point in the candidate pathway may be updated, and the voxel pixel value of the updated verification point in the predetermined neighborhood may be compared with values in the predetermined pixel set.

In some embodiments, the method of updating the verification point in the candidate pathway may include using a previous verification point as a new starting point, and selecting a point after moving a predetermined distance along a vector direction from the target point to the needle entry point as an updated verification point. For example, a point of a pixel distance from the point to the current verification point may be selected as the new verification point by continuously moving along a vector direction of the candidate pathway TF (or the reference pathway TE).

In some embodiments, if it is determined that a voxel pixel value in a predetermined neighborhood of each verification point in the candidate pathway does not include a value in the predetermined pixel set (e.g., the voxel pixel value in the predetermined neighborhood of each verification point in the candidate pathway is not equal to any one of the predetermined pixel thresholds within the predetermined pixel values), it may indicate that the candidate pathway does not pass the unpuncturable tissues or organs of the human body, and it may be determined that the candidate pathway does not include the interference feature.

In some embodiments, the updating of the verification point may be stopped when an end (i.e., the intervention point) of the candidate pathway is traversed. When the verification point is moved to the intervention point, it may indicate that a maximum puncture depth of the pathway is traversed, and if there is no danger of interference, the current pathway may be safe.

Merely by way of example, taking an unpuncturable organ as an example (i.e., the predetermined pixel set includes one predetermined pixel threshold), as shown in FIG. 22(a) or FIG. 22(b), for the candidate pathway $TF_1$ ($TF_2$), the target point T may be taken as the starting point, a point that is one pixel away from point T along a vector direction of the $TF_1$ ($TF_2$) or $TE_1$ (or $TE_2$) may be selected as an initial verification point Q, a query radius r may be set, and whether a voxel pixel value in a predetermined neighborhood of Q is equal to a marker value (i.e., the predetermined pixel threshold) of an unpuncturable organ mask may be queried. If the voxel pixel value in the predetermined neighborhood of Q is equal to the marker value of the unpuncturable organ mask, it may be determined that the current candidate pathway includes the interference feature, and a loop may be ended; and if the voxel pixel value in the predetermined neighborhood of Q is not equal to the marker value of the unpuncturable organ mask, the initial verification point Q may have no interference, and the loop may be continued to update the initial verification point Q. Whether the voxel pixel value in the predetermined neighborhood of an updated verification point Q is equal to the marker value of the unpuncturable organ mask may be queried until the Q point is moved to $F_1$ ($F_2$). When the voxel pixel value in predetermined neighborhood of each verification point in the candidate pathway $TF_1$ ($TF_2$) is not equal to the marker value of the unpuncturable organ mask, it may indicate that the current candidate pathway does not include the interference feature. That is, there may be no danger of interference, and the current pathway may be safe.

In the embodiments, suitable thresholds for the interference verification of the candidate pathway may be selected by using grayscale features of various tissues and organs of the human body, which is simple and easy to understand, and also improves the accuracy of the determined surgical pathway.

It should be noted that the foregoing descriptions of the process 1000 are intended to be exemplary and illustrative only, and do not limit the scope of application of the present disclosure. For those skilled in the art, various corrections and changes may be made to the process 1000 under the guidance of the present disclosure. However, these corrections and changes remain within the scope of the present disclosure. For example, the interference verification of the candidate pathway may be achieved by other methods.

In 1110, a pathway length and/or an intervention angle of the candidate pathway may be determined.

The pathway length refers to a length from the target point to the needle entry point (intervention point). In some embodiments, the pathway length may be determined based on a straight line distance between the target point corresponding to the candidate pathway and the needle entry point.

The intervention angle refers to an angle between a puncture tool and a predetermined normal line when puncturing is performed along the pathway. In some embodiments, a skin point cloud set may be determined based on the needle entry point, the predetermined normal line may be determined based on the skin point cloud set, and then the intervention angle of the candidate pathway may be determined. More descriptions regarding the determination of the intervention angle may be found in FIG. 14 and related descriptions thereof, which are not repeated here.

In some embodiments, when a puncture parameter (an intervention parameter) includes the pathway length and the intervention angle, the pathway length and the intervention angle may be determined simultaneously based on the candidate pathway. In some embodiments, when the puncture parameter includes only the pathway length or the intervention angle, the pathway length or the intervention angle may be determined based on the candidate pathway.

In 1120, whether the pathway length is less than or equal to a predetermined length threshold may be determined, and/or whether the intervention angle is less than or equal to a predetermined angle threshold may be determined.

In some embodiments, in operation 1110, if only the pathway length of the candidate pathway is obtained, whether the pathway length is less than or equal to the predetermined length threshold may be determined by comparing the pathway length with the predetermined length threshold. In some embodiments, in operation 1110, if only the intervention angle of the candidate pathway is obtained, whether the intervention angle is less than or equal to the predetermined angle threshold may be determined by comparing the intervention angle with the predetermined angle threshold. In some embodiments, in operation 1110, if the pathway length and the intervention angle of the candidate pathway are simultaneously obtained, whether the pathway length is less than or equal to a predetermined length threshold and whether the intervention angle is less than or equal to a predetermined angle threshold may be determined simultaneously.

In some embodiments, in operation 1120, if only whether the pathway length is less than or equal to the predetermined length threshold is determined, and if the pathway length is less than or equal to the predetermined length threshold, operation 1130 may be performed to determine that the intervention parameter of the candidate pathway satisfies a second predetermined condition; or if the pathway length is greater than the predetermined length threshold, operation 1140 may be performed to determine that the pathway parameter of the candidate pathway does not satisfy the second predetermined condition.

In some embodiments, in operation 1120, if only whether the intervention angle is less than or equal to the predetermined angle threshold, and if the intervention angle is less than or equal to the predetermined angle threshold, operation 1130 may be performed to determine that the intervention parameter of the candidate pathway satisfies the second predetermined condition; or if the intervention angle is greater the predetermined angle threshold, operation 1140 may be performed to determine that the pathway parameter of the candidate pathway does not satisfy the second predetermined condition.

In some embodiments, in operation 1120, if whether the pathway length is less than or equal to a predetermined length threshold and whether the intervention angle is less than or equal to a predetermined angle threshold are determined simultaneously, and if the pathway length is less than or equal to the predetermined length threshold and the intervention angle is less than or equal to the predetermined angle threshold, operation 1130 may be performed to determine that the intervention parameter of the candidate pathway satisfies the second predetermined condition; or if the pathway length is greater than the predetermined length threshold and the intervention angle is greater than the predetermined angle threshold, operation 1140 may be performed to determine that the pathway parameter of the candidate pathway does not satisfy the second predetermined condition.

The predetermined length threshold and the predetermined angle threshold are not limited in the embodiments, and the user may set the predetermined length threshold and the predetermined angle threshold based on an actual situation.

It should be noted that the foregoing descriptions of the process 1100 are intended to be exemplary and illustrative only and do not limit the scope of application of the present disclosure. For those skilled in the art, various corrections and changes may be made to the process 1100 under the guidance of the present disclosure. However, these corrections and changes remain within the scope of the present disclosure.

Figure 21:
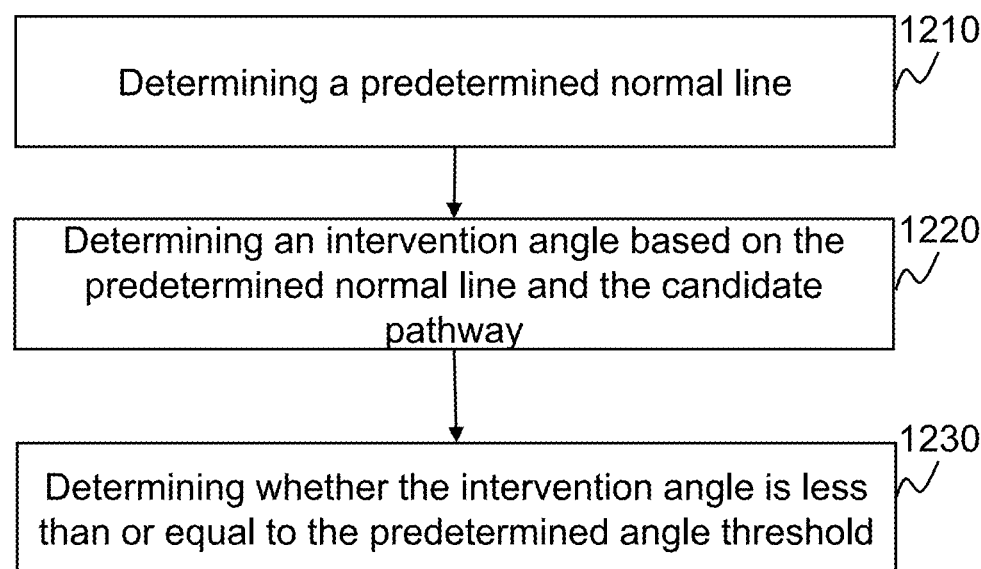
FIG. 21 is a schematic diagram illustrating an exemplary intervention angle verification according to some embodiments of the present disclosure.

FIG. 21 is a schematic diagram illustrating an exemplary intervention angle verification according to some embodiments of the present disclosure.

In 1210, a predetermined normal line may be determined.

In some embodiments, the predetermined normal line refers to a line perpendicular to a plane of a bed board of a medical bed in which a target object (e.g., a patient) is located, or a line perpendicular to a horizontal plane.

In 1220, an intervention angle may be determined based on the predetermined normal line and a candidate pathway.

In some embodiments, an angle between projections of the candidate pathway and the predetermined normal line on a same plane may be determined as an intervention angle. In some embodiments, a puncture instrument may be simulated based on the candidate pathway, and the intervention angle may be determined based on planar projections of the puncture instrument and the predetermined normal line along a same direction. For example, a processing device may simulate a line segment formed by extending the candidate pathway for a certain distance after passing through the intervention point as a puncture needle in an actual surgical procedure, use an angle between planar projections of the simulated puncture needle and the predetermined normal line along a relatively long direction (i.e., a long side direction of the bed board) of the bed board of the medical bed as the intervention angle, or use an angle between planar projections of the simulated puncture needle and the predetermined normal line along a relatively short direction (i.e., a short side direction of the bed board) of the bed board of the medical bed as the intervention angle.

In some embodiments, the puncture instrument may be simulated based on the candidate pathway, and the intervention angle may be determined based on the planar projections of the puncture instrument and the predetermined normal line along different directions. For example, the processing device may use an angle between a planar projection of the simulated puncture needle along a relatively long direction of the bed board of the medical bed and a planar projection of the predetermined normal line along a relatively short direction of the bed board of the medical bedpan as the intervention angle.

The angle between the puncture needle (i.e., the candidate pathway) and the normal line of the plane of the bed board of the medical bed is used as the intervention angle for verification, due to there is a relationship between a coordinate system corresponding to the bed board of the medical bed and a system coordinate system of the surgical processing pathway, it can help guide the positioning of a surgical robot, thereby improving the puncture efficiency and accuracy.

In 1230, whether the intervention angle is less than or equal to the predetermined angle threshold is determined.

In some embodiments, the predetermined angle threshold may be any reasonable value. For example, the predetermined angle threshold may be 3 degrees, 5 degrees, 10 degrees, 60 degrees, etc., which is not limited in the present disclosure. In some embodiments, the predetermined angle threshold may be set according to a manner of determining the intervention angle. For example, when the intervention angle is the angle between the planar projections of the simulated puncture needle and the predetermined normal line along the same direction, the predetermined angular threshold may be 5 degrees (or 7 degrees, 10 degrees, etc.), and if the intervention angle is less than or equal to 5 degrees, it may be determined that the candidate pathway satisfies the second predetermined condition. As another example, when the intervention angle is the angle between the planar projections of the simulated puncture needle and the predetermined normal line in different directions, the predetermined angle threshold may be 60 degrees.

In some embodiments, whether the intervention angle is less than or equal to the predetermined angle threshold may be determined by comparing the intervention angle with the predetermined angle threshold.

In the embodiments of the present specification, by determining whether the intervention angle of the candidate pathway satisfies the corresponding condition, the finally obtained surgical pathway may be more consistent with the clinical needs for the puncture pathway planning, thereby improving the correctness and feasibility of the surgical pathway.

It should be noted that the foregoing descriptions of the process 1200 are intended to be exemplary and illustrative only, and do not limit the scope of application of the present specification. For those skilled in the art, various corrections and changes may be made to the process 1200 under the guidance of the present disclosure. However, these corrections and changes remain within the scope of the present disclosure. For example, in some embodiments, the intervention angle may be determined based on a plane corresponding to a skin point set including the intervention point. Merely by way of example, coordinates of skin points within the mask may be read based on a skin mask in the first segmented image, and a skin point cloud P in an actual 3D space may be obtained based on spacing values in an X-direction, a Y-direction, and a Z-direction. Then a skin point set O of the intervention point F in a neighborhood R may be retrieved. For points within the point set O, least squares are used to fit them into a plane and calculate an outward normal of the plane as N. An angle between the outward normal line N and the candidate pathway (e.g., vectors $TF_1$ or $TF_2$ shown in FIG. 23(*b*)) may be calculated and determined as the intervention angle. As another example, in some embodiments, an angle between the candidate pathway and the plane of the bed board of the medical bed may be determined as the intervention angle.

Figure 24:
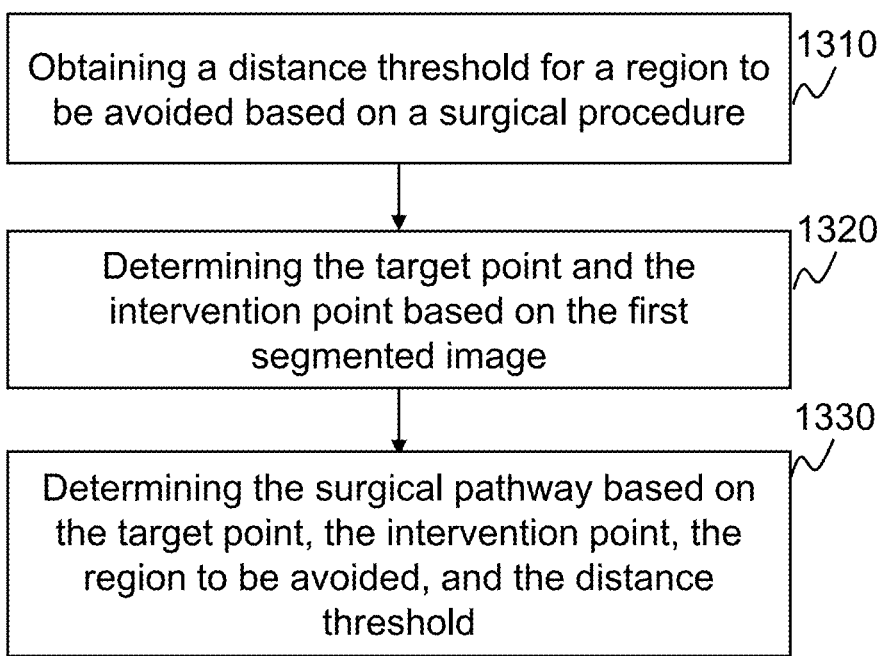
FIG. 24 is a flowchart illustrating an exemplary process for determining a surgical pathway according to some other embodiments of the present disclosure.
Figure 25:
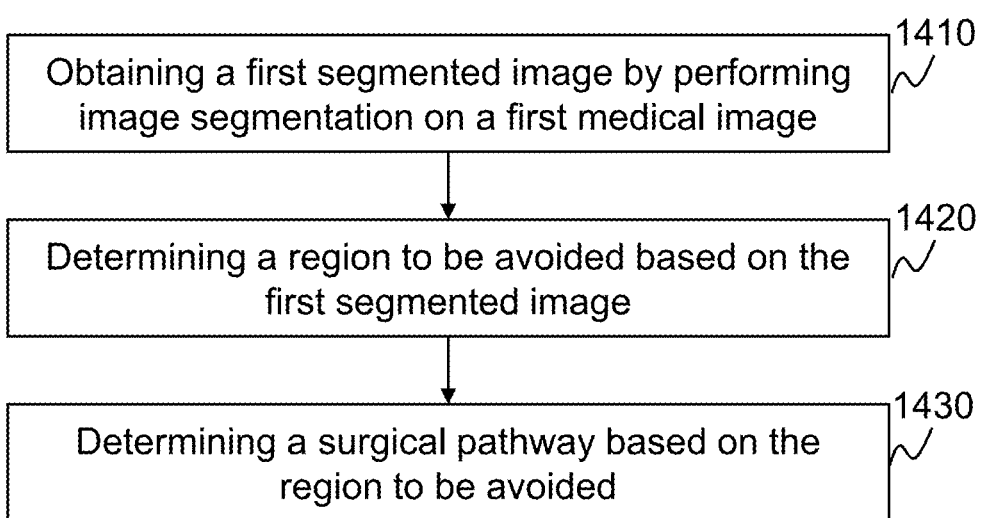
FIG. 25 is a flowchart illustrating an exemplary process for determining a surgical pathway according to some other embodiments of the present disclosure.

In some embodiments, as shown in FIG. 24, the pathway planning module 230 may be configured to obtain a distance threshold for a region to be avoided based on a surgical procedure and/or a first segmented image, and a surgical pathway may be determined based on a target point, an intervention point, the region to be avoided, and the distance threshold.

In some embodiments, the pathway planning module 230 may further include an alarm unit, a parameter adjustment unit, and a pathway conversion unit (not shown in the figure).

The alarm unit may be configured to perform a corresponding prompt operation through an alarm message when a minimum distance between the surgical pathway and the region to be avoided is less than a corresponding distance threshold.

The parameter adjustment unit may be configured to receive a first adjustment instruction and adjust the distance threshold based on the first adjustment instruction after the corresponding prompt operation is performed; and/or receive a second adjustment instruction and adjust the intervention point or the target point based on the second adjustment instruction.

The pathway conversion unit may be configured to extract marker points from the first segmented image, obtain a spatial transformation relationship between an image coordinate system and a surgical robot coordinate system based on the marker points, and convert the surgical pathway into an action pathway of the surgical robot based on the spatial transformation relationship.

In some embodiments, a process 1300 may be implemented by the surgical pathway processing system 100 (e.g., the processing device 140 of the surgical pathway processing system 100) or the surgical pathway processing system 200 (e.g., the pathway planning module 230). For example, the process 1300 may be stored in a storage device (e.g., the storage device 150, and a storage unit of the system) in the form of a program or an instruction, and the process 1300 may be implemented when a processor (e.g., the processing device 140) or modules of FIG. 2 executes/execute the program or the instruction.

In 1310, a distance threshold for a region to be avoided may be obtained based on a surgical procedure.

The surgical procedure refers to a specific type of surgery. Different surgical procedures have different operating methods, and accordingly, tissues to be avoided (i.e., regions to be avoided) are different.

The distance threshold refers to an appropriate threshold for a distance of the surgical pathway relative to the region to be avoided. If the distance between the surgical pathway and the region to be avoided reaches the distance threshold, it may indicate that the surgical pathway may successfully bypass the tissue to be avoided.

In some embodiments, the region to be avoided may be determined based on a tissue segmented image (e.g., the first segmented image), and the distance threshold may be determined based on the region to be avoided. More details regarding the determination of the region to be avoided may be found elsewhere in the present disclosure (e.g., FIG. 3 and related descriptions thereof), which are not repeated here.

In some embodiments, the distance threshold may reflect an operation accuracy of the surgical procedure. Different surgical procedures require different system spatial registration accuracies, for example, a DBS procedure requires the system spatial registration accuracy to be within 0.5 mm, and a SEEG procedure requires the system spatial registration accuracy to be within 0.8. System localization requirements for a puncture procedure may depend on a size of a specific lesion (a target organ) and a location of the lesion. Therefore, in some embodiments, the distance threshold for the region to be avoided may be determined based on the surgical procedure. For example, for the DBS procedure, a system default distance threshold for the region to be avoided may be 1 mm; for the SEEG procedure, the system default distance threshold may be 1.6 mm; and for the puncture procedure, the system default distance threshold may be 2 mm.

In some embodiments, a surgical safety check range may be set. For example, the safety check range may be set to be greater than or equal to 0.5 mm depending on the accuracy that the system is able to achieve.

In some embodiments, the region to be avoided and/or the distance threshold thereof may be adjusted based on actual circumstances and experience. For example, an operation instruction from a physician may be received to modify the region to be avoided and/or the distance threshold thereof.

In 1320, the target point and the intervention point may be determined based on the first segmented image.

In some embodiments, the target point and the intervention point may be generated automatically based on the tissue segmented image during processing of the tissue segmented image, or based on a physician's operation instruction. More details regarding the target point and the intervention point may be found elsewhere in the present disclosure (e.g., FIGS. 16-17 and related descriptions thereof), which are not repeated here.

In 1330, the surgical pathway may be determined based on the target point, the intervention point, the region to be avoided, and the distance threshold.

In some embodiments, the candidate pathway may be determined based on the target point and the intervention point. The candidate pathway may be screened based on the region to be region and the distance threshold, and the candidate pathway satisfying a condition (e.g., a distance from the region to be avoided is greater than or equal to the distance threshold) may be determined as the surgical pathway. In some embodiments, the candidate pathway may be determined based on the target point, the intervention point, and the region to be avoided. The candidate pathway may be screened based on the distance threshold, and the candidate pathway satisfying the condition may be determined as the surgical pathway. In some embodiments, the intervention point and the target point may be used as a starting point and an end point of the surgical pathway, respectively, and a reasonable surgical pathway may be generated automatically using a location of a tissue in the region to be avoided, the distance threshold, a location of the intervention point, and a location of the target point.

In some embodiments, whether the generated surgical pathway satisfies a pathway planning condition (e.g., whether the generated surgical pathway includes an interference feature, whether an intervention parameter satisfies a second predetermined condition, etc.) may be determined by verifying the generated surgical pathway, thereby determining a more reasonable surgical pathway. The verification of the surgical pathway may be similar to the verification of the candidate pathway. More details may be found in FIGS. 18-22 and related descriptions thereof, which are not repeated here.

The surgical pathway determination method provided in the embodiments of the present disclosure includes obtaining the tissue segmented image including a plurality of segmented tissues, determining the distance threshold for the region to be avoided based on the surgical procedure, selecting the intervention point and the target point on the first segmented image, and obtaining the surgical pathway based on the region to be avoided, the distance threshold, the intervention point, and the target point. In the embodiments, in formulating the surgical pathway, the surgical pathway may be obtained based on the intervention point and the target point in combination with the region to be avoided and the distance threshold. The determination of the surgical pathway considers the region to be avoided and the distance between the surgical pathway and the region to be avoided, such that the surgical pathway may bypass the region to be avoided, which avoids damaging the tissue in the region to be avoided. In addition, the surgical pathway may be obtained before surgery through calculation and processing based on the first segmented image, which avoids relying on the doctor's experience to a large extent, and improves the efficiency of obtaining the surgical pathway.

It should be noted that the above surgical pathway determination method may be performed on a console of a surgical robot, on a post-processing workstation of a medical device, or on a terminal device capable of communicating with the medical device, which is not limited thereto, and may be varied and adapted based on the needs of an actual application. In some embodiments, the surgical pathway determination method in the process 900 may be applied to the preoperative planning of the surgery, and may not be directly involved in the surgical process, but only provide a reasonable surgical pathway for the surgery in the preoperative period.

In some embodiments, the obtained surgical pathway may be manually adjusted. For example, after the surgical pathway is obtained, the surgical pathway may be adjusted based on a physician's operation instruction. In some embodiments, after the surgical pathway is obtained, the surgical pathway may be displayed in the tissue segmented image (e.g., the first segmented image) to specifically show a relationship between the surgical pathway and human tissue on a display device. In some embodiments, the surgical pathway and the tissue segmented image may be stored in a storage (e.g., a storage device of the surgical robot or a storage device of the surgical pathway processing system) for reading.

In some embodiments, a minimum distance between the surgical pathway and the region to be avoided may be obtained. If the minimum distance is less than the corresponding distance threshold, the corresponding prompt operation may be performed through the alarm message (e.g., a pop-up prompt, a voice prompt, etc.). In some embodiments, the alarm message may be used to remind to modify the surgical pathway.

In some embodiments, if tissues in the region to be avoided are complex or in large numbers, the obtained surgical pathway may not fully satisfy the condition of the distance threshold. Therefore, the minimum distance between the surgical pathway and the region to be avoided may be obtained. The minimum distance may be compared with the distance threshold corresponding to the region to be avoided. When the minimum distance is less than the distance threshold, the corresponding prompt operation may be performed through the alarm message.

In some embodiments, when the region to be avoided includes a plurality of tissues to be avoided, a distance between the surgical pathway and each tissue to be avoided may be calculated separately. The distances may be compared and prompt alarms may be issued, thereby modifying the surgical pathway as a whole to overall improve the accuracy of the surgical pathway.

When the minimum distance between the surgical pathway and the region to be avoided is less than the corresponding distance threshold, the surgical pathway may be at risk of having difficulty in bypassing the tissues that are difficult to be avoided but need to be circumvented. The alarm message may be used to prompt you to modify the surgical pathway to help confirm that the surgical pathway may accurately avoid the tissues to be avoided, thereby improving the accuracy of the surgical pathway.

In some embodiments, after the corresponding prompting operation is performed through the alarm message, a first adjustment instruction may be received, and the distance threshold may be adjusted based on the first adjustment instruction; and/or, a second adjustment instruction may be received, and the intervention point or the target point may be adjusted based on the second adjustment instruction; and the surgical pathway may be redetermined based on the region to be avoided, an adjusted target point, an adjusted intervention point, and the distance threshold.

In some embodiments, the first adjustment instruction may be used to adjust the distance threshold. Since a safety check range is considered when the distance threshold is set, appropriately adjusting the distance threshold may not affect the reasonableness of the surgical pathway. In some embodiments, the second adjustment instruction may be used to adjust the intervention point and/or the target point. Different locations of the intervention point and the target point may affect the surgical pathway. By modifying the intervention point and/or the target point, the surgical pathway may be appropriately modified. The adjustment modification of the surgical pathway may be realized by means of the adjustment instruction, which improves the accuracy of the surgical pathway, and also facilitates the user's operation of adjusting the surgical pathway during actual use.

In some embodiments, the surgical pathway may be implemented by a user or a surgical robot.

If the surgical pathway is implemented by the surgical robot, as an image coordinate system in which the tissue segmented image is located is different from a coordinate system in which the surgical robot is located, the surgical pathway obtained from the tissue segmented image may be transformed into an action pathway in the surgical robot coordinate system by a spatial transformation.

In some embodiments, marker points may be extracted on the tissue segmented image (e.g., the first segmentation image), a spatial transformation relationship between the image coordinate system and the surgical robot coordinate system may be obtained based on the marker points, and the surgical pathway may be transformed into the action pathway of the surgical robot based on the spatial transformation relationship.

The marker points may be used for spatial registration to determine the spatial transformation relationship between the image coordinate system and the surgical robot coordinate system. In some embodiments, the marker points may be located at a plurality of different locations in a space of the tissue segmented image.

The spatial transformation relationship between the image coordinate system and the surgical robot coordinate system may be determined using the marker points extracted on the tissue segmented image, and the surgical pathway may be rapidly transformed into the action pathway of the surgical robot, thereby improving the efficiency of obtaining the action pathway of the surgical robot.

In some embodiments, nucleus extraction, neural analysis, and/or predetermined element extraction may be performed on the tissue segmented image (e.g., the first segmented image) and a fusion display of a tissue sequence may be performed.

Neuronal cells are clustered together in a central part of a nervous system to form nerve nuclei, and similarly functioning nerve nuclei may form a neuronal nucleus.

In some embodiments, the nucleus extraction may be performed on $T_1$ ($T_1$-weighted imaging) and $T_2$ ($T_2$-weighted imaging) sequences of magnetic resonance (MR) imaging data of a skull, the neural analysis may be performed on a diffusion tensor imaging (DTI) sequence, and the vascular (i.e., predetermined element) extraction may be performed on computed tomography (CT) data. In some embodiments, after tissue segmentation and extraction are performed on the tissue segmented image, the fusion display of all segmented tissue sequences may be performed.

The surgical pathway determined based on the surgical pathway determination method in the embodiments of the present disclosure considers the tissues to be avoided and the distance between the surgical pathway and the tissues to be avoided, so that the surgical pathway is capable of bypassing the tissues to be avoided, thereby avoiding damaging the tissues to be avoided. Moreover, the surgical pathway may be obtained before surgery through calculation and processing based on the tissue segmented image, which avoids relying on the doctor's experience to a large extent, and improves the efficiency of obtaining the surgical pathway. In addition, the surgical robot may be driven to move based on the surgical pathway, so that the surgical robot may reach the target point smoothly.

It should be noted that the foregoing descriptions of the process 1300 are intended to be exemplary and illustrative only, and do not limit the scope of application of the present disclosure. For those skilled in the art, various corrections and changes may be made to the process 1300 under the guidance of present disclosure. However, these corrections and changes remain within the scope of the present disclosure.

In some embodiments, a process 1400 may be implemented by the surgical pathway processing system 100 (e.g., the processing device 140 of the surgical pathway processing system 100) or the surgical pathway processing system 200. For example, the process 1400 may be stored in a storage device (e.g., the storage device 150, and a storage unit of the system) in the form of a program or an instruction, and the process 1400 may be implemented when a processor (e.g., the processing device 140) or modules of FIG. 2 executes/execute the program or the instruction.

In 1410, a first segmented image may be obtained by performing image segmentation on a first medical image.

In some embodiments, the image segmentation may be performed by methods such as deep learning, active contouring, region growing, manual extraction, or the like, to obtain the first segmented image. More descriptions regarding obtaining the first segmented image may be found elsewhere in the present disclosure (e.g., FIG. 3 and related descriptions thereof), which are not repeated here.

In 1420, a region to be avoided may be determined based on the first segmented image.

In some embodiments, an overall mask, a predetermined object mask, and a to-be-intervened object mask may be obtained by segmenting the first medical image, and the region to be avoided may be determined based on the overall mask, the predetermined object mask, and the to-be-intervened object mask. More descriptions regarding determining the region to be avoided may be found elsewhere in the present disclosure (e.g., FIG. 3 and related descriptions thereof), which are not repeated here.

In 1430, a surgical pathway may be determined based on the region to be avoided.

In some embodiments, a target point and an intervention point may be automatically determined based on a user input, and the surgical pathway may be determined based on the target point, the intervention point, and the region to be avoided. In some embodiments, a distance threshold for the region to be avoided may be obtained based on a surgical procedure, and the surgical pathway may be determined based on the target point, the intervention point, the region to be avoided, and the distance threshold. More descriptions regarding determining the surgical pathway may be found elsewhere in the present disclosure (e.g., FIGS. 16-24 and related depictions thereof), which are not repeated here.

It should be noted that the foregoing descriptions of the process 1400 are intended to be exemplary and illustrative only, and do not limit the scope of application of the present specification. For those skilled in the art, various corrections and changes may be made to the process 1400 under the guidance of the present disclosure. However, these corrections and changes remain within the scope of the present disclosure.

Figure 26:
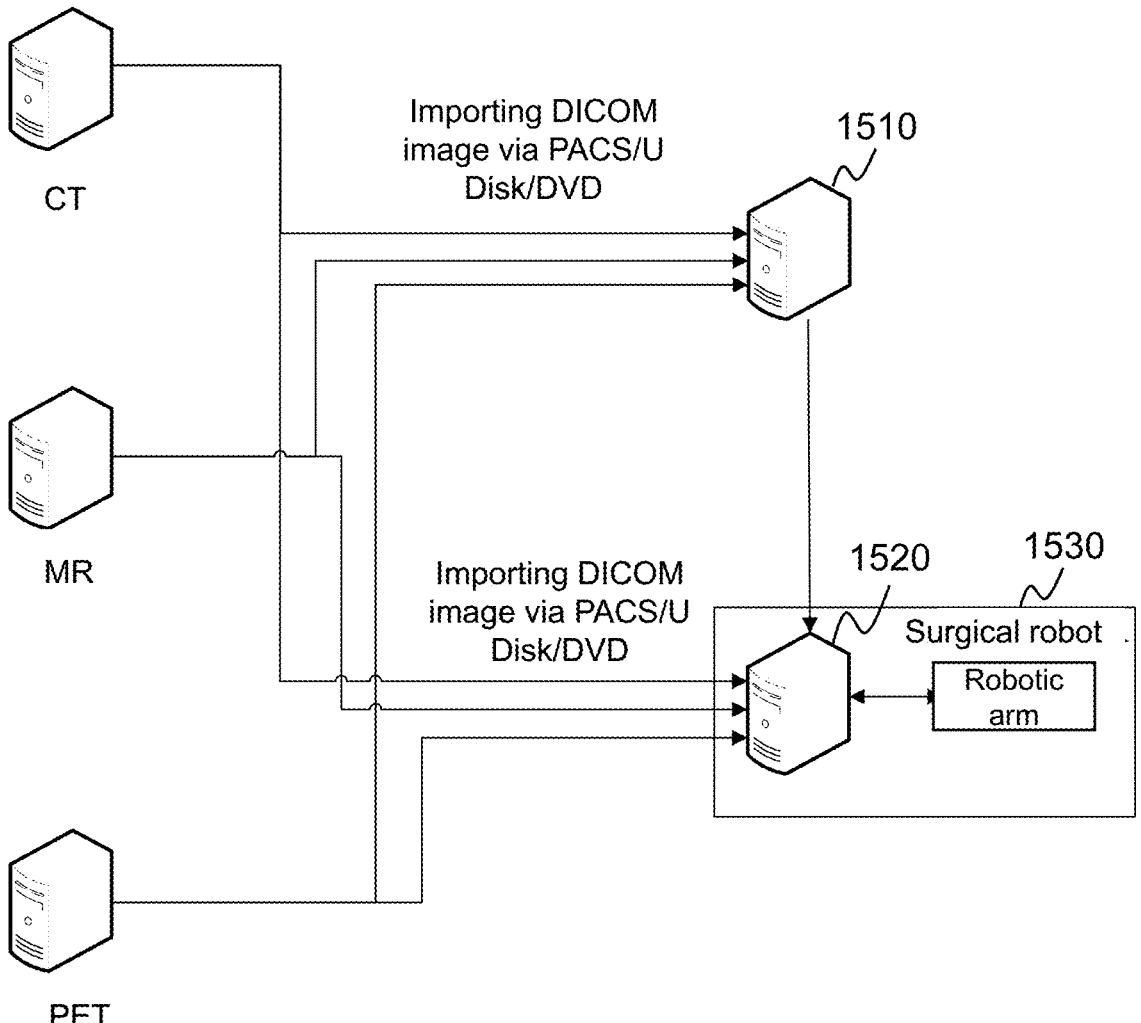
FIG. 26 is a schematic diagram illustrating an exemplary surgical processing system according to some embodiments of the present disclosure.

Merely by way of example, taking a processing server being divided into a preoperative processor and a surgical robot controller as an example, as shown in FIG. 26, in some embodiments, in order to smoothly obtain scanned image data, a preoperative processor 1510 may be connected to a scanning imaging modality device such as a PET device, an MR device, or a CT device in a wired or wirelessly manner. A patient may be examined one or more times preoperatively, and examination image data of the patient may be imported into the preoperative processor 1510 in the form of picture archiving and communication systems (PACS), a USB flash drive, or a DVD for preoperative planning analysis and processing. A preoperative planning result done on the preoperative processor 1510 may be exported to surgical robot console software 1520. The surgical robot console software 1520 may control a movement of a surgical robot 1530 based on the preoperative planning result. Of course, the examination image data may also be directly imported into the surgical robot console software 1520 in the form of the PACS, the USB flash drive, or the DVD for the preoperative planning analysis and processing to obtain the preoperative planning result. The movement of the surgical robot 1530 may be controlled based on the preoperative planning result.

Figure 27:
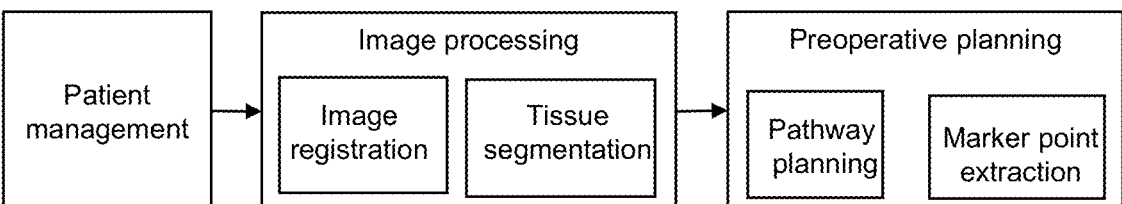
FIG. 27 is a schematic diagram illustrating an exemplary preoperative planning workflow according to some embodiments of the present disclosure.

As shown in FIG. 27, in some embodiments, in the software of the preoperative processor or the surgical robotic console software, a workflow of preoperative planning may be divided into patient management, image processing, and preoperative planning.

The patient management refers to management of scanned image data of a patient to select scanned image data to be loaded (e.g., a first medical image and a second medical image).

The image processing refers to an analysis processing of the loaded scanned image data of the patient to obtain a tissue segmented image (e.g., the first segmented image and the second segmented image). In some embodiments, if the scanned image data is a single sequence, image registration may not be required; and if the scanned image data is multiple sequences, the image registration may be performed first, and then the tissue segmented image may be obtained by performing tissue segmentation and extraction on the multiple sequences.

The preoperative planning refers to performing pathway planning (e.g., the surgical pathway determination method corresponding to the processes 700-1400) and marker point extraction on the tissue segmented image. In some embodiments, the pathway planning may be used for localization and orientation during robotic implementation of the surgical pathway. In some embodiments, the marker point extraction may be used for spatial registration to determine a spatial transformation relationship between an image coordinate system and a surgical robot coordinate system. More details regarding the pathway planning may be found in FIGS. 16-24 and related descriptions thereof, which are not repeated here.

In some embodiments, the surgical robot may include, but is not limited to, a stereotactic surgical robot.

The stereotactic surgical robot is generally used in neurosurgery. A workflow of the stereotactic surgical robot may be abstractly divided into patient image scanning, image analysis, preoperative planning, spatial registration, and pathway implementation.

Figure 28:
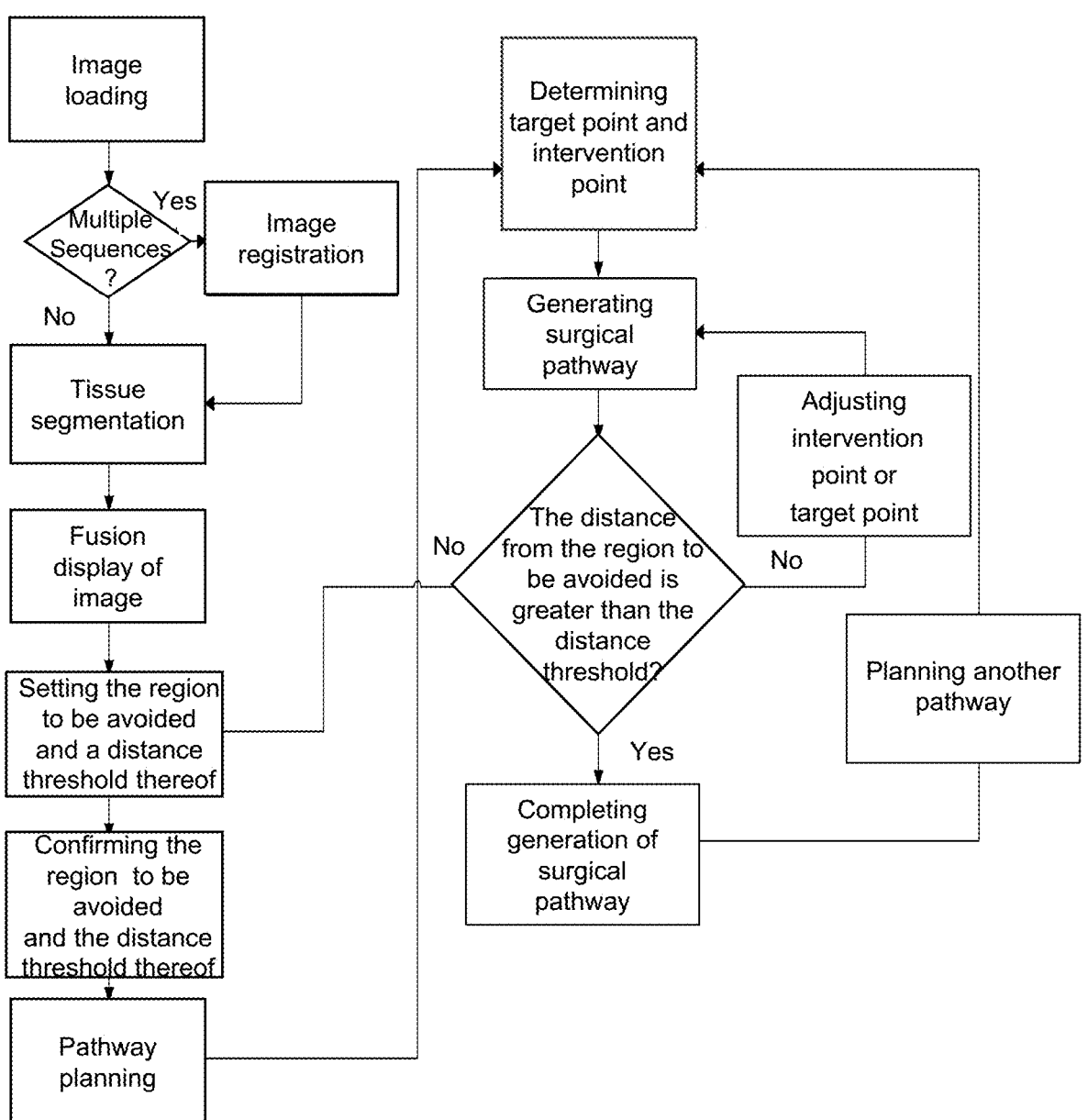
FIG. 28 is a schematic diagram illustrating an exemplary workflow of a surgical system according to some embodiments of the present disclosure.

Merely by way of example, taking application to craniocerebral surgery as an example, as shown in FIG. 28, a workflow of the surgical system may include the following. (1) Preoperative image scanning may be performed, and the scanned patient image data may be imported into a surgical robot system. (2) scanned image data to be loaded may be selected for image analysis. The image analysis may be divided into image registration, tissue segmentation, and result display. If the scanned image data is multiple sequences, the image analysis may enter tissue segmentation after image registration. Tissue segmentation may be performed for each sequence. For example, nucleus extraction may be performed on $T_1$ ($T_1$-weighted imaging) and $T_2$ ($T_2$-weighted imaging) sequences of MR, neural analysis may be performed on DTI sequences, and vessel extraction may be performed on CT data. After the tissue segmentation and extraction, the image analysis may enter the result display to fusion display all segmented tissue sequences. (3) preoperative planning may be performed after the image analysis, and the system may recommend a default region to be avoided and a default distance threshold based on the current surgical procedure (e.g., DBS, SEEG, and puncture) and segmented and extracted tissues. The user may make adjustment and confirmation based on an actual condition and experience. (4) The user may select a cranial entry point (i.e., the interventional point) and the target point on the image, respectively in combination with the fusion display of the segmented image. The system may automatically generate the surgical pathway based on the target point and the cranial entry point selected by the user, calculate a minimum distance between the surgical pathway and the region to be avoided, and determine whether the minimum distance is greater than the distance threshold. If the minimum distance is greater than the distance threshold, the surgical pathway may be valid; or if the minimum distance is less than the distance threshold, the system may explicitly prompt the user that the minimum distance of the surgical pathway from the region to be avoided is less than the distance threshold set by the system, and the surgical pathway is of great risk. (5) When the system prompts that the surgical pathway is of great risk, the user may make adjustment to the target point or the cranial entry point based on the actual situation and experience, or reset the region to be avoided and the distance threshold, thereby planning a surgical pathway satisfying the requirements.

It should be noted that the foregoing descriptions regarding FIGS. 26-28 are intended to be exemplary and illustrative only, and do not limit the scope of application of the present disclosure. For those skilled in the art, various corrections and changes may be made to FIGS. 26-28 under the guidance of the present disclosure. However, these corrections and changes remain within the scope of the present disclosure.

The embodiments of the present disclosure further provide a surgical pathway processing device comprising an image segmentation unit configured to obtain a first segmented image by performing image segmentation on a first medical image; an avoidance region determination unit configured to determine a region to be avoided based on the first segmented image; and a pathway planning unit configured to determine a surgical pathway based on the region to be avoided.

In some embodiments, the image segmentation unit may obtain an overall mask, a predetermined object mask, and a to-be-intervened object mask by segmenting the first medical image; and the avoidance region determination unit may determine the region to be avoided based on the overall mask, the predetermined object mask, and the to-be-intervened object mask.

In some embodiments, the image segmentation unit may be configured to determine a target medical image by performing a registration using finite elements based on the first segmented image.

In some embodiments, the pathway planning unit may be configured to automatically determine a target point and an intervention point based on a user input, and determine the surgical pathway based on the target point, the intervention point, and the region to be avoided. In some embodiments, the pathway planning unit may be configured to obtain a distance threshold for the region to be avoided based on a surgical procedure, and determine the surgical pathway based on the target point, the intervention point, the region to be avoided, and the distance threshold.

Embodiments of the present disclosure further provide a surgical pathway processing device comprising a surgical robot and a processing server. The processing server may be configured to obtain a surgical pathway based on the surgical pathway processing method (e.g., the processes 700-1400) as described above, and drive the surgical robot to move based on the surgical pathway.

Embodiments of the present disclosure further provide a surgical pathway processing device comprising a surgical robot, a processing server, and an imaging device. The imaging device may be configured to provide a medical image (e.g., a first medical image, and a second medical image) to the processing server. The processing server may be configured to obtain a surgical pathway based on the surgical pathway processing method (e.g., the processes 700-1400) as described above, and drive the surgical robot to move based on the surgical pathway.

In some embodiments, the above surgical pathway processing device may obtain the surgical pathway by running an executable program on the processing server based on an intervention point and a target point in formulating the surgical pathway in combination with the region to be avoided and/or the distance threshold.

Embodiments of the present disclosure further provide a surgical system comprising a surgical pathway processing system (e.g., the surgical pathway processing system 200), a surgical robot, and an imaging device. The imaging device may be configured to provide a medical image (e.g., a first medical image, and a second medical image) to the surgical pathway processing system. The surgical robot may move based on the surgical pathway provided by the surgical pathway processing system.

In some embodiments, the surgical system may further include a display device for displaying a tissue segmented image (e.g., the first segmentation image), the surgical pathway, or the like. In some embodiments, the surgical pathway may be displayed at a corresponding location on the tissue segmented image. In some embodiments, the display device may be various display devices such as an LED display screen or an OLED display screen.

In some embodiments, the surgical pathway processing system may be disposed in a processing server. The processing server may be arranged separately, or integrated into the surgical robot, or separated into a preoperative processor and a surgical robot controller.

The basic concept has been described above. Obviously, for those skilled in the art, the above detailed disclosure is only an example, and does not constitute a limitation to the present disclosure. Although not expressly stated here, those skilled in the art may make various modifications, improvements and corrections to the present disclosure. Such modifications, improvements and corrections are suggested in this disclosure, so such modifications, improvements and corrections still belong to the spirit and scope of the exemplary embodiments of the present disclosure.

Meanwhile, the present disclosure uses specific words to describe the embodiments of the present disclosure. For example, "one embodiment", "an embodiment", and/or "some embodiments" refer to a certain feature, structure, or characteristic related to at least one embodiment of the present disclosure. Therefore, it should be emphasized and noted that references to "one embodiment" "an embodiment" or "an alternative embodiment" two or more times in different places in the present disclosure do not necessarily refer to the same embodiment. In addition, certain features, structures, or characteristics in one or more embodiments of the present disclosure may be properly combined.

In addition, unless clearly stated in the claims, the sequence of processing elements and sequences described in the present disclosure, the use of counts and letters, or the use of other names are not used to limit the sequence of processes and methods in the present disclosure. While the foregoing disclosure has discussed by way of various examples some embodiments of the invention that are presently believed to be useful, it should be understood that such detail is for illustrative purposes only and that the appended claims are not limited to the disclosed embodiments, but rather, the claims are intended to cover all modifications and equivalent combinations that fall within the spirit and scope of the embodiments of the present disclosure. For example, although the implementation of various components described above may be embodied in a hardware device, it may also be implemented as a software only solution, e.g., an installation on an existing server or mobile device.

In the same way, it should be noted that in order to simplify the expression disclosed in this disclosure and help the understanding of one or more embodiments of the invention, in the foregoing description of the embodiments of the present disclosure, sometimes multiple features are combined into one embodiment, drawings or descriptions thereof. This method of disclosure does not, however, imply that the subject matter of the disclosure requires more features than are recited in the claims. Rather, claimed subject matter may lie in less than all features of a single foregoing disclosed embodiment.

In some embodiments, counts describing the quantity of components and attributes are used. It should be understood that such counts used in the description of the embodiments use the modifiers "about", "approximately" or "substantially" in some examples. Unless otherwise stated, "about", "approximately" or "substantially" indicates that the stated figure allows for a variation of ±20%. Accordingly, in some embodiments, the numerical parameters used in the disclosure and claims are approximations that can vary depending upon the desired characteristics of individual embodiments. In some embodiments, numerical parameters should consider the specified significant digits and adopt the general digit retention method. Although the numerical ranges and parameters used in some embodiments of the present disclosure to confirm the breadth of the range are approximations, in specific embodiments, such numerical values are set as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A surgical pathway processing system, comprising an image segmentation module, an avoidance region determination module, and a pathway planning module, wherein the surgical pathway processing system performs operations including:

obtaining, by the image segmentation module, a first segmented image by performing image segmentation on a first medical image;

determining, by the avoidance region determination module, a region to be avoided based on the first segmented image; and determining, by the pathway planning module, a surgical pathway based on the region to be avoided, wherein the obtaining the first segmented image includes: obtaining an overall mask, a predetermined object mask, and a to-be-intervened object mask by segmenting the first medical image, wherein the to-be-intervened object mask refers to a mask of a region to be intervened during an interventional procedure, and the determining the region to be avoided includes determining the region to be avoided based on the overall mask, the predetermined object mask, and the to-be-intervened object mask.

2. The surgical pathway processing system of claim 1, wherein the determining the region to be avoided based on the overall mask, the predetermined object mask, and the to-be-intervened object mask includes:

determining a target mask based on the overall mask and the predetermined object mask; and determining the region to be avoided based on the target mask and the to-be-intervened object mask.

3. The surgical pathway processing system of claim 2, wherein the determining the target mask based on the overall mask and the predetermined object mask includes:

determining the target mask by subtracting the predetermined object mask from the overall mask;

determining a non-intervening object mask by subtracting the to-be-intervened object mask from the target mask; and determining the region to be avoided includes:

performing a connected component analysis on the non-intervening object mask; and determining a connected component satisfying a first predetermined condition as the region to be avoided.

4. The surgical pathway processing system of claim 1, wherein the obtaining the first segmented image by performing the image segmentation on the first medical image includes:

determining a target medical image by performing a registration using finite elements based on the first segmented image.

5. The surgical pathway processing system of claim 4, wherein the determining the target medical image by performing the registration using the finite elements based on the first segmented image includes:

obtaining a second medical image of a target object, the second medical image and the first medical image including images of the target object at different periods;

obtaining a second segmented image by segmenting at least a portion of the second medical image;

obtaining a rigid registration result by performing a rigid registration on the target object in the first segmented image and the target object in the second segmented image;

obtaining an elastic registration result by performing an elastic registration on the target object in the rigid registration result and the target object in the second segmented image; and obtaining the target medical image by processing the first segmented image based on the rigid registration result and the elastic registration result.

6. The surgical pathway processing system of claim 5, the operations further including:

constructing a mechanical model of the target object based on the target object in the rigid registration result;

obtaining a surface elasticity registration result by performing a surface elasticity registration on the target object in the first segmented image and the target object in the second segmented image;

obtaining a deformation field of each node of the mechanical model of the target object by solving the mechanical model using a difference between the rigid registration result of the target object and the surface elasticity registration result of the target object as a boundary condition; and obtaining the target medical image by processing the first segmented image based on a rigid transformation matrix in the rigid registration result and the deformation field of each node of the mechanical model of the target object.

7. The surgical pathway processing system of claim 6, the operations further including:

obtaining a transformed first medical image by performing translation and/or rotation on the first medical image based on the rigid transformation matrix; and obtaining the target medical image by performing translation and/or rotation on each node of the mechanical model of the target object in the transformed first medical image based on the deformation field of each node of the mechanical model of the target object.

8. The surgical pathway processing system of claim 5, the operations further including:

obtaining a third medical image of the target object, the third medical image including an enhanced type of image, the second medical image including a plain scanned type image obtained after image transformation of the third medical image.

9. The surgical pathway processing system of claim 4, the operations further including:

obtaining a third medical image of a target object, wherein the third medical image includes an enhanced type image, the third medical image and the first medical image including images of the target object at different periods;

obtaining a third mask image corresponding to the third medical image by extracting the target object and an internal detail mask from the third medical image;

obtaining a fourth mask image corresponding to the target medical image by extracting the target object and an internal detail mask from the target medical image;

calculating a count of duplicate pixel points in a region of interest in the third mask image and a region of interest in the fourth mask image;

obtaining a validation value based on the count of duplicate pixel points, a count of pixel points in the region of interest in the third mask image, and a count of pixel points in the region of interest in the fourth mask image; and if the verification value is greater than a predetermined threshold, determining that a verification of a registered image passes, and if the verification value is not greater than the predetermined threshold, determining that the verification of the registered image does not pass.

10. The surgical pathway processing system of claim 1, wherein the determining the surgical pathway based on the region to be avoided includes:

automatically determining a target point and an intervention point based on a user input; and determining the surgical pathway based on the target point, the intervention point, and the region to be avoided.

11. The surgical pathway processing system of claim 10, wherein the automatically determining the target point and the intervention point based on the user input includes:

receiving a first operation of a user on the first segmented image, and determining the target point in response to the first operation;

receiving a second operation of the user on the first segmented image, and determining a reference point in response to the second operation;

determining a reference pathway based on the target point and the reference point, the reference pathway including a straight line connecting the target point and the reference point; and determining the intervention point based on the reference pathway.

12. The surgical pathway processing system of claim 10, wherein the automatically determining the intervention point based on the user input includes:

determining an action pathway of a second operation of a user on the first segmented image;

determining a reference pathway based on the action pathway; and determining the intervention point based on the reference pathway.

13. The surgical pathway processing system of claim 11, the operations further including:

determining a candidate pathway based on the reference pathway; and determining the surgical pathway by verifying the candidate pathway.

14. The surgical pathway processing system of claim 13, the operations further including:

determining whether the candidate pathway includes an interference feature and/or whether an intervention parameter of the candidate pathway satisfies a second predetermined condition; and if the candidate pathway does not include the interference feature and/or the intervention parameter of the candidate pathway satisfies the second predetermined condition, determining that a verification result of the candidate pathway is passed; or if the candidate pathway includes the interference feature and/or the intervention parameter of the candidate pathway does not satisfy the second predetermined condition, determining that the verification result of the candidate pathway is not passed.

15. The surgical pathway processing system of claim 14, the operations further including:

selecting a point in the candidate pathway that is a predetermined distance away from the target point as a verification point;

obtaining a voxel pixel value of the verification point in a predetermined neighborhood, and determining whether the voxel pixel value includes a value in a predetermined pixel set;

if the voxel pixel value includes a value in the predetermined pixel set, determining that the candidate pathway includes the interference feature; and if the voxel pixel value does not include a value in the predetermined pixel set, updating the verification point in the candidate pathway until a voxel pixel value of each verification point in the candidate pathway in a corresponding predetermined neighborhood does not include a value in the predetermined pixel set, and determining that the candidate pathway does not include the interference feature.

16. The surgical pathway processing system of claim 14, the operations further including:

determining a pathway length and/or an intervention angle of the candidate pathway;

determining whether the pathway length is less than or equal to a predetermined length threshold and/or determining whether the intervention angle is less than or equal to a predetermined angle threshold;

if the pathway length is less than or equal to the predetermined length threshold, and/or the intervention angle is less than or equal to the predetermined angle threshold, determining that the intervention parameter of the candidate pathway satisfies the second predetermined condition; and if the pathway length is greater than the predetermined length threshold, and/or the intervention angle is greater than the predetermined angle threshold, determining that the intervention parameter of the candidate pathway does not satisfy the second predetermined condition; wherein the second predetermined condition includes the predetermined length threshold and the predetermined angle threshold.

17. The surgical pathway processing system of claim 1, wherein the determining the surgical pathway based on the region to be avoided includes:

obtaining a distance threshold for the region to be avoided based on a surgical procedure; and determining the surgical pathway based on a target point, an intervention point, the region to be avoided, and the distance threshold.

18. A surgical pathway processing method performed by the surgical pathway processing system of claim 1, comprising:

obtaining the first segmented image by performing the image segmentation on the first medical image;

determining the region to be avoided based on the first segmented image; and determining the surgical pathway based on the region to be avoided, wherein the obtaining the first segmented image includes obtaining an overall mask, a predetermined object mask, and a to-be-intervened object mask by segmenting the first medical image, wherein the to-be-intervened object mask refers to a mask of a region to be intervened during an interventional procedure; and the determining the region to be avoided includes determining the region to be avoided based on the overall mask, the predetermined object mask, and the to-be-intervened object mask.

19. A surgical pathway processing device, comprising:

a display device;

a surgical robot; and a control device, comprising one or more processors and a storage, wherein the storage includes operation instructions configured to direct the one or more processors to perform operations including:

obtaining a first segmented image by performing image segmentation on a first medical image displayed by the display device;

determining a region to be avoided based on the first segmented image;

determining a surgical pathway based on the region to be avoided; and driving the surgical robot to move based on the surgical pathway, wherein the obtaining the first segmented image includes obtaining an overall mask, a predetermined object mask, and a to-be-intervened object mask by segmenting the first medical image, wherein the to-be-intervened object mask refers to a mask of a region to be intervened during an interventional procedure; and the determining the region to be avoided includes determining the region to be avoided based on the overall mask, the predetermined object mask, and the to-be-intervened object mask.

20. The surgical pathway processing system of claim 1, the operations further including:

obtaining a to-be-avoided object mask by segmenting the first medical image;

performing a connected component analysis on the to-be-avoided object mask; and determining a connected component satisfying a first predetermined condition as the region to be avoided.

\*  \*  \*  \*  \*